US009839644B2

(12) United States Patent
Kumar

(10) Patent No.: US 9,839,644 B2
(45) Date of Patent: *Dec. 12, 2017

(54) FORMULATIONS AND METHODS FOR TREATMENT OF METABOLIC SYNDROME

(71) Applicant: ARKAY Therapeutics, LLC, East Windsor, NJ (US)

(72) Inventor: Ravi Seshagirirao Kumar, East Windsor, NJ (US)

(73) Assignee: Arkay Therapeutics, LLC, East Windsor, NJ (US)

( * ) Notice: Subject to any disclaimer, the term of this patent is extended or adjusted under 35 U.S.C. 154(b) by 32 days.

This patent is subject to a terminal disclaimer.

(21) Appl. No.: 15/063,000

(22) Filed: Mar. 7, 2016

(65) Prior Publication Data

US 2016/0213694 A1 Jul. 28, 2016

Related U.S. Application Data

(63) Continuation-in-part of application No. 14/848,972, filed on Sep. 9, 2015.

(Continued)

(51) Int. Cl.
*A61K 31/635* (2006.01)
*A61K 31/155* (2006.01)
(Continued)

(52) U.S. Cl.
CPC .......... *A61K 31/635* (2013.01); *A61K 31/155* (2013.01); *A61K 31/40* (2013.01);
(Continued)

(58) Field of Classification Search
None
See application file for complete search history.

(56) References Cited

U.S. PATENT DOCUMENTS 3,598,122 A 8/1971 Zaffaroni
3,598,123 A 8/1971 Zaffaroni
(Continued)

FOREIGN PATENT DOCUMENTS

EP 2727587 5/2014
WO WO 2004017896 3/2004
(Continued)

OTHER PUBLICATIONS

Hristova, The Eurasian Journal of Medicine, 2011, 43, 141-145.
(Continued)

*Primary Examiner* — Karl J Puttlitz
(74) *Attorney, Agent, or Firm* — Davidson, Davidson & Kappel, LLC

(57) ABSTRACT

Formulations and methods of providing an orally-active anti-metabolic disease Fixed Dose Combinations (FDC) for use as personalized medicine to treat different components of the Metabolic Syndrome or Insulin resistance syndrome such as Type II diabetes, Hypertension, Hyperlipidemia and Obesity are disclosed. Pharmaceutical compositions of anti-inflammatory and pancreatic beta-cell centric drug formulations and methods comprising of NSAIDS in general and selective Cox-2 inhibitors in particular and one or more anti-T2DM or anti-hypertensive or anti-hyperlipidemic or anti-obesity drugs formulated to exhibit pre-determined modified release kinetics to achieve therapeutic as well as kinetic synergies are disclosed.

21 Claims, 12 Drawing Sheets

Lean animal

Obese insulin resistant animal

Related U.S. Application Data

(60) Provisional application No. 62/047,766, filed on Sep. 9, 2014.

(51) Int. Cl.
*A61K 31/41* (2006.01)
*A61K 38/28* (2006.01)
*A61K 31/40* (2006.01)
*A61K 31/415* (2006.01)
*A61K 31/522* (2006.01)
*A61K 45/06* (2006.01)

(52) U.S. Cl.
CPC ............ *A61K 31/41* (2013.01); *A61K 31/415* (2013.01); *A61K 31/522* (2013.01); *A61K 38/28* (2013.01); *A61K 45/06* (2013.01)

(56) References Cited

U.S. PATENT DOCUMENTS

| | | |
|---|---|---|
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,151,273 A | 4/1979 | Riegelman et al. |
| 4,201,211 A | 5/1980 | Chandrasekaran et al. |
| 4,229,447 A | 10/1980 | Porter |
| 4,230,105 A | 10/1980 | Harwood |
| 4,292,299 A | 9/1981 | Suzuki et al. |
| 4,292,303 A | 9/1981 | Keith et al. |
| 4,327,725 A | 5/1982 | Cortese et al. |
| 4,343,789 A | 8/1982 | Kawata et al. |
| 4,476,116 A | 10/1984 | Anik |
| 4,596,795 A | 6/1986 | Pitha |
| 4,624,848 A | 11/1986 | Lee |
| 4,755,386 A | 7/1988 | Hsiao et al. |
| 4,871,549 A | 10/1989 | Ueda et al. |
| 4,968,509 A | 11/1990 | Radebaugh |
| 5,011,692 A | 4/1991 | Fujioka et al. |
| 5,017,381 A | 5/1991 | Maruyama et al. |
| 5,116,817 A | 5/1992 | Anik |
| 5,190,970 A | 3/1993 | Pan et al. |
| 5,229,135 A | 7/1993 | Philippon et al. |
| 5,260,068 A | 11/1993 | Chen |
| 5,260,069 A | 11/1993 | Chen |
| 5,281,420 A | 1/1994 | Kelm et al. |
| 5,322,655 A | 6/1994 | Ebey |
| 5,336,168 A | 8/1994 | Sibalis |
| 5,340,591 A | 8/1994 | Nakano et al. |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,561,165 A | 10/1996 | Lautt et al. |
| 5,567,441 A | 10/1996 | Chen |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,700,485 A | 12/1997 | Berde et al. |
| 5,723,269 A | 3/1998 | Akagi et al. |
| 5,739,136 A | 4/1998 | Ellinwood, Jr. et al. |
| 5,837,280 A | 11/1998 | Kenealy et al. |
| 5,837,284 A | 11/1998 | Mehta et al. |
| 5,840,329 A | 11/1998 | Bai |
| 5,858,401 A | 1/1999 | Bhalani |
| 5,869,090 A | 2/1999 | Rosenbaum |
| 5,977,175 A | 11/1999 | Lin |
| 6,083,518 A | 7/2000 | Lindahl |
| 6,142,939 A | 11/2000 | Eppstein et al. |
| 6,391,452 B1 | 5/2002 | Antonsen et al. |
| 6,465,014 B1 | 10/2002 | Moroni et al. |
| 6,527,716 B1 | 3/2003 | Eppstein et al. |
| 6,611,706 B2 | 8/2003 | Avrahami et al. |
| 6,667,048 B1 | 12/2003 | Quay et al. |
| 6,708,060 B1 | 3/2004 | Avrahami et al. |
| 6,711,435 B2 | 3/2004 | Avrahami et al. |
| 6,846,800 B1 | 1/2005 | Johannsson et al. |
| 6,923,983 B2 | 8/2005 | Morgan et al. |
| 6,929,801 B2 | 8/2005 | Klose et al. |
| 6,932,983 B1 | 8/2005 | Straub et al. |
| 6,946,144 B1 | 9/2005 | Jordan |
| 6,960,563 B2 | 11/2005 | Egbaria et al. |
| 7,632,818 B2 | 12/2009 | Gottlieb |
| 8,008,328 B2 | 8/2011 | Saxena et al. |
| 8,367,418 B2 | 2/2013 | Monte et al. |
| 8,431,552 B2 | 4/2013 | Chen |
| 8,507,451 B1 | 4/2013 | Wang et al. |
| 8,435,550 B2 | 5/2013 | Jin Chiang et al. |
| 8,586,069 B2 | 11/2013 | Stewart et al. |
| 8,586,529 B2 | 11/2013 | Saito et al. |
| 8,586,607 B2 | 11/2013 | Ulven et al. |
| 8,759,334 B2 | 6/2014 | Laurent Raymond et al. |
| 2003/0171407 A1 | 9/2003 | Freese et al. |
| 2004/0013734 A1 | 1/2004 | Babcock et al. |
| 2006/0167045 A1 | 7/2006 | Waldstreicher et al. |
| 2007/0087048 A1 | 4/2007 | Abrams et al. |
| 2013/0273154 A1 | 10/2013 | Fayad et al. |
| 2014/0037739 A1 | 2/2014 | Schentag et al. |
| 2016/0213694 A1 | 7/2016 | Kumar |

FOREIGN PATENT DOCUMENTS

| | | |
|---|---|---|
| WO | WO 2005009412 | 2/2005 |
| WO | WO 200814471 | 1/2008 |
| WO | WO 2010086375 | 8/2010 |
| WO | WO 2011078993 | 6/2011 |

OTHER PUBLICATIONS

Tota-Maharaj et al., Current Opinion in Cardiology, 2010, 25, 502-512.
Howes, Therapeutics and Clinical Risk Management, 2007, 3(5), 831-845.
Hermansen et al., Vascular Health and Risk Management, 2008, 4(3), 561-574.
Reynolds, Diabetes, Metabolic Syndrome and Obesity: Targets and Therapy, 2009, 2, 127-134.
Telmisartan, Valsartan Lower Risk of CVD Complications in Diabetics. Medscape. Jul. 8, 2013.
Diovan® (Valsartan) Package Insert © Novartis Jul. 2015.
Celebrex® (Celecoxib) Data Sheet © Pfizer New Zealand Ltd Oct. 2, 2014.
Andraws, R and D.L. Brown (2007) Effect of inhibition of Renin-angiotensin system on development of type 2 diabetes mellitus (meta-analysis of randomized trial). Am. J. Cardiol. 99: 1006-1012.
Boucher. J., A. Kleinridders and R. Kahn (2014) Insulin receptor signaling in normal and insulin-resistant states. Cold Spring Harbor Persp. in Biol. 1-23. (Abstract Only).
Chatzigeorgiou, A., A. Halapas, K. Kalafatakis and E. Kamper (2009) The use of animal models in the study of Diabetes Mellitus. In Vivo 23:245-258.
Chen, J., D. Liu, Q. Bai, J. Song, J. Guan, J. Gao, B. Liu, X. Ma and Y. Du (2011) Celecoxib attenuates liver steatosis and inflammation in non-alcoholic steatohepatits by high fat diet in rats. Molecul. Med. Rep. 4: 811-816.
Coenen, K.R., M.R. Gruen, A. Chait, and A.H. Hasty (2007) Diet-induced increased in adiposity, but not plasma lipids, promote macrophage infiltration into white adipose tissue. Diabetes 56: 564-573.

(56) References Cited

OTHER PUBLICATIONS

Cole, B.K., R. S.R. Keller, R. Wu, J.D. Carter, J.L. Nadler, and C.S. Nunemaker (2010) Valsartan protects pancreatic islets and adipose tissue from the inflammatory and metabolic consequences of a high-fat diet in mice. Hypertension 55: 715-721.
Chrysovergis, K., X. Wang, J. Kosak, S. Lee, J.S. Kim, J.F. Foley, G. Trevelos, S. Singh, S. Baek, and T.E. Eling (2014) NAG-1/GDF-15 prevents obesity by increasing thermogenesis, lipolysis and oxidative stress. Intl. J. Obesity 38: 1555-1564.
Deans, K.A. and Sattar, N. (2006) "Anti-inflammatory" drugs and their effects on type 2 diabetes. Diabetes Technoll There. 8 (1): 18-27. (Abstract Only).
De Artinano, A. and M.M. Castro (2009) Experimental rat models to study the metabolic syndrome. British. J. Nutrition 102: 1246-1253.
Erik, P., and S. Klein (2009) Pathogenesis and Pathophysiology of cardiometabolic syndrome. J. Clin. Hypertension 11 (12):761-765.
Fjaere, E., U.L Aune, K. Roen, A.H. Keenan, T. Ma, K. Borkowsky, D.M. Kristensen, G.W. Novotny, T. Mandrup-Poulesen, B.D. Hudson, G. Milligan, Y. Xi, J.W. Newman, F.G. Haj, B. Liaset, K. Kristiansen, and L. Madsen (2014) Indomethacin treatment prevents high-fat diet-induced obesity and insulin resistance, but not glucose intolerance in C57BL/6J mice. j. biol. Chem. Apr. 17, 2014.
Fujita, H., M. Kakei, H. Fujishima, T. Morii, Y. Yamada, A. Qi and M. Breyer (2007) Effect of selective cyclooxygenase-2 (COX-2) inhibitor on glucose-stimulated insulin secretion in C57BL/6 mice. Biochem. Biphys. Res. Commun. 363 (1): 37-43.
Garber, A.J. and 19 more (2015) American Association of Clinical Endocrinologists' comprehensive diabetes management algorithm 2013 consensus statement. Endocrine Practice 21(4): Apr. 2015.
Gonzalez-Ortiz, M., P. Pascoe-Gonzalez, E. Martinez-Abundis, A. Kam-Ramos, and E. Hernandez-Salazar (2005) Effect of celecoxib, a cyclooxygenase-2 specific inhibitor, on insulin sensitivity, C-reactive protein, homocysteine, and metabolic profile in overweight subjects. Met. Synd. Relat. Disord. Summer 3(2): 95-101.
Goldfine, A.B.. P.R. Conlin, F. Halperin, J. Koska, P. Permana, D. Schwenke. S.E. Shoelson and P.D. Raven (2013) Salicylate (Salsalate) in patients with Type 2 Diabetes: A Randomized trial. Ann. Intern. Med. 159(1): 1-12.
Hsieh, P., J. Jin, C. Chiang, P. Chan, C. Chen, and K. Shih (2009) Cox-2 mediated inflammation in fat is crucial for obesity-linked insulin resistance. Obesity, J. 17(6): 1150-1157.
Hotamisligil, G.S., P. Arner, J.F. Caro, R.L. Atkinson, and B.M. Spiegelman (1995) Increased adipose tissue expression of tumor necrosis factor-alpha in human obesity and insulin resistance. J. Clin. Invest. 95: 2409-2415.
Khan. Z., Y.E. Cholera, P. Kumar, L.D. du Toit, V.M.K. Ndescendo and V. Pillay (2013) A novel multi-layered multiniisc oral tablet for chronotherapeutic drug delivery. Biomed. Res. Intl. Article ID: 569470, 16 pages.
Leung, P.S. (2007) Mechanisms of protective effects induced by blockade of the renin-angiotensin system: novel role of the pancreatic islet Angiotensin-converting system in type 2 diabetes. Diabetes. Med. 24 (2): 110-116. (Abstract Only).
Liu, T., K. Shih, C. Kao, Cheng, W and P. Hsieh (2009) Importance of cyclooxygenase 2-mediated low-grade inflammation in the development of fructose-induced insulin resistance in rats. Chne. J. Phsysiol. 52(2): 65-71.
Matsui, Y. ., Y. Hirasawa, T. Sugiura, T. Toyoshi, K. Kyuki and M. Ito (2010) Metformin reduces body weight gain and improves glucose tolerance in high-fat diet-fed C57BL/6J mice. Bill. Pharm. Bull. 33(6): 963-970.
McMurray, J.J., R.R. Holman, S.M. Huffier, M.A. Bethel and the NAVIGATOR Clinical study group (2010) Effect of Valsartan on the incidence of diabetes and cardiovascular events. N. Engl. J. Med. 362 (16): 1477-1490.
Mitorou, P., S. A. Raptis, and G. Dimitriadis (2013) Insulin action in morbid obesity: a focus on muscle and adipose tissue. Hormones 12 (2): 201-2013.

Oshima, H., M.M. Take and M. Oshima (2006) Destruction of pancreatic beta-cells by the transgenic induction of prostaglandin E2 in the islets. J. Biol.Chem. 281(39): 29330-29336.
Poitout, V. and Robertson, R.P. (2008) Glucolipotoxicity: Fuel excess and b-cell dysfunction. Endocrinee Reviews 29 (3): 351-366.
Quatanani, M. and Lazar, M.A. (2007) Mechanisms of obesity-associated insulin resistance: many choices on the menu. Genes & Dev. 21: 1443-1455.
Qi, L., M. Saberi, E. Zmuda, Y. Wang, J. Altarejos, X. Zhang (2009) Adipocyte CREB promotes insulin resistance in obesity. Cell Metab. 9: 277-86.
Ramakhelawon, B., E.J. hennessy, M. Menager, T.D. Ray, F.D. Sheedy, S. Hutchison, A. Wanschel, S. Oldebeken, M. Geoffrion, W. Spiro, G. Miller, R. McPherson, K.J. Rayner and K.J. Moore (2014) Netrin-1 promotes adipose macrophage retention and insulin resistance in obesity (Nature Medicine 20 (4):377-384.
Sabio, G., M. Das, A. Mora, Z. Zhang, J.Y. Jun, and H.J. Ko (2008) A stress signaling pathway in adipose tissue regulates hepatic insulin resistance. Science 322: 1539-1543.
Saltiel, A.R. (2000) Sries Introduction: the molecular basis of insulin resistance: implications for metabolic and cardiovascular diseases. J. Clin. Invest. 100 (2): 163-164.
Sauter, N., C. Thienel, Y. Plutino, K. Kampe, E. Dror, S. Traub, K. Tamper, B. Edat, F.Attou, J. Kerr-Conte, A.W. Jehle, M. Boni-Schnetzier and M. Donath (2015) Angiotensin II induces interleukin-1b-mediated islet inflammation and b-cell dysfunction independently of vasoconstrictive effects, Diabetes 64: 1273-1283.
Shende, P., C. Shrawne and R.S. Gand (2012) Multi-layered Tablet: Current Scenarios and recent advances. Intl. J. Drug Del. 4: 418-426.
Shi, H., M.V. Kokoeva, K. Inouye, I. Tzameli, H. Yin, J.S. and Flier (2006) TLR4 links innate immunity and fatty acid-induced insulin resistance. J. Clin. Invest. 116: 3015-3025.
Shu, C.J., C. Benoist, and D. Mathis (2012) The immune system's involvement in obesity-driven type 2 diabetes. Semin. Immunol. 24 (6): 436-442.
Statistics about diabetes (2014) Data from the National Diabetes Statistics Report (released Jun. 10, 2014), American Diabetes Association.Sullivan, P.W. et al. (2007) The medical cost of cardiometabolic risk factors in the united states. Obesity 15 (12): 3150-3158.
Sullivan, P.W., V. Ghuschyan, H.R. Wyatt, J.O. Hill (2007) The medical cost of cardiometabolic risk factors in the United States. Obesity 15 (12): 315-3158.
Tateya, S., F. Kim, and Y. Tamori (2013) Recent advances in obesity-induced inflammation and insulin resistance. Front. Endocrinol. Aug. 8; 4: 93.
Tian, Y.F., W.C. Chang. C.H. Loh, and P.S. Hsieh (2014) Leptin-mediated inflammatory signaling crucially links visceral fat inflammation to obesity-associated beta-cell function. Life Sci. 116(1): 51-58. (Abstract Only).
Tirabassi, R.S. et al. (2004) The BBZDR/wor rat model for investigating complications of Type 2 Diabetes Mellitus. ILAR J. 45 (3): 292-302.Erik, P. et al (2009) Pathogenesis and Pathophysiology of cardiometabolic syndrome. J. Clin. Hypertension 11 (12): 761-765.
Uysal, K.T. et al., S.M. Wiesbrook, M.W. Marino, and G.S. Hotamisligil (1997) Protection from obesity-induced insulin resistance in mice lacking TNF-a function. Nature 389: 610-614.
Van der Zijl, N.R. et al. (2011) Valsartan improves (beta)-cell function and insulin sensitivity in subjects with impaired glucose metabolism: a randomized control trial. Diabetes Care 34 (4): 845-851.
Visser, M., L.M. Bouter, G.M. McQuillan, M.H. Wener, and T.B. Harris (1999) Elevated C-reactive protein levels in over weight and obese adults. JAMA 282: 2131-2135.
Wang, X., K. Chrysovergis, J. Kosak, and T.E. Eling (2014) Lower inflammasome activity in NAG-1 mice is linked to a resistance to obesity and increased insulin sensitivity. Obesity 22(5): 1256-1263.
Woo, S., H. Xu. H. Li, Y. Zhao, X. Hu, J. Zhao, X. Guo, T. Guo, R. Botchlett, T. Qi, Y. Pei, J. Zheng, Y. Xu, X. An, L. Cjen, L. Chen, Q. Li, X. Xiao, Y. Huo, and C.Wu (2014) Metformin ameliorates hepatic steatosis and inflammation without altering phenotype in diet-induced obesity. PLOS ONE 9 (3): e91111.

(56) References Cited

OTHER PUBLICATIONS www.drugstorenews.com Sep 24, 2013. From GBI Research, Global Business Intelligence.
www.biovision.com.
www.cdc.gov Mortality data 2010.
Dalia Buffery, "Cardiometabolic Risk Factors: Novel Approaches Can Improve Patient Outcomes", American Health & Drug Benefits, vol. 6, No. 7, pp. 363-364.
International Search Report Corresponding to International Application No. PCT/US15/49157, dated Dec. 14, 2015.
Sauter, et al. "Angiotensin II Induces Interleukin 1b Mediated Islet Inflammation and b-Cell Dysfunction Independently of Vasoconstrictive Effects" Diabetes, vol. 64, Apr. 2015. pp. 1273-1283.
R. Paul Robertson, "Dominance of Cyclooxygenase-2 in the Regulation of Pancreatic Islet Prostaglandin Synthesis" Diabetes, vol. 47, Sep. 1998. pp. 1379-1383.
Gordon C. Weir, et al. "Five Stages of Evolving-Cell Dysfunction During Progression to Diabetes" Diabetes, vol. 53, Supplement 3, Dec. 2004. pp. S16-S21.
R. Paul Robertson, et al. "Glucolipotoxicity—Fuel Excess and B-Cell Dysfunction" Endocrine Reviews, vol. 29, May 2008. pp. 351-366.
Sanshiro Tateya, et al. "Recent advances in obesity-induced inflammation and insulin resistance" Frontiers in Endocrinology, vol. 4, Article 93, Aug. 8, 2013. pp. 1-14.
American Diabetes Association, "Standards of Medical Care in Diabetes" American Diabetes Association Position Statement: Standards of Medical Care in Diabetes, Spring 2015. Diabetes Care 2015, vol. 38(Suppl. 1). pp. S1-S94.
Chengyi Jenny Shu, et al. "The immune system's involvement in obesity-driven type 2 diabetes" Semin Immunol, vol. 24 (6), Dec. 2012. pp. 436-442.
Alan R. Saltiel. "The molecular and physiological basis of insulin resistance:emerging implications for metabolic and cardiovascular diseases" The Journal of Clinical Investigation, vol. 106, No. 2, Jul. 2000. pp. 163-164.

Lean animal

Obese insulin resistant animal

Insulin dependence of Metformin

Diet-induced Obese (DIO) Mice with Insulin Resistance & Beta Cell Dysfunction: Insulin Insufficiency is the hallmark of gradual loss of efficacy of insulin-dependent Metformin and progressive deterioration of glycemic control

FORMULATIONS AND METHODS FOR TREATMENT OF METABOLIC SYNDROME

This application is a continuation-in-part of U.S. application Ser. No. 14/848,972, filed Sep. 9, 2015, which claims the benefit of U.S. Provisional Application Ser. No. 62/047,766, filed Sep. 9, 2014.

FIELD OF INVENTION

The invention relates to development of drugs to treat metabolic syndrome targeting components of the complex pathophysiology.

BACKGROUND OF THE INVENTION

Metabolic diseases in general and Type II diabetes [(T2DM or T2D or Type II Diabetes or Non-insulin dependent mellitus (NIDDM)] in particular are a complex, multigene and multifactorial disease. Metabolic diseases such as hyperlipidemia, obesity and hypertension as well as environmental factors contribute to this disease. Cardiometabolic risk factor clusters (CMRFC) such as diabetes, hyperlipidemia, hypertension and overweight/obesity often cluster together in the same individual (Garber, A. J. et al. 2013). The prevalence of these risk factors is increasing significantly for all sociodemographic groups and it is putting an enormous economic burden on the society. Currently over one-fourth (over 70 million) of the U.S. population live with cardiovascular (CV) disease along with cardiometabolic risk factors. The economic impact of CV disease is enormous. In 2005, it was estimated to be over $242 B in direct medical expenses and over $152 B in indirect medical costs including lost productivity, resulting in a total estimated cost of $395 B in the U.S. alone (Sullivan, P. W. et al. 2007). CV disease is the leading cause of death resulting in an estimated 40% (>840,000) of all the deaths. Over 225 million people worldwide and over 26 million people in the USA alone suffer from Type II diabetes. In 2013, the annual cost of clinical management of this disease was over $245 B ($176 B for direct medical costs and $69 B in reduced productivity) (Statistics about diabetes, ADA, 2014). Type II diabetes was the seventh leading cause of death in the U.S. in 2010 (Mortality data, 2010, CDC). According to GB Research (Global Business Intelligence), the global Type II diabetes market will grow from $20.4 B in 2012 to $38.8 B in 2019. The U.S. market will more than double, from $12.7 B in 2012 to $27.2 B in 2019 (GBI Research, 2013). The world market for metabolic syndrome is estimated to be $72.4 B by 2018 (biovision.com).

Insulin resistance is a pathological hallmark of metabolic syndrome in general and Type II diabetes in particular. Type II diabetes continues to be an unmet medical need due to a number of factors including: the idiopathic nature of the disease, complex pathophysiology attributed to auto-immune and pro-inflammatory components, and comorbidities such as hyperlipidemia, obesity and high blood pressure (Erik, P. et al. 2009). Complexity of the disease contributes to manifestation of T2DM in multiple and diverse pathophysiological conditions such a way that the disease constitutes a unique pathophysiological phenomenon in each patient. Complexity of the disease in combination with unique metabolic profile and life style of each patient or group of patients contribute to lack of adequate efficacy with currently marketed Type II diabetes drugs (American College of Physicians, 2012). Moreover, Type II diabetes patients who are on current treatment regimens, continue to be vulnerable for complications such as diabetic retinopathy, skin ulcers, risk of coronary heart disease (CHD), stroke, chronic kidney disease (CKD), diabetic peripheral neuropathy, diabetic vasculopathy etc.

Type II diabetes continues to be an unmet medical need and at the current rate, it will double to over 640 million T2D patients world-wide by 2030 (American Diabetes Association). It is characterized by progressive deterioration of pancreatic beta cell dysfunction and insulin resistance. In spite of intense treatment with mono- and combination therapies with the existing modalities, patients suffer from progressive deterioration of metabolic control of glucose homeostasis (Standards of Medical Care in Diabetes, 2015). Lack of adequate glycemic control as indicated by inability to reach the target glycemic (A1c), blood pressure and cholesterol levels with currently marketed standards of medical care for Type II diabetes puts patients on a certain path to develop diabetes-related complications such as stroke, retinopathy, neuropathy, nephropathy, and skin ulcers. With the guidelines recommended by the American Association of Clinical Endocrinologists, 39-49% of patients do not meet targets for glycemic, blood pressure or cholesterol levels (Standards of Medical Care in Diabetes, 2015). It is needless to say that there's a desperate need for new modalities and innovation in the Type II diabetes space.

The complex etiology involves a combination of a variety of inflammation-triggered cellular dysfunctions that contribute individually and collectively to pancreatic cell dysfunction (Tateya, S. et al. 2013). Cyclooxygenase 2 or Cox-2 or COX-II is the predominant mediator of pro-inflammatory PGE2 synthesis in pancreatic islet cells (Robertson, R. P. 1998). ARKAY is advancing an innovative anti-inflammatory pancreatic beta cell-centric platform that treats islet cell dysfunction in combination with insulin resistance. It is well established that signaling pathways associated with immune dysregulation, chronic low-grade inflammation associated with obesity-triggered insulin resistance, and cardiovascular disease are intricately intertwined and they are literally inseparable from each other (Shu, C. J. et al. 2012).

Type II diabetes is characterized by impaired first phase of insulin secretion due to progressive deterioration of pancreatic beta cell function which compromises its inherent capacity to compensate for insulin resistance. Functional response of beta cells and insulin sensitivity of insulin-responsive tissues such as liver and skeletal muscle are tightly regulated by a feed-back loop. The magnitude of beta cell response is directly proportional to the tissue sensitivity of insulin-responsive tissues. This feedback loop determines the normal regulation of glucose metabolism and maintenance of glucose homeostasis. Beta cells have an inherent capacity to compensate with an increased output of insulin when insulin resistance is present. Blood glucose levels rise in the presence of insulin resistance when beta cells are incapable of releasing sufficient insulin due to progressive deterioration of beta cell function.

Activation of inducible Cyclooxygenase, Cox-2 or activation of constitutive Cox-2 plays a critically important role in the initiation of obesity-triggered inflammation. A link between elevation of blood glucose levels and activation of Cox-2 in pancreatic beta cells is well established. High glucose-induced PGE2 causes reduction in the beta cell mass by inhibiting its proliferation as well as induction of apoptosis of beta cells (Oshima, H. et al 2006). Indomethacin, a non-selective Cyclooxygenase inhibitor prevented HFD—(high fat diet)—induced obesity and insulin resistance in C57BL/6J mice (Fjaere E. et al. 2014). Treatment with NSAIDs (Non-steroidal anti-inflammatory drugs) such as Celecoxib and Salsalate have been shown to restore systemic insulin sensitivity in both translational preclinical models as well as in obese patients with T2DM (Goldfine, A. B. et al. 2013; Gonzalez-Ortiz, et al. 2005). High blood glucose activates Cox-2 in pancreatic beta cells and contributes to beta cell dysfunction. Treatment with NS-398 (a selective Cox-2 inhibitor) reverses beta cell dysfunction (Tian, V. F. et al. 2014) presumably by reducing PGE2-mediated beta cell apoptosis. Obesity-triggered inflammation due high blood sugar levels results in non-alcoholic hepatic steatosis which is a pathological hallmark of insulin resistance. Non-alcoholic steatohepatitis (NASH) is a condition that coexists with T2DM. Celecoxib reverses steatohepatitis as well as inflammation in HFD-induced Wistar rat NASH model (Chen, J. et al. 2011). Over-expression of NAG-1/GDF-15 (NSAIDs-activated gene-1) has been shown to improve glycemic parameters and prevent development of obesity by increasing thermogenesis, lipolysis and oxidative metabolism in obese C57BL/6J mice (Chrysovergis, K. et al. 2014). Activation of inducible form of Cox-2 plays a critically important role in the initiation of cellular dysfunctions including: adipocyte dysfunction, pancreatic beta islet cell dysfunction and macrophage dysfunction. Cellular dysfunctions contribute to development of insulin resistance and systemic glucose intolerance. Cox-2 deletion in C57BL/6J obese mice reduces blood glucose levels (Fujta et al. 2007). More importantly, in the same translational preclinical model, selective Cox-2 inhibitor, Celecoxib reduces HbA1c levels, improved glucose tolerance and elevated insulin levels (Fujita, H. et al. 2007). Selective Cox-2 inhibitors such as Celecoxib and Mesulid restore insulin sensitivity, reduce oxidative stress and reverse low-grade inflammation in male Sprague Dawley rats fed with High fructose diet or High fat diet (HFD) (Hsieh, P. et al. 2009; Liu, T. et al. 2009). They both reduced time-dependent increases in plasma insulin, 8-isoprostanes, leptin levels, and reversed increase in hepatic triglycerides. Celecoxib also restored insulin sensitivity in a small study of 12 obese patients (Gonzalez-Ortiz, et al. 2005).

Renin-Angiotensin system (RAS) exists in pancreatic beta cells and Angiotensin II is pro-inflammatory in pancreas and activates pro-inflammatory cytokine IL-1 beta. Ang II-mediated Islet cell inflammation triggers beta cell dysfunction contributing to Pancreatic beta cell exhaustion and decompensation (Sauter, N. et al. 2015). This occurs independent of vasoconstriction because sub-hypertensive dose of Valsartan (1 mg/Kg/day) improves impaired glucose tolerance with no effect on the systolic blood pressure in C57BL/6J obese mice. Blockade of Ang II with an ARB (Angiotensin receptor blocker) such as Valsartan improves glucose tolerance (Cole, B. K. et al. 2010) as well as restores not only beta cell dysfunction but also enhances blood flow as a result of vasodilation. The anti-hypertensive drug Metformin, which is considered the gold standard for the treatment of T2DM ameliorates not only HFD-induced insulin resistance but also improves glucose tolerance in C57BL/6J diet-induced obesity (DIO) model (Matsui, Y. et al. 2010; Woo, S. et al. 2014).

A number of publications have supported the importance of adipocytes and inflammation for the development of insulin resistance. For example, JNK-1 deficiency in adipocytes suppressed HFD—(High fat diet)—induced insulin resistance in the liver due to suppression of JNK-dependent suppression of IL-6 (Sabio, C. et al. 2008), adipocyte-specific deletion of Glut4 or over expression of MCP-1 results in systemic insulin resistance (Qi, L. et al. 2009), TNF-alpha deficiency improved insulin sensitivity in diet-induced obesity and in Lep ob/ob model of obesity and neutralization of TNF-alpha in obese fa/fa rats ameliorated insulin resistance (Hotamisiligil, G. S. et al. 1995). Elevated IL-1 beta, IL-6 and CRP are predictive of development of T2DM (Visser, M. et al. 1999) and TLR4 knock-out mice were protected from inflammation and insulin resistance (Shi, H. et al. 2006). Therefore, the lack of adequate efficacy and lack of adequate overall clinical benefit from currently marketed anti-hyperglycemic drugs is due to their inability to suppress the pro-inflammatory components of the complex pathophysiology of initiation and maintenance of systemic insulin resistance. TZDs and statins do have an inherent yet very modest anti-inflammatory capacity which contributes to their therapeutic efficacy. Therefore, suppression of obesity-triggered chronic low-grade inflammation with an anti-inflammatory drug such as Cox-2 selective inhibitor is anticipated to treat the impaired glucose homeostasis in T2DM patients by enhancing the efficacy of anti-hyperglycemic drugs with an additive or synergistic effect. Inhibition of inflammation is also anticipated to reduce the severity of diabetes-related complications.

Inflammation is a critical component of the pathophysiology of not only Type II diabetes but also the clinically relevant comorbidities as illustrated in FIG. 2. More importantly, pro-inflammatory signals contribute to initiation and maintenance of complications associated with Type II diabetes such as diabetic retinopathy, skin ulcers, risk of coronary heart disease (CHD), stroke, chronic kidney disease (CKD), diabetic peripheral neuropathy, diabetic vasculopathy etc. Pro-inflammatory signals determine the severity and duration of diabetes-related complications. An anti-inflammatory drug, Salsalate has been shown to reduce glycosylated hemoglobin A1c by an average of 0.37% in a clinical study conducted by Harvard Medical School (Goldfine, A. et al. 2013). There is a direct correlation between elevation in the pro-inflammatory biomarkers and impaired glucose metabolism. Statins and Thiazolidinediones (TZDs) reduce the risk of developing diabetes by consistently lowering the inflammatory markers (Deans K. A. and Sattar, N. (2006). Therefore, for efficient clinical management, it is important to treat cardiometabolic diseases including Type II diabetes not as an individual disease but as a metabolic syndrome with a complex pathophysiology with a strong pro-inflammatory component. For example, to achieve sufficient therapeutic efficacy in Type II diabetes patients who present wide-ranging challenges and metabolic profiles, it is indeed necessary to treat with a pro-inflammatory-centric combination of drugs that correct not only the impaired glucose homeostasis but also attenuate clinically relevant comorbidities and more importantly reduce the severity of diabetes-related complications. Instead of treating patients with metabolic syndrome as one homogeneous population with just one drug, it is necessary to treat patients with an anti-inflammatory drug in combination with anti-metabolic disease drugs with known efficacy and safety profile.

Patients stratified into groups for lack of adequate clinically favorable response to currently marketed drugs to treat metabolic diseases will be selected to test different Fixed Dose Combinations (FDC) formulations. Combination of drugs custom-formulated to provide therapeutic benefit to a specific stratified group of patients is anticipated to have therapeutic as well as kinetic synergy. More importantly these drugs would block the pro-inflammatory components of some of the comorbidities as well as attenuate the severity of complications such as Chronic kidney disease, diabetic neuropathy, diabetic nephelopathy, skin ulcers etc. Inclusion of an anti-inflammatory drug in every potential FDC formulation would result in enhancing therapeutic efficacy of Type II diabetes drugs by reducing therapeutic dose range such as minimal effective dose (MED), maximal tolerated dose (MTD) as well as the maintenance dose. Therefore, blockade of the pro-inflammatory components would contribute to sparing or reducing the severity or duration of some of the adverse side effects. Pro-inflammatory-centric anti-metabolic syndrome FDC formulations would result in the development of drugs that differentiate clinically as well as mechanistically from the currently available drugs.

The prevalence of prediabetes is 3 times more than that of Type II diabetes. American Diabetes Association reported that in 2012, there were 86 million Americans 20 or older had prediabetes (Statistics about diabetes, ADA, 2014). Insulin resistance as a result of failing pancreatic compensation due to excessive body weight or obesity, impaired glucose tolerance, impaired fasting glucose and symptomatic metabolic syndrome are the pathological hallmarks of prediabetes (American College of Physicians, 2012). Currently, there are no drugs that prevent or delay progression of prediabetes into insulin resistance or metabolic syndrome or incidence or new-onset T2DM.

Renin-Angiotensin System (RAS) exists in the pancreatic islets (Leung, P. S. 2012; Andraws, R. and D. L. Brown, 2007). Blockade of the RAS particularly with Angiotensin II receptor blockers (ARBs) and ACE (Angiotensin-converting enzyme) inhibitors has been shown to prevent the incidence or onset of Type II diabetes in patients with impaired glucose tolerance (IGT) (Van der Zijl, N. R. et al. 2011). Moreover, in normotensive patients with impaired glucose tolerance, ARBs increase glucose-dependent insulin secretion and enhance insulin sensitivity (McMurray, et al. 2010). Anti-inflammatory FDC formulations that combine anti-type II diabetes drugs with ARBs and ACE inhibitors will have tremendous therapeutic potential in terms of reducing the number of prediabetes patients who are on a certain path to positive clinical diagnosis for Type II diabetes.

It is hypothesized that in normotensive prediabetes and Type II diabetes, Anti-inflammatory FDC formulations that includes sub-therapeutic doses of ARBs and ACE inhibitors would enhance therapeutic efficacy of Type II diabetes drugs by reducing therapeutic dose range [minimal effective dose (MED), maximal tolerated dose (MTD) and the maintenance dose]. Therefore, blockade of the pro-inflammatory and RAS components would contribute to sparing or reducing the severity or duration of some of the adverse side effects associated with Type II diabetes drugs.

There is a continuing need for compounds, compositions, formulations and methods to treat metabolic syndrome.

OBJECTS AND SUMMARY OF THE INVENTION

It is an object of the invention to provide methods, compositions and formulations to treat Metabolic Syndrome or Insulin resistance syndrome.

It is a further object of the invention to provide broad-spectrum personalized drugs to treat metabolic syndrome including metabolic diseases such as Type II diabetes, hypertension, hyperlipidemia and obesity.

It is a further object of the invention to provide methods of treatment of not just the primary disease but also the comorbidities, risk factors and diabetes-related complications.

It is a further object of the invention to provide methods to treat prediabetes by preventing or delaying the new incidence or onset of Type II diabetes.

It is an object of the invention to provide an innovative method, composition and formulation to treat prediabetes and Type II diabetes in particular, and insulin resistance syndrome or metabolic syndrome in general.

It is an object of the invention to provide an innovative method of targeting multiple distinct yet overlapping mechanisms along the immune dysregulation-inflammation-insulin resistance axis to fill a gap that exists in the modalities that are used in the mono- and combination therapies that are used for the clinical management of Type II diabetes.

It is a further object of the invention to provide proof-of-concept (POC) of the anti-inflammatory pancreatic beta cell-centric approach for managing blood glucose (blood glucose) levels.

It is a further object of the invention to provide proof-of-concept of the anti-inflammatory pancreatic beta cell-centric approach for managing non-fasting (fed) and fasting blood glucose levels.

In accordance with the above objects and others, the present invention relates to the methods for treating patients with metabolic syndrome with personalized medicines. More particularly, the invention is directed in part to filling the gap that currently exists in the modalities used for the treatment of Type II diabetes by targeting multiple distinct yet overlapping mechanisms that contribute to pancreatic beta dysfunction along the immune dysregulation-inflammation-insulin resistance axis.

The invention is directed in part to a method of providing an orally-active anti-metabolic disease Fixed Dose Combinations (FDC) for use as personalized medicine to treat different components of the Metabolic Syndrome or Insulin resistance syndrome such as Type II diabetes, Hypertension, Hyperlipidemia and Obesity.

This Invention has the unique feature of personalized medicine with a custom formulation strategy to combine anti-metabolic and anti-cardiovascular disease drugs with anti-inflammatory drugs to reduce the pill burden and to achieve therapeutic as well as kinetic synergies resulting in better efficacy, safety and compliance. Formulation strategy described herein is aimed at providing patients and physicians better choice of drugs.

The invention is further directed to formulations and methods for treating metabolic syndrome, and in particular preventing or delaying the onset of Type II diabetes via an innovative anti-inflammatory pancreatic beta cell-centric platform that treats islet cell dysfunction in combination with insulin resistance. The invention is further directed in part to the inclusion of an orally-active anti-inflammatory drug as part of the composition of the drug FDC. Treating the underlying inflammatory component of the complex pathophysiology of Type II diabetes with an anti-inflammatory-centric therapy represents a new shift in the paradigm of clinically managing T2DM efficiently.

The invention is further directed in part to the inclusion of an orally-active anti-inflammatory drug, at least one anti-diabetic drug and blockers of Renin-Angiotensin System (RAS) as part of the composition of the FDC to prevent the incidence or delay the onset of Type II diabetes.

The invention is also directed in part to formulations and methods in which one or more orally-active anti-inflammatory drugs will be combined with the orally-active anti-metabolic disease drugs in FDC ratios to achieve therapeutic as well as the kinetic synergy.

In certain embodiments, the invention is further directed in part to the use of more than one and as many as five (or more) orally-active anti-metabolic and anti-inflammatory FDC.

Certain embodiments of the invention are directed to the delivery of FDC of orally-active anti-inflammatory drugs and anti-metabolic disease drugs as a multi-layer matrix of immediate release (IR) and extended release (ER) formulations. In certain embodiments of the invention, the delivery of FDC of orally-active anti-inflammatory drugs and anti-metabolic disease drugs is accomplished via a delayed release (DR) formulation. In certain preferred embodiments of the invention, the pharmaceutical formulations of the invention utilize a combination of immediate release, extended release and/or delayed release for the orally-active anti-inflammatory drugs and anti-metabolic disease drugs included in the FDC formulation.

Further embodiments of the invention are directed in part to the delivery of FDC of orally-active anti-inflammatory drugs and anti-metabolic disease drugs as a multi-layer matrix of IR and DR formulations along with one or more drug administered parentarally (intravenous, subcutaneous, intramuscular or intramedullary injection).

Further embodiments of the invention are directed in part to the delivery of FDC of orally-active anti-inflammatory drugs and anti-metabolic disease drugs as a multi-layer matrix of IR and DR formulations along with one or more drug administered transdermally or nasally.

In certain embodiments, the invention is directed in part to the treatment with an anti-inflammatory-centric FDC to treat Type II diabetes component of metabolic syndrome or insulin-resistant syndrome to patients in need of said therapy.

The invention is further directed in part to treatment with an anti-inflammatory-centric FDC to treat hypertension or high blood pressure component of metabolic syndrome or insulin-resistant syndrome.

The invention is further directed in part to treatment with an anti-inflammatory-centric FDC to treat hyperlipidemia component of metabolic syndrome or insulin-resistant syndrome.

The invention is further directed to treatment with an anti-inflammatory-centric FDC to treat excessive bodyweight or obesity component of metabolic syndrome or insulin-resistant syndrome.

The invention is further directed in part to a pharmaceutical formulation of FDC of drugs to treat metabolic syndrome or insulin-resistant syndrome in the form of multi-layered monolithic tablets.

The invention is further directed in part to a pharmaceutical formulation of FDC of drugs to treat metabolic syndrome insulin-resistant syndrome in the form of core tablet-in-tablet or multi-disc tablets.

The invention is further directed in part to a pharmaceutical formulation of FDC of drugs to treat metabolic syndrome insulin-resistant syndrome in the form of beads inside a capsule.

The invention is further directed in part to the use of more than one and as many as five (or more) orally-active drug FDC of IR, IR and DR, and IR and ER formulations for preventing or slowing down prediabetes in the form of multi-layered monolithic tablet or core tablet-in-tablet/multi-disc tablets or beads inside a capsule or tablets inside a capsule.

In certain preferred embodiments, the present invention is directed in part to pharmaceutical formulation for the treatment of metabolic syndrome comprising a therapeutically effective amount(s) of an active agent selected from the group consisting of at least one anti-diabetic drug; or a therapeutically effective amount of at least one anti-hypertensive drug; or a therapeutically effective amount of at least one anti-obesity drug; or a therapeutically effective amount of at least one drug for the treatment of hyperlipidemia; or a combination of any of the foregoing; and a therapeutically effective amount of at least one orally active anti-inflammatory drug. In certain preferred embodiments, the pharmaceutical formulation comprises a therapeutically effective amount(s) of a drug selected from the group consisting of at least one anti-diabetic drug, an anti-hypertensive drug, and a therapeutically effective amount of at least one orally active anti-inflammatory drug.

In certain preferred embodiments, the pharmaceutical formulation of the invention comprises therapeutically effective amounts of at least two drugs selected from the group consisting of at least one an anti-hypertensive drug, at least one anti-diabetic drug, at least one drug for the treatment of hyperlipidemia, at least one anti-obesity drug, and at least one anti-inflammatory drug. In certain embodiments, the pharmaceutical formulation of the invention comprises therapeutically effective amounts of a drug in at least three, at least four or at least five of the afore-mentioned drug classes. In certain preferred embodiments, the pharmaceutical formulation of the invention comprises therapeutically effective amounts of at least one an anti-hypertensive drug, at least one anti-diabetic drug, at least one anti-obesity drug, and at least one anti-inflammatory drug. In certain preferred embodiments, the pharmaceutical formulation of the invention comprises therapeutically effective amounts of at least one an anti-hypertensive drug, at least one anti-diabetic drug, at least one drug for the treatment of hyperlipidemia, at least one anti-obesity drug, and at least one anti-inflammatory drug.

In certain preferred embodiments, the pharmaceutical formulation of the invention includes an anti-hypertensive drug that is a blocker of Renin-Angiotensin System (RAS).

In certain preferred embodiments in which the metabolic syndrome is Type II diabetes, the pharmaceutical formulation comprises therapeutically effective amounts of a combination of one or more anti-inflammatory drug(s) and at least one drug used in the treatment of Type II Diabetes. In certain of such embodiments, the pharmaceutical formulation further comprises a drug that is a blocker of Renin-Angiotensin System (RAS).

In certain preferred embodiments in which the metabolic syndrome is hyperlipidemia, the pharmaceutical formulation of the invention comprises therapeutically effective amounts of a combination of one or more anti-inflammatory drug(s) and one or more drugs selected from the group consisting of a statin, niacin, a fibrate, and combinations of any of the foregoing.

In certain preferred embodiments in which the metabolic syndrome involves obesity, the pharmaceutical formulation of the invention comprises therapeutically effective amounts of a combination of one or more anti-inflammatory drug(s) and one or more drugs selected from the group consisting of an anti-obesity drug, an anti-diabetic drug, and combinations of any of the foregoing. In certain preferred embodiments, the pharmaceutical formulation for the treatment of obesity further comprises a drug for the treatment of hyperlipidemia and/or hypertension.

In certain preferred embodiments in which the metabolic syndrome involves hypertension, the pharmaceutical formulation of claim 1 comprises therapeutically effective amounts of one or more drugs selected from the group consisting of a beta blocker, a diuretic, an ACE inhibitor, an Angiotension II Type 1 Receptor Blocker (ARBs), Calcium channel blocker (CCBs), a central agonist, a peripheral-acting adrenergic blocker, a direct vasodilator, a direct renin inhibitor, and combinations of any of the foregoing; and at least one anti-inflammatory drug. In certain preferred embodiments, the pharmaceutical formulation of the invention for the treatment of metabolic syndrome that involves hypertension further comprises therapeutically effective amounts of one or more drugs selected from the group consisting of an anti-obesity drug, an anti-diabetic drug, a drug for the treatment of hyperlipidemia, and combinations of any of the foregoing.

The pharmaceutical formulation may be any that is known to those skilled in the art and useful to administer the drugs in the FDC. In certain preferred embodiments, the pharmaceutical formulation is an oral solid dosage form. In other preferred embodiments, the pharmaceutical formulation is an injectable formulation which is administered parenterally (intravenous, subcutaneous, intramuscular, or intramedullary injection). In yet other embodiments of the invention, the pharmaceutical formulation is administered transdermally or nasally. The pharmaceutically formulation of claim 1, which is in liquid form.

In certain preferred embodiments which include an antidiabetic drug(s), the anti-inflammatory drug and the antidiabetic drug(s) are in immediate release form. In other preferred embodiments, at least one of the drugs is in controlled or delayed release form.

The invention is further directed in part to a method of treating metabolic syndrome, comprising administering to a human patient having a condition selected from the group consisting of Type II diabetes, Hypertension, Hyperlipidemia and Obesity, a pharmaceutical formulation for the treatment of metabolic syndrome comprising a therapeutically effective amount(s) of a drug selected from the group consisting of at least one anti-diabetic drug; or a therapeutically effective amount of at least one anti-hypertensive drug; or a therapeutically effective amount of at least one anti-obesity drug; or a therapeutically effective amount of at least one drug for the treatment of hyperlipidemia; or a combination of any of foregoing; and a therapeutically effective amount of at least one orally active anti-inflammatory drug. In certain embodiments wherein the patient is diabetic or prediabetic, the method further comprises administering a therapeutically effective amount(s) of a drug selected from the group consisting of at least one anti-diabetic drug, a blocker of Renin-Angiotensin System (RAS), and a combination of the foregoing, together with a therapeutically effective amount of at least one orally active anti-inflammatory drug. In further preferred embodiments wherein the metabolic disease involves hypertension, the method further comprises the administration of one or more of an ACE inhibitor, an angiotension II receptor Type 1 blocker (ARBs), a DPPIV inhibitor, at least one anti-diabetic drug, a blocker of Renin-Angiotensin System (RAS), together with a therapeutically effective amount of at least one orally active anti-inflammatory drug, to the patient.

It is comtemplated that all of the methods of the present invention encompass the chronic treatment of the metabolic condition(s). Thus, in preferred embodiments, the drugs (e.g., antidiabetic, antihypertensive, anti-obesity, drug for hyperlipidemia; together with an anti-inflammatory drug) are administered to the patient on a chronic basis. In certain preferred embodiments, these drugs are administered as personalized medicines to clinically manage Type II diabetes or prediabetes in stratified groups of human patients based on their cardiometabolic risk factor profiles. In further preferred embodiments, the drugs are administered as personalized medicines to clinically manage Type II diabetes or prediabetes groups of patients stratified for lack of adequate therapeutic efficacy with prior treatments.

In embodiments in which the metabolic syndrome involves Type II diabetes, in certain embodiments the method further comprises concomitantly administering insulin to the patient to achieve better blood glucose control. In certain of such preferred embodiments, dosage is adjusted on the basis of glucose measurements.

The invention is further directed in part to the use of more than one and as many as five orally-active drug FDC of IR, IR and DR and IR and ER formulations for other therapeutic areas.

This invention relates to the pro-inflammatory component of the complex pathophysiology (FIG. 3) as well as the cardiometabolic risk factor clusters (CMRFC) and/or comorbidities of the metabolic syndrome.

This invention relates in part to the Renin-Angiotensin system (RAS) that exists in the pancreatic islets.

This invention describes the overall clinical benefits of blocking the pro-inflammatory components and the RAS in combination with currently marketed drugs that are used to treat Type II diabetes, Hypertension, Hyperlipidemia and Obesity.

This invention describes the overall clinical benefits of blocking the pro-inflammatory components and the RAS in combination with drugs that will be discovered and developed in the future to treat Type II diabetes, Hypertension, Hyperlipidemia and Obesity.

Inflammation and RAS are critical components of the development of insulin resistance which is a pathological hallmark of Type II diabetes as well as the metabolic syndrome. This invention describes customized unique formulation strategies that combine anti-metabolic disease drugs with anti-inflammatory drugs and/or blockers of RAS in the form of Immediate release (IR) or Quick Release (QR) and Extended release (ER)/Sustained release (SR)/Controlled release (CR) and Delayed release (DR) depending on the needs of the individual patient or group of patients.

In certain embodiments of the invention, Fixed Dose combinations (FDC) of drugs may contain blockers or activators of therapeutic targets relevant for treating metabolic diseases and the inflammatory component of the pathophysiology.

In certain embodiments of the invention, FDC formulation of drugs will be prepared in fixed dose ratios to achieve the intended therapeutic efficacy for preventing the incidence of (prophylactic) or delay the progression of prediabetes into insulin resistance syndrome or metabolic syndrome.

In certain embodiments of the invention, FDC of drugs will be prepared in fixed dose ratios to achieve the intended (e.g. anti-type II diabetes, anti-hypertensive, lipid lowering and anti-obesity or a combination of thereof) therapeutic efficacy.

In certain embodiments of the invention, depending on the cardiometabolic risk factor profiles of stratified patients, the FDC of drugs will be prepared in fixed dose ratios of two drug combinations (e.g. anti-inflammatory and anti-Type II diabetic, anti-inflammatory and lipid lowering or anti-inflammatory and anti-hypertensive or anti-inflammatory and anti-obesity) or three drug combinations (e.g. Anti-inflammatory, Anti-Type II diabetic, Anti-hypertensive or Anti-inflammatory, Anti-Type II diabetic, Lipid lowering or Anti-inflammatory, Anti-Type II diabetic, Anti-obesity or Anti-inflammatory, Anti-hypertensive, Lipid lowering or Anti-inflammatory, Anti-obesity, Anti-hypertensive or Anti-inflammatory, Lipid lowering, Anti-obesity) or four drug combinations (e.g. Anti-inflammatory, Anti-Type II diabetic, Lipid lowering, Anti-hypertensive or Anti-inflammatory, Anti-Type II diabetic, Lipid lowering, Anti-obesity or five drug combinations (e.g. Anti-inflammatory, Anti-Type II diabetic, Lipid lowering, Anti-hypertensive, Anti-obesity) to achieve the intended therapeutic efficacy. In certain embodiments, the FDC of drugs will be prepared in fix dose ratios of more than five drug combinations.

In certain embodiments of the invention, the FDC of drugs will be prepared in fixed dose ratios of two drug combinations of two, three, four and five drug combinations includes an anti-diabetic injectable.

In certain embodiments of the invention, drugs will be formulated with the same drug as FDC of IR and ER.

In certain embodiments of the invention, FDC of drugs will be formulated to contain the same drug in the form of IR and DR.

In certain embodiments of the invention, FDC of drugs will be formulated to contain IR and DR of the same drug along with ER of a second drug.

In certain embodiments of the invention, FDC of drugs will be formulated to contain IR and ER of the same drug along with the IR of a second drug.

In certain embodiments of the invention, FDC of drugs will be formulated to contain IR of one drug, ER of a second and a third drug and IR of a fourth drug.

In certain embodiments of the invention, combination of drugs will be made as a monolithic FDC tablet composed of two or more active formulations mixed and compressed in a single layer tablet.

In certain embodiments of the invention, FDC of drugs will be prepared either in the form of a multi-layered monolithic tablet.

In certain embodiments of the invention, FDC of drugs will be prepared either in the form of a multi-layered monolithic tablet inside a tablet.

In certain embodiments of the invention, FDC of drugs will be prepared either in the form of a core tablet-in-tablet or multi-layered multi-disk tablet (MLMDT) consisting of a tablet core formulation surrounded by a second outer formulation.

In certain embodiments of the invention, FDC of drugs will be prepared in the form of beads inside a capsule. Each bead would represent different color and coating level depending on the kinetics of drug release. For example, some beads would release drugs immediately (IR). Some would beads would release for an extended period of time (ER), while some after a long while (DR).

In certain embodiments of the invention, FDC of drugs will be prepared either in the form of mini tablets inside a capsule. Uniquely color-coded capsules represent customized formulations that contain a unique combination of drugs with predetermined modified release kinetics. Colors and shapes of tablets represent individual drugs (either same or different) and coating level depending on the kinetics of modified drug release. For example, white colored tablet is released immediately (IR or QR), red colored tablet is released for an extended period of time (ER or SR or XR) and light green tablet is released after a long delay (DR).

In certain embodiments of the invention, FDC of drugs will be prepared in liquid formulations.

In certain embodiments of the invention, the FDC formulation comprises therapeutically effective amounts of a combination of an anti-inflammatory drug(s) and one or more drugs which are used in the treatment of Type II Diabetes drugs. The drugs can be in immediate release form, or they can be in controlled (used synonymously herein with sustained or extended) release form. In yet other embodiments one or more of the drugs can be in immediate release form and the other(s) in controlled or delayed release form. In certain embodiments of the invention, the FDC formulation comprises a combination of an anti-inflammatory drug and two drugs which are used in the treatment of Type II Diabetes. For example, anti-diabetic drugs may be chosen from one or more of a sulfonylurea, a biguanide (e.g., metformin and the like), a DPP-IV inhibitor, an SGLT-2 inhibitor, and/or an incretin mimetic. In preferred embodiments, an anti-inflammatory drug is included in the FDC formulation.

In certain embodiments of the invention, the FDC formulation comprises therapeutically effective amounts a combination including one or more lipid lowering drugs. The drugs can be in immediate release form, or they can be in controlled (used synonymously herein with sustained or extended) release form. In yet other embodiments one or more of the drugs can be in immediate release form and the other(s) in controlled release form. In certain embodiments of the invention, the FDC formulation comprises a combination of at least two of an anti-inflammatory drug, a statin and niacin. In certain other embodiments of the invention, the FDC formulation comprises a combination of at least two of an anti-inflammatory drug, a statin, niacin and a fibrate. In certain other embodiments of the invention, the FDC formulation comprises a combination of at least two of an anti-inflammatory drug, a statin, a fibrate and niacin. These drugs can be in controlled (used synonymously herein with sustained or extended) release form one or more of the drugs can be in immediate release form and the other(s) in controlled or delayed release form. In preferred embodiments, an anti-inflammatory drug is included in the FDC formulation.

In certain embodiments of the invention, the FDC formulation comprises therapeutically effective amounts of a combination including one or more anti-hypertensive drugs. The drugs can be in immediate release form, or they can be in controlled (used synonymously herein with sustained or extended) or delayed release form. In yet other embodiments one or more of the drugs can be in immediate release form and the other(s) in controlled or delayed release form. In certain embodiments of the invention, the FDC formulation comprises a combination of a diuretic and a beta blocker. In certain other embodiments of the invention, the FDC formulation comprises a combination of at least two of an anti-inflammatory drug, a beta blocker, a diuretic, an ACE inhibitor, an Angiotension II Receptor Blocker (ARBs), Calcium channel blocker (CCBs), a central agonist, a peripheral-acting adrenergic blocker, a direct vasodilator, or a direct renin inhibitor. These drugs can be in controlled (used synonymously herein with sustained or extended) or delayed release form and one or more of the drugs can be in immediate release form and the other(s) in controlled release form. In preferred embodiments, an anti-inflammatory drug is included in the FDC formulation.

In certain embodiments of the invention, the FDC formulation comprises therapeutically effective amounts a combination including one or more anti-obesity drugs. The drugs can be in immediate release form, or they can be in controlled (used synonymously herein with sustained or extended) or delayed release form. In yet other embodiments one or more of the drugs can be in immediate release form and the other(s) in controlled or delayed release form. In certain other embodiments of the invention, the FDC formulation comprises a combination of at least two of an anti-inflammatory drug, an anti-obesity drug, a DPPIV inhibitor, and an incretin mimetic. These drugs can be in controlled (used synonymously herein with sustained or extended) or delayed release form and one or more of the drugs can be in immediate release form and the other(s) in controlled release form. In preferred embodiments, an anti-inflammatory drug is included in the FDC formulation.

In certain embodiments of the invention, the FDC formulation comprises therapeutically effective amounts a combination including one or more drugs for prediabetes or the prevention of onset of Type II diabetes. The drugs can be in immediate release form, or they can be in controlled (used synonymously herein with sustained or extended) or delayed release form. In yet other embodiments one or more of the drugs can be in immediate release form and the other(s) in controlled or delayed release form. In certain other embodiments of the invention, the FDC formulation comprises a combination of at least two of an anti-inflammatory drug, an ACE inhibitor, an angiotension II receptor blocker (ARBs), and an antidiabetic drug as previously described above. These drugs can be in controlled (used synonymously herein with sustained or extended) or delayed release form and one or more of the drugs can be in immediate release form and the other(s) in controlled release form. In certain preferred embodiments, the FDC formulation includes an anti-diabetic in both immediate release and delayed release form (e.g., a biguanide such as metformin). In preferred embodiments, an anti-inflammatory drug is included in the FDC formulation.

In certain embodiments of the invention, the FDC formulation comprises therapeutically effective amounts a combination including one or more drugs for the treatment of metabolic syndrome. The drugs can be in immediate release form, or they can be in controlled (used synonymously herein with sustained or extended) or delayed release form. In yet other embodiments one or more of the drugs can be in immediate release form and the other(s) in controlled or delayed release form. In certain other embodiments of the invention, the FDC formulation comprises a combination of at least two of (and preferably at least three of or all of the following) an anti-inflammatory drug, an ACE inhibitor, an angiotension II receptor blocker (ARBs), and a DPPIV inhibitor. These drugs can be in controlled (used synonymously herein with sustained or extended) or delayed release form and one or more of the drugs can be in immediate release form and the other(s) in controlled release form. In preferred embodiments, an anti-inflammatory drug is included in the FDC formulation.

In certain embodiments of the invention, the FDC formulation comprises therapeutically effective amounts of Type II diabetes drugs such as older shorter-acting sulfonyl ureas such as Dymelor (acetohexamide, 50 mg to 500 mg), Diabenese (chloropropamide, 100 mg to 500 mg), Orininase (tolbutamide, 250 to 500 mg), Tolinase (Tolazamide, 100 to 250 mg) or newer sulfonylureas such as Glucotrol (Glipizide, 2.5 mg to 30 mg), Glucotrol XL (2.5 mg to 100 mg), DiaBeta (glyburide, 1.25 mg to 20 mg), Micronase (1.25 mg to 20 mg), Glynase (glyburide/Glibenclamide, 0.75 mg to 12 mg), Glynase PresTab (glyburide, 0.75 mg to 12 mg), Amaryl (glimepiride, 1 mg to 8 mg) or biguanides such as Metformin (Glucophage, Glucophage XR, Riomet, Fortamet and Glumetza, 250 mg to 2550 mg) or Thiozolidinediones (TZDs) such as Actos (pioglitazone, 5 mg to 30 mg) Avandia (rosiglitazone, 2 mg to 8 mg), or Alpha glucosicase inhibitors such as Precose (acarbose, 25 mg to 100 mg), Glyset (miglitol, 25 mg to 100 mg) or Dipeptidyl peptidase inhibitors (DPPIV) such as Januvia (sitagliptin, 10 mg to 100 mg), Nesina (alogliptin, 2.5 mg to 25 mg), Onglyza (linagliptin, 2.5 mg) or incretin mimetic such as Repaglinide (Prandin, 2.5 ug to 10 ug), Nateglinide (Starlix, 2.5 ug to 10 ug), Exenatide (Byetta, Bydureon, 2.5 ug to 10 ug), Liraglutide (Victoza, 0.25 mg to 1.8 mg) or Sodium Glucose co-transporters (SGLT-2) inhibitors such as Farxiga (dapagliflozin, 2.5 mg to 10 mg) and Invokana (canagliflozin, 50 mg to 100 mg).

In certain embodiments of the invention, the FDC formulation comprises therapeutically effective amounts of high cholesterol/lipid lowering drugs such as Atorvastatin (Lipitor, 5 mg to 80 mg), Fluvastatin (Lescol, 10 mg to 80 mg), Lovastatin (Mevacor, 5 mg to 80 mg), Provastatin (Pravachol, 20 mg to 80 mg), Rosuvastatin (Crestor, 2.5 mg to 40 mg), Simvastatin (Zocor, 2.5 mg to 40 mg) or Nicotinic acid such as Nicolar (250 mg to 500 mg), Niaspan (250 mg to 2000 mg) or Bile acid resins (sequestrants) such as Questran (4.5 g to 9 g) and Questran Light (2.5 g to 24 g), Colestid (1 g to 16 g), Welchol (1 g to 3.75 g) or Fibrates such as Atromid (20 mg to 145 mg), Tricor (24 mg to 145 mg), Lopid (500 mg to 1200 mg), Ezetimide (Zetia, 2.5 mg to 10 mg).

In certain embodiments of the invention, the FDC formulation comprises therapeutically effective amounts of anti-inflammatory drugs such as Celebrex (Celecoxib, 25 mg to 200 mg), Advil, Motrin (Ibuprofen, 100 mg to 3200 mg), Aleve (Naproxen, sodium, 100 mg 1650 mg), Ascriptin (200 mg to 325 mg), Ecotrin (50 mg to 325 mg), Asprin (81 mg to 325 mg), Anaprox (Naproxen Sodium, 100 mg to 1650 mg), Clinoril (Sulindac, 100 mg to 400 mg), DayProv (Oxaprozin, 500 mg to 1200 mg), Disalcid (Salsalate, 500 mg to 3 g), Dolobid (Difflumisal, 250 mg to 750 mg), Feldene (Piroxieum, 5 mg to 20 mg), Indocin (Indomethacin, 25 mg to 100 mg), Lodine (Etodolac, 100 mg to 500 mg), Mobic (Meloxicam, 5 mg to 20 mg), Naprosyn (Naproxen, 100 mg to 1650 mg), Relafen (Nabumetone, 500 mg to 2000 mg), Toradol (Ketorolactromethamine, 10 to 40 mg), Vimovo (Naproxen/esomeprazole, 375 mg/20 mg), Voltaren (Diclofenac, 50 mg 100 mg), Xeljanz (Tofactinib Citrate, 2.5 mg to 5 mg), Anakinra (Anti-IL6 Ab, 50 mg to 100 mg), Humira (Anti-TNF-alpha Ab, 5 mg 10 mg).

In certain embodiments of the invention, the FDC formulation comprises therapeutically effective amounts of anti-hypertensive drugs such as Diuretics (Aldactone (Spiranolactone, 25 mg to 400 mg), Dyrenium (Triampeterene, 50 mg to 100 mg), Esidix, Hydrodiuril & Microzide (Hydrochlorothiazide or HCTZ, 12.5 mg to 100 mg), Hygroton & Thalitone (Chlorthalidone, 10 mg to 100 mg), Lasix (Furosemide, 10 mg to 600 mg), Lozol (Amiloride hydrochloride, 1.25 mg to 5 mg), Mykrox (0.5 mg) and Zaroxylyn (2.5 mg) (Metolazone) or Beta blockers (Blocadren (Timolol, 5 mg to 60 mg), Cartrol (Cartelol Hydrochloride, 1.25 mg to 10 mg), Coreg (Corredilol, 3.125 mg to 50 mg), Coregard (Nadolol, 20 mg to 160 mg), Inderal (Propranolol, 20 mg 640 mg), Kerlone (Betaxolol, 5 mg to 40 mg), Levatol (Penbutolol Sulfate, 10 mg to 80 mg), Lopressor & Toprol XL (Metoprolol, 50 mg to 450 mg), Sectral (Acebutolol, 200 mg to 1200 mg), Tenormin (Atenolol, 25 mg to 200 mg), Visken (Pindolol, 2.5 mg 60 mg), Zebeta (Bisprolol fumarate, 1.25 mg to 20 mg), Normodyne and Trandate (Labetolol, 50 mg to 2400 mg) or Alpha blockers (Cardura (Doxazocin, 1 mg to 16 mg), Hytrin (Terazocin, 1 mg to 20 mg), Minipress (Prazocin, 1 mg to 20 mg) or Angiotensin-converting enzyme inhibitors: Accupril (Quinapril, 5 mg to 80 mg), Altace (Ramipril, 2.5 mg to 20 mg), Capoten (Captopril, 25 mg to 450 mg), Mavik (Trandolapril, 1 mg to 8 mg), Lotensin (Benazepril, 5 mg to 40 mg), Monopril (Fosinopril, 5 mg to 80 mg), Prinvil & Zestril (Lisinopril, 5 mg to 80 mg), Univasc (moexipril, 5 mg to 60 mg), Vasotec (Enalapril, 2.5 mg to 40 mg) or Angiotensin receptor type 1 blockers: Atacand (Candesartan, 4 mg to 32 mg), Avapro (Irbesartan, 75 mg to 300 mg), Benicar (Olmesartan, 10 mg to 40 mg), Cozaar (Losartan, 25 mg to 100 mg), Diovan (Valsartan, 40 mg to 320 mg), Micardis (Telmisartan, 20 mg to 80 mg), Teveten (Eprosartan, 400 mg to 800 mg) or Calcium channel blockers, Adalat and Procardia (Nifedipine, 10 mg to 60 mg), Calan, Covera, Isoptin, Verelan, and others (Verapamil, 120 mg to 300 mg), Cardene (Nicardipine, 20 mg to 60 mg), Cardizem Cartia, Dilacor, and Tiazac (Diltiazem, 5 mg to 420 mg), DynaCirc (Isradipine, 2.5 mg to 10 mg), Plendil (Felodipine, 2.5 mg to 10 mg), Norvasc (Amlodipine, 2.5 mg to 10 mg), Sular (Nisoldipine, 5 mg to 60 mg) or Central agonists: Aldomet (Methyldopa, 250 to 500 mg), Catapres (Clonidine, 0.1 mg to 2.4 mg), Tenex (Guanfacine, 1 mg to 3 mg), Wytensin (Guanabenz, 2 mg to 32 mg) or Peripheral-acting adrenergic blockers: Hylorel (Guanadrel, 5 mg to 75 mg), Ismelin (Guanethidine, 5 mg to 50 mg), Serpasil (Reserpine, 0.1 mg to 0.5 mg) or Direct vasodilators: Loniten (Minoxidil, 2.5 mg to 100 mg), Apresoline (Hydralazine, 5 mg to 300 mg) or Direct renin inhibitors (Tekturana (Aliskiren, 75 mg to 300 mg).

In certain embodiments of the invention, the FDC formulation comprises therapeutically effective amounts of Anti-Obesity drugs such as Orlistat (Xenical, 60 mg to 120 mg), Orlistat (Alli) OTC (30 mg to 60 mg), Phentermine (15 mg to 37.5 mg) Lorcaserin (Belviq, 5 mg to 10 mg), Phentermine/Topimerate (Qsymia, 3.75 mg/23 mg to 7.5 mg/46 mg).

The invention is further directed to a pharmaceutical formulation comprising a therapeutically effective amount of a Type II diabetes drug, an anti-inflammatory drug, and an angiotensin II type 1 receptor blocker. In certain preferred embodiments, the dose of one or more of the Type II diabetes drug, an anti-inflammatory drug, and an angiotensin II type 1 receptor blocker are sub-therapeutic. In certain preferred embodiments, the angiotensin II type 1 receptor blocker increases insulin sensitivity. In certain preferred embodiments, the Type II diabetes drug is a biguanide drug. In certain preferred embodiments, the angiotensin II type 1 receptor blocker is valsartan. In certain preferred embodiments, the anti-inflammatory drug has COX-2 inhibitor properties. In further preferred embodiments, a unit dose of the formulation comprises from about 50 mg to about 400 mg celexoxib, from about 250 mg to about 2000 mg metformin, and from about 40 mg to about 320 mg valsartan. In certain preferred embodiments, the unit dose is a fixed unit dose that is orally administered to human patients on a chronic basis. In certain preferred embodiments, the dose of celexocib and/or the dose of valsartan is sub-therapeutic.

In further preferred embodiments, the invention is directed in part to a pharmaceutical formulation comprising a therapeutically effective amount of an anti-diabetic drug(s), a therapeutic or sub-therapeutic amount of a pharmaceutically acceptable COX-2 inhibitor, and a therapeutic or sub-therapeutic amount of valsartan. In certain preferred embodiments, the anti-diabetic drug is metformin. In certain preferred embodiments, the COX-2 inhibitor is celecoxib. In certain preferred embodiments, the dose of metformin is sub-therapeutic. In certain preferred embodiments, the dose of celecoxib is sub-therapeutic. In certain embodiments, the dose of metformin and the dose of celecoxib are both sub-therapeutic. In such embodiments, the dose of metformin may be, e.g., less than about 500 mg and the dose of celecoxib may be, e.g., less than about 80 mg.

The invention is further directed in part to a method of treating a diabetic or pre-diabetic condition in a mammal, comprising orally administering a fixed dose combination comprising a biguanide, a non-steroidal anti-inflammatory, and an Angiotensin II Type 1 receptor blocker on a chronic basis. In certain preferred embodiments, the dose of the non-steroidal anti-inflammatory drug and/or the dose of the Angiotensin II Type 1 receptor blocker is sub-therapeutic. In certain preferred embodiments, the biguanide is metformin and the Angiotension II Type 1 receptor 1 receptor blocker is valsartan. In certain preferred embodiments, the administration of the fixed dose combination improves non-fasting blood glucose levels in less than one hour post-administration and fasting blood glucose levels in less than 15 minutes after the oral glucose load in the Oral Glucose Tolerance Test (OGTT).

In certain preferred embodiments, the invention is directed in part to a pharmaceutical formulation comprising a combination of an anti-inflammatory drug (e.g., celecoxib) together with a biguanide, both in immediate release form. In other embodiments, the invention is directed in part to a pharmaceutical formulation comprising a combination of an anti-inflammatory drug (e.g., celecoxib) together with a biguanide, wherein the anti-inflammatory drug is in immediate release form and the biguanide drug is in an extended release form. Yet other embodiments of the invention are directed in part to a pharmaceutical formulation comprising a combination of an anti-inflammatory drug (e.g., celecoxib) together with a biguanide, wherein the anti-inflammatory drug is in immediate release form and a portion of the biguanide drug is in immediate release form and the other portion of the biguanide drug is in an extended release form. Yet other embodiments of the invention are directed in part to a pharmaceutical formulation comprising a combination of an anti-inflammatory drug (e.g., celecoxib) together with a biguanide, wherein the anti-inflammatory drug is in immediate release form and a portion of the biguanide drug is in immediate release form, a portion of the biguanide drug is in an extended release form, and the remaining portion of the biguanide drug is in delayed release form.

In certain preferred embodiments, the invention is directed in part to a pharmaceutical formulation comprising a combination of an anti-inflammatory drug (e.g., celecoxib) together with an ARB (e.g., valsartan), wherein the anti-inflammatory drug is in immediate release form and the ARB is in delayed release form. In certain other embodiments, the invention is directed in part to a pharmaceuticl formulation comprising a combination of an anti-inflammatory drug (e.g., celecoxib) together with an ARB (e.g., valsartan), wherein the anti-inflammatory drug is in immediate release form and the ARB is in extended release form.

Further preferred embodiments of the invention are directed in part to a pharmaceutical formulation comprising a combination of an anti-inflammatory drug (e.g., celecoxib), a biguanide drug (e.g., metformin), and an ARB (e.g., valsartan). In certain embodiments, the anti-inflammatory drug is in immediate release form, the biguanide is in immediate release form, and the ARB is in delayed release form. In other embodiments, the anti-inflammatory drug is in immediate release form, the biguanide is in extended release form, and the ARB is in delayed release form. In yet other embodiments, the anti-inflammatory drug is in immediate release form, a portion of the biguanide is in extended release and the other portion of the biguanide is in delayed release form, and the ARB is in delayed release form. In yet other embodiments, the anti-inflammatory drug is in delayed release form, the biguanide is in immediate release form, and the ARB is in immediate release form. In yet other embodiments, a portion of the anti-inflammatory drug is in immediate release form and the other portion is in extended release form, the biguanide is in extended release form, and the ARB is in delayed release form.

For purposes of the present invention, it is to be understood that the above dosages of drugs are approximate and that the appended claims encompass obvious variations of the same. It is further contemplated that other drugs in the same drug classes can be substituted for the above drugs/dosages, and such obvious changes are encompassed by the appended claims.

For purposes of the present invention, the term "drug" is used interchangeably with the term "agent" or "active agent" or "test article".

For purposes of the present invention, the term "FDC" or "fixed dose combination" refers to a pharmaceutical formulation containing a specific therapeutically effective dose of one or more orally-active anti-inflammatory drugs as described in this specification and a specific therapeutically effective dose of one or more anti-metabolic disease drugs as described in this specification in any pharmaceutically acceptable carrier(s) such that the pharmaceutical formulation is suitable, e.g., for oral administration, parenteral administration, transdermal administration, nasal administration, buccal administration, topical administration. It is contemplated that the FDC may comprise one or more dosage forms administered concurrently in order to provide the desired therapeutic effect. It is further contemplated that the FDC may encompass one or more routes of administration of the anti-inflammatory and anti-metabolic disease drugs as described herein in order to obtain a desired therapeutic effect. It is contemplated that multiple FDC combinations of the same drug combinations may be made available in order to provide a desired therapeutic effect in different human patients.

For purposes of the present invention, the term "lack of adequate efficacy" is defined as inability to meet the target goals for A1c, blood pressure and cholesterol with prior treatments.

In certain preferred embodiments of the invention, the FDC formulation of the invention comprises a combination of 50 mg to 400 mg Celecoxib (a selective Cox-2 inhibitor), 250 to 2000 mg of Metformin (a biguanide) and an ARB 40 mg to 320 mg Valsartan (Angiotensin II type 1 receptor blocker, an ARB).

DETAILED DESCRIPTION OF THE INVENTION

Figure 1:
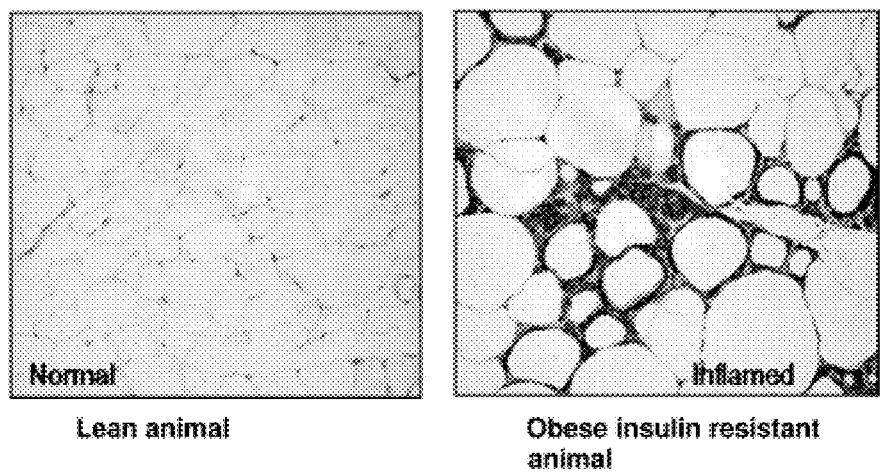
FIG. 1 is comparison of white adipose tissue (WAT) from a lean animal with that of an obese insulin resistant animal: infiltration of macrophages into WAT.

Inflammation and RAS play an important pivotal role in Type II diabetes and its comorbidities. Type II diabetes is characterized progressive deterioration of pancreatic beta cell dysfunction and insulin resistance. Type II diabetes is also characterized by impaired first phase of insulin secretion due to progressive deterioration of pancreatic beta cell function which compromises its inherent capacity to compensate for insulin resistance. Functional response of beta cells and insulin sensitivity of insulin-responsive tissues such as liver and skeletal muscle are tightly regulated by a feed-back loop. The magnitude of beta cell response is directly proportional to the tissue sensitivity of insulin-responsive tissues. This feedback loop determines the normal regulation of glucose metabolism and maintenance of glucose homeostasis. Beta cells have an inherent capacity to compensate with an increased output of insulin when insulin resistance is present. Blood glucose levels rise in the presence of insulin resistance when beta cells are incapable of releasing sufficient insulin due to progressive deterioration of beta cell function. The Renin-Angiotensin System (RAS) exists in the pancreatic beta cells, and Inflammation and RAS play a pivotal role in Type II diabetes and its comorbidities. Angiotensin II (Ang II) is pro-inflammatory in the pancreas and it activates pro-inflammatory cytokine IL-1 beta. Ang II-mediated islet cell inflammation triggers beta cell dysfunction and impairs pancreatic islet cells' inherent capacity for compensating for hyperglycemia. Progressive deterioration pancreatic islet dysfunction leads to decompensation, pancreatic cell exhaustion and pancreatic beta cell failure (Sauter, N. et al. 2015).

With intense mono- and combination therapies with the existing modalities, Type II diabetes patients experience progressive deterioration of metabolic control of glucose homeostasis which is indicative of progressive deterioration of beta cell function in spite of therapies. Progressive deterioration of metabolic control of glucose homeostasis in spite of intense treatments with anti-hyperglycemic drugs results in insulin insufficiency. Blood glucose levels and hepatic gluconeogenesis are tightly regulated by opposing actions of insulin and glucagon. Anti-Inflammatory beta-cell centric methods and formulations disclosed are designed to treat pancreatic beta cell dysfunction in combination with insulin resistance by restoring insulin sufficiency as well as restoring insulin sensitivity for hepatic gluconeogenesis as a result of optimal insulin-glucagon molar ratio.

The methods and formulations disclosed are aimed at filling the gap that currently exists in the modalities used for the treatment of Type II diabetes. The disclosed methods target multiple distinct yet overlapping mechanisms along the immune dysregulation-inflammation-insulin resistance axis that contribute to beta cell dysfunction. The complex etiology of Type II diabetes involves a combination of a variety of cellular dysfunctions including: white adipocytes, infiltrating macrophages that contribute to pancreatic beta cell dysfunction which triggers insulin resistance. Obesity-triggered inflammation involves activation of inducible form of Cyclooxygenase, Cox-2 in tissues such as white adipocytes, infiltrating macrophages where as Cox-2 is the predominant species of Cyclooxygenase expressed in pancreatic beta islet cells. Renin-Angiotensin System (RAS) exists in the islet cells and its activation is pro-inflammatory resulting in elevation of pro-inflammatory cytokines such as IL-1 beta. IL-1 beta-initiated and Cox2-mediated elevation in PGE2 induces beta cell apoptosis and reduces beta cells mass which impairs their inherent capacity to compensate for insulin resistance.

Development of Type II diabetes in humans is categorized into different stages or Phases based on the severity of the disease: Prediabetes is characterized by post-prandial hyperglycemia, impaired glucose tolerance and decreased sensitivity to insulin, Phase I stage is characterized by basal as well as post-prandial hyperglycemia along with increasingly dysfunctional insulin-producing pancreatic beta cells and Phase II stage is characterized by significant beta cell hypertrophy and fasting hyperglycemia and Phase III (end stage) patients can no longer produce insulin and insulin therapy is required (Weir, G. C. et al. 2005). The methods and formulations disclosed will potentially be efficacious in Prediabetes, Phase I and Phase II patients.

There is extensive cross-talk among signaling pathways associated with chronic low-grade inflammation, innate and adaptive immune systems, glucose and lipid metabolism and they are literally inseparable from each other. Based on the preclinical data presented herein together with clinical data previously known to those skilled in the art, efficient clinical management of insulin resistance cannot be achieved by treating chronic hyperglycemia that occurs due to systemic glucose intolerance in isolation without treating the causative inflammation. Lowering inflammatory parameters, treating pancreatic beta cell dysfunction in addition to managing hypertension and lowering lipid levels are expected to contribute to more rapid improvements in CV outcomes with optimal and sustainable glycemic control.

Inflammation-triggered dysfunction of a variety of cell types including infiltrated macrophages and white adipocytes contribute to inflammation-initiated pancreatic beta cell dysfunction. (Saltiel, A. (2000) The molecular and physiological basis of insulin resistance: implications for metabolic and cardiovascular diseases. J. Clin. Invest. 100 (2): 163-164; Weir, G. C. and S. Bonner-Weir (2004) Five stages of evolving beta cel dysfunction during progression to diabetes. Diabetes 53 (Suppl. 3): S16-S21). Pancreatic beta cell dysfunction triggers insulin resistance (Del Prato, S and P. Marchetti, 2004). Cyclooxygenase-2 or Cox-2 is the predominant species of Cyclooxyrgenase expressed in the pancreatic beta cells (Robertson, R. P. (1998) Dominance of Cyclooxygenase-2 in the regulation of pancreatic islet prostaglandin synthesis. Diabetes 47: 1379-1383). Excessive nutrient intake as well as activation of RAS results in the activation of Cox-2-mediated elevation of PGE2 which leads to islet cell dysfunction (Poitou, V. and R. P. Robertson (2009) Glucolipotoxicity: Fuel excess and beta cell dysfunction. Endocrine Reviews 29(3): 351-366). Beta cell dysfunction impairs its inherent capacity for compensating for chronic hyperglycemia. If left untreated, beta cells would suffer potentially irreversible damage by reaching a state of decompensation and eventually to pancreatic exhaustion due to reduction in beta cell mass as a result of PGE2-mediated apoptosis. When beta cells can no longer produce insulin, insulin replacement therapy is required (which is a characteristic of Phase III stage diabetes).

Anti-inflammatory pancreatic beta cell-centric methods disclosed are aimed at treating pancreatic beta islet cell dysfunction in combination with insulin resistance by targeting multiple distinct yet overlapping mechanisms along the immune dysregulation-inflammation-insulin resistance axis.

Activation of Renin-Angiotensin System (RAS) in pancreatic beta islet cells has no effect on vasoconstriction and elevation of systolic blood pressure. Among blockers of Angiotensin II Type 1 receptor (ARBs) such as Losartan, Irbesartan, Telmisartan, Valsartan etc., only Valsartan (to date) has been shown (by the inventor) to increase insulin sensitivity, improve pancreatic islet function and delay the onset of insulin resistance in human clinical trials.

Pro-inflammatory signals in general and Cox-2-mediated pancreatic cell dysfunction in particular play a pivotal role in the development of insulin resistance as well as loss of insulin-sensitive regulation of hepatic gluconeogenesis. Maintenance of normal glucose levels and hepatic gluconeogenesis are tightly controlled by opposing actions of insulin secreted by pancreatic beta cells and glucagon pancreatic alpha cells. Metformin, the current first line of therapy for overt Type II diabetes improves blood glucose levels by primarily blocking hepatic gluconeogenesis.

Figure 2:
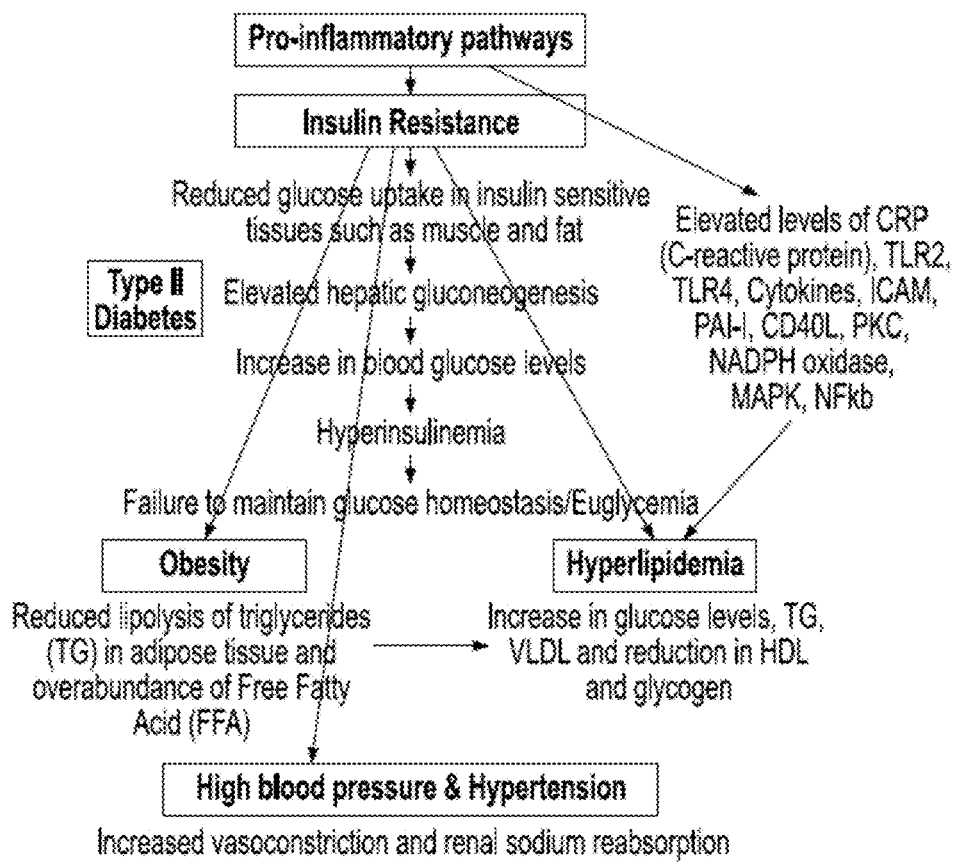
FIG. 2 is a schematic illustration of the Complex pathophysiology of metabolic syndrome.

Obesity in general and obesity-triggered low-grade or sub-acute chronic inflammation is the major contributing factor for systemic insulin resistance, systemic glucose intolerance and systemic lipotoxicity (Xu, H. 2013). Extensive signaling cross-talk among inflammatory signaling pathways, innate and adaptive immune systems, glucose metabolic pathways and lipid metabolism pathways in a temporal as well as contextual manner initiate and sustain impaired glucose homeostasis (Shu, C. J. et al. 2012). The events that initiate and maintain inflammation is central to the complex pathophysiology of obesity-triggered insulin resistance include the following: As the primary tissue for storage of fat, white adipose tissue (WAT) undergoes hyperplasia as preadipocytes differentiate into adipocytes and maintains an anti-inflammatory state acting as a sink with a buffering capacity for fat intake and fat influx (Tateya, S. et al. 2013). The buffering capacity of WAT prevents ectopic fat accumulation and consequently from lipotoxicity (Saltiel, A. 2000). The resident M2 macrophages of hyperplasic WAT secrete anti-inflammatory cytokines such as IL-10, IL-4 and IL-13. The buffering capacity for fat intake in obese patients without insulin resistance occurs as a result of suppression of release of non-esterified fatty acids, decrease in the activity of HSL (Hormone-sensitive lipase) and ATGL (Adipose triglyceride Lipase) (Mitrou, P. et al. 2013). Hyperplasic WAT also have the capacity for increased clearance of triacyl glycerol due to increase in the activity of Lipoprotein lipase (LPL). As white adipocytes accumulate more triacyl glycerol as a result of longterm nutrient excess, they become hypertorphic by increasing in size with concomitant release of monocyte chemoattractant protein (MCP-1) which creates a gradience for recruitment and infiltration of circulating pro-inflammatory M1 macrophages into WAT as shown in FIG. 2 by immunostaining of sections of WAT with macrophagee surface marker F4/80 (Coenen, K. R. et al. 2007). Infiltrated M1 macrophages are retained in WAT due to the synthesis of a guidance molecule known as Netrin-1. Deletion of Netrin-1 results in emigration of infiltrated macrophages in a diet-induced obesity mouse model and improves insulin sensitivity (Ramkhelawon, B. et al. 2014). As the number of M1 macrophages increase, the WAT gradually shifts from an anti-inflammatory state into a pro-inflammatory state as a result of secretion of pro-inflammatory cytokines and chemokines such as IL-6, TNF-alpha, IL-1beta, IL-18, CCL2, CCL3, CXCL8, C-reactive protein (CRP) (Quatanami, M. and Lazar, M. A. 2007). WAT gradually loses its inherent buffering capacity for fat intake and it shifts to a pro-inflammatory state. Elevation in the levels of pro-inflammatory cytokines increases activity of JNK-1 which phosphorylates serine residues on IRS-1 (Insulin receptor substrate-1) rendering it incapable of triggering cascade of signaling events further downstream from IRS-1 in insulin sensitive tissues such as adipocytes, skeletal muscle and hepatocytes. Gradual development of systemic insulin resistance contributes to systemic glucose intolerance as a result of a number of events including: decrease in the levels of adiponectin, Glut4 and IL-10, activation of toll-like receptor, TLR-4 as well as activation of the receptor for Palmitic acid, UNC5b, increase in the levels of leptin, resistin, visfatin and Netrin-1, increase in the levels of PGE metabolites as well as an increase in the level of oxidative stress parameters, pancreatic beta cell dysfunction, activation of SOC (1,2,3)-mediated phosphorylation of IRS-1 and IRS-2, increase in the degradation of IRS-1 and IRS-2, decrease in the levels of thermogenic genes, PGC-1 and UCP-1, and an increase in NLRP3 inflammasome, caspase-1 and ASC (Wang, X. et al. 2014, Boucher, J. et al. 2014). Development of insulin resistance contributes to a decrease in the amount of intracellular glucose which results in elevated levels of blood glucose levels and an increase in the release of non-esterified fatty acid from WAT which results in elevation of circulating levels of free fatty acids (FFA) and triglycerides (TG). It is an established fact that inflammation is central to the complex pathophysiology of not only T2DM and it is also central to the etiology of diabetes-related complications. As a result of systemic glucose intolerance, Type II diabetes patients develop systemic glucolipotoxicity.

Infiltration of circulating M1 macrophages in to the White adipose tissue (WAT) is one of the early events in shifting the WAT from an anti-inflammatory state to an inflammatory state. Comparison of WAT from a lean animal with that of an obese animal is shown in FIG. 2. Sections of WAT are immunostained with a macrophage-specific marker F4/80 (Coenen, K. R. et al. 2007). Macrophages are shown in red.

Figure 3:
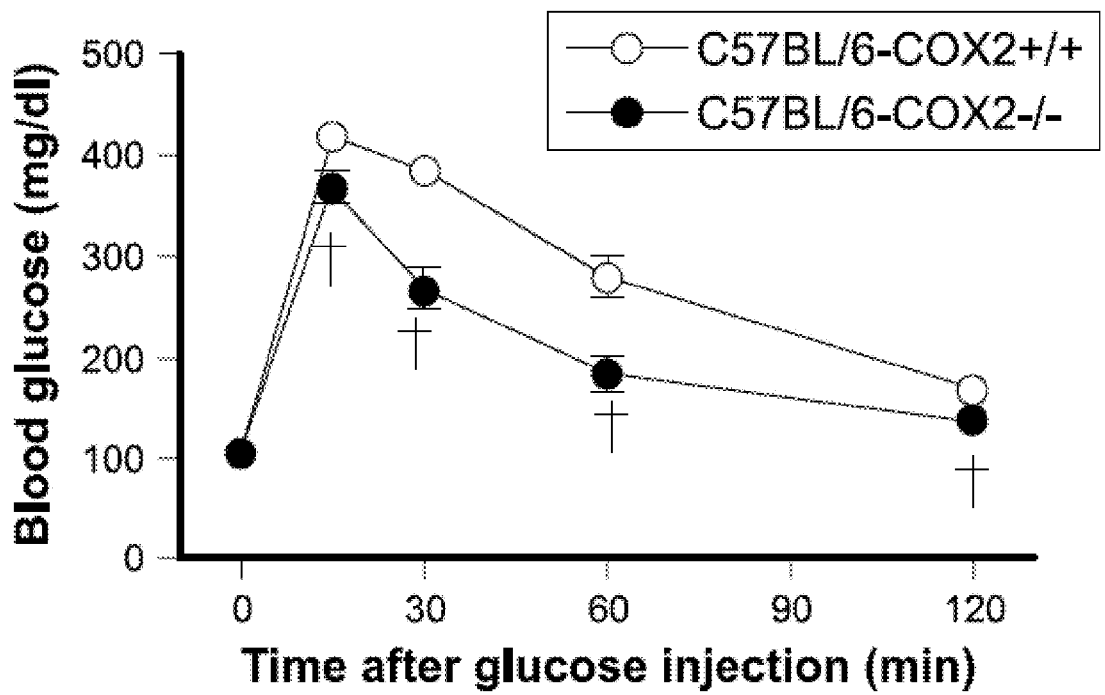
FIG. 3 shows that deletion of Cox-2 in C57BL/6J obese mice reduces blood glucose levels.
Figure 4:
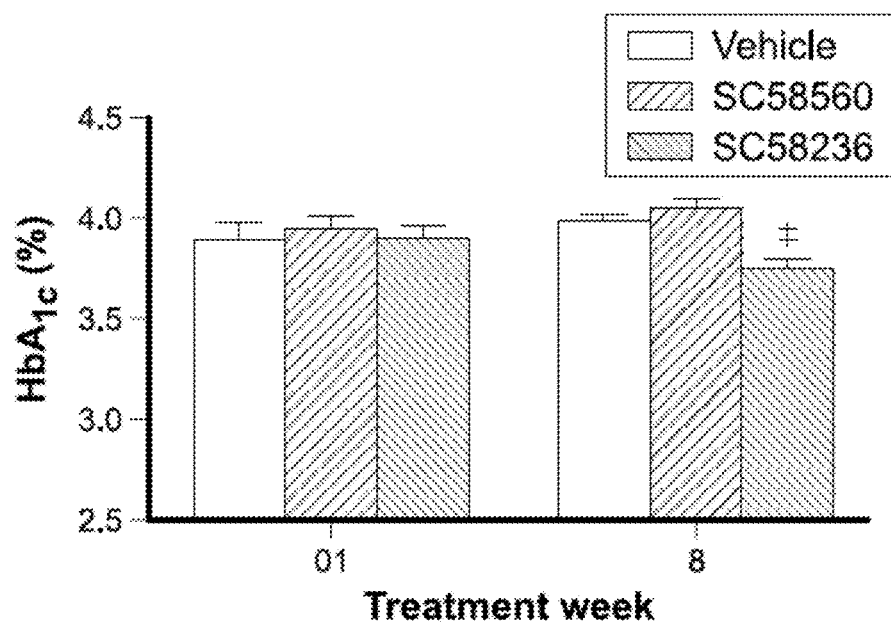
FIG. 4 shows that selective Cox-2 inhibitor, SC58236 reduces HbA1c levels in C57BL/6J obese mice.

Inflammation is the underlying cause of the pathophysiology of not only insulin resistance but also a critical contributing factor to the comorbidities such as hypertension, dyslipidemia and obesity. The complex pathophysiology of the metabolic syndrome is illustrated in FIG. 3. Activation of inducible Cyclooxygenase, Cox-2 or activation of constitutive Cox-2 plays a critically important role in the initiation of obesity-triggered inflammation. A link between elevation of blood glucose levels and activation of Cox-2 in pancreatic beta cells is well established (Oshima, H. et al. 2006). C57BL/6J DIO (Diet-induced obesity) mice are an established polygenic preclinical translational model for Type II diabetes, prediabetes, glucose intolerance and insulin resistance. Selective deletion of Cox-2 improves glucose tolerance after glucose loading (2 g/Kg) after fasting mice for 6 hours in an intraperitoneal glucose tolerance test (IPGTT) as shown FIG. 4 (Fujita, H. et al. 2007). Blood samples were taken from the cavernous sinus by capillary under anesthetized condition at 0.5 h before (0 h in the figure) and at 0.5, 1, 2 and 5 h after glucose loading. Blood glucose was measured using Glucord Diameter. (Arkray, Tokyo, Japan).

Figure 5A:
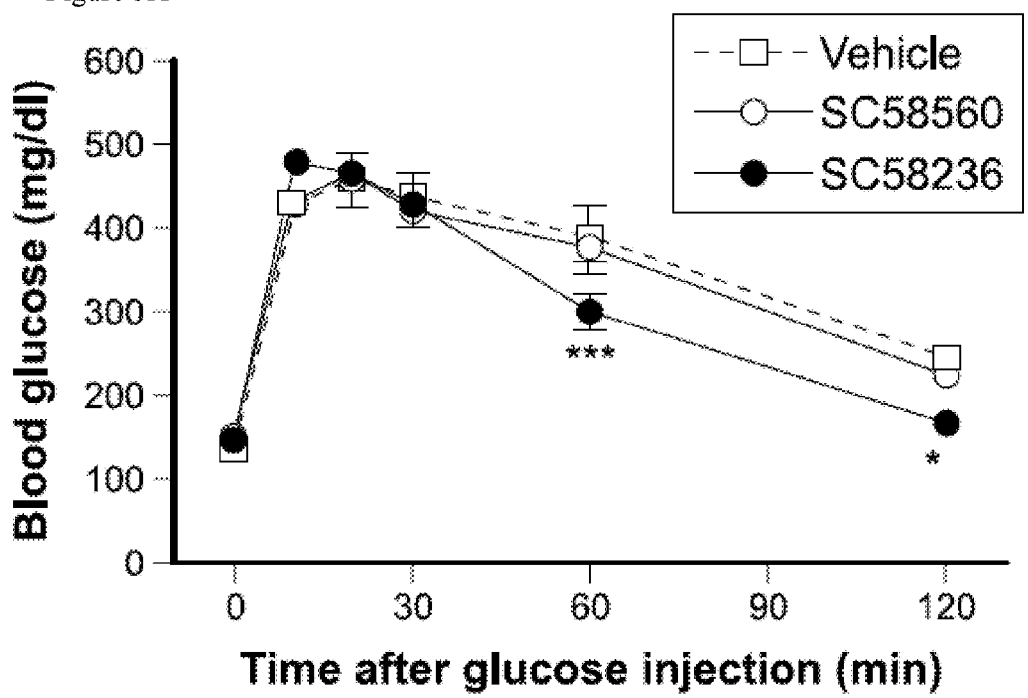
FIGS. 5A and 5B show that selective Cox-2 inhibitor, SC58236 improves glucose tolerance and elevates plasma insulin levels in C57BL/6J obese mice.
Figure 5B:
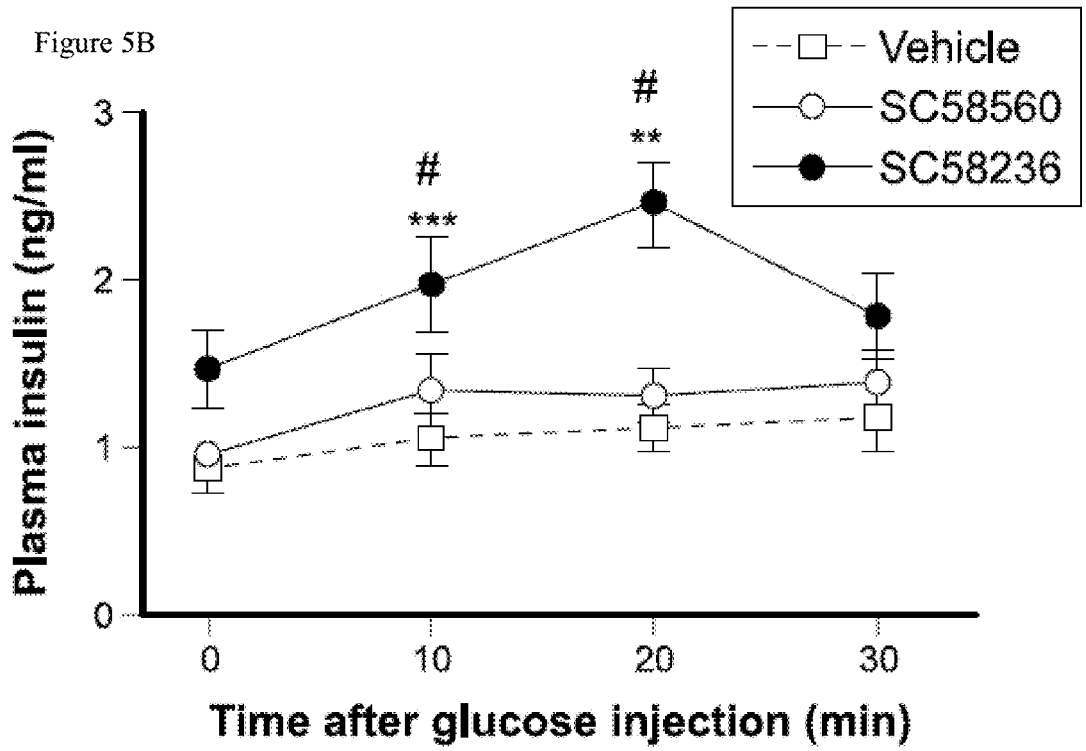

Cox-2 is the predominant species of cyclooxygenase expressed pancreatic beta islet cells. Excessive nutrient intake as well as activation of RAS results in the activation of Cox-2. Cox-2-mediated elevation in PGE2 impairs pancreatic compensation and leads to islet cell dysfunction (Poitout, V and Robertson, R. P. 2008). Elevation in PGE2 levels contributes to reduction beta islet cell mass due to decreased hyperplasia as well as due to apoptosis of the beta islet cells. As shown in FIG. 5, selective Cox-2 inhibition reduces HbA1c levels by about 0.4%. SC58560 and SC58236 are selective Cox-1 and Cox-2 inhibitors respectively (Fujita, H. et al. 2007). HbA1c levels were determined using a DCA 2000 Analyzer (Bayer, Elkhart, Ind.).

Figure 6:
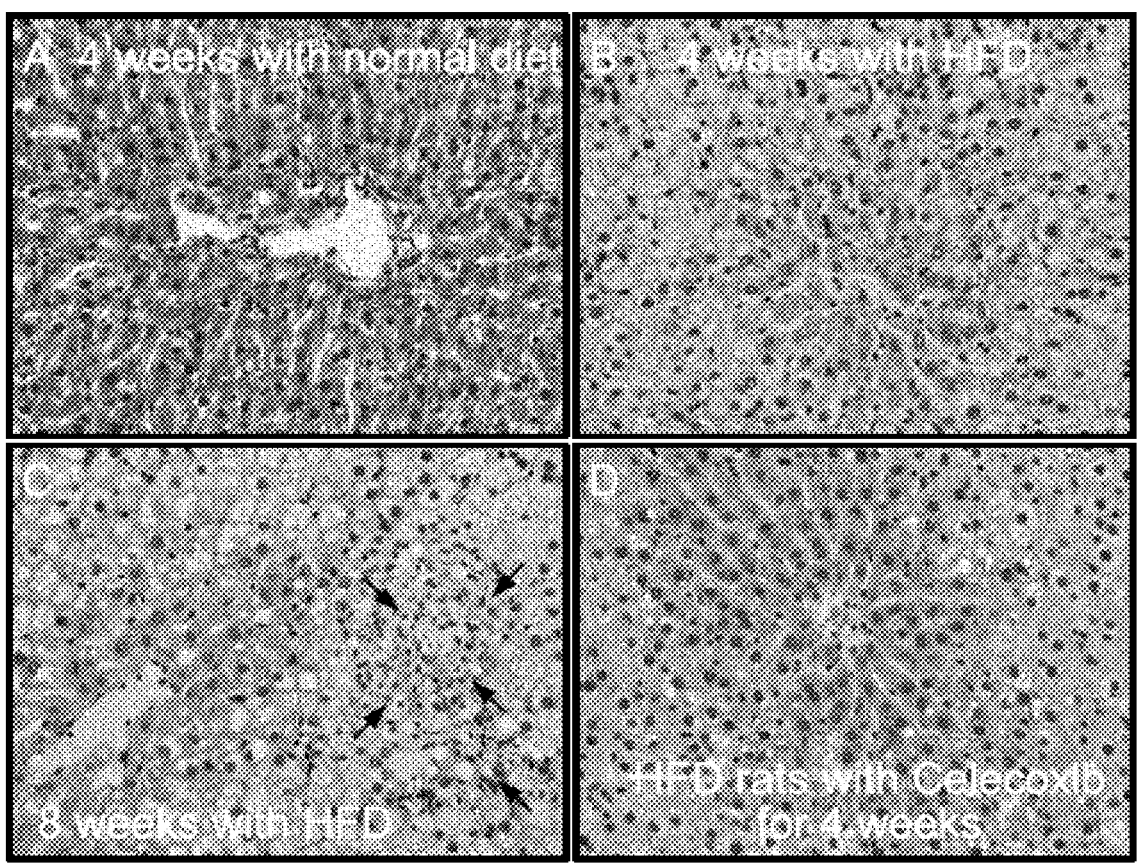
FIG. 6 shows that selective Cox-2 inhibitor, Celecoxib reverses steatohepatitis and inflammation in Wistar rat NASH model.

Selective inhibition of Cox-2 improves glucose tolerance in an intraperitoneal glucose tolerance test (IPGTT) and elevates plasma insulin levels as shown in FIG. 6 (Fujita, H. et al. 2007). IPGTT was performed after mice were fasted for 6 hours. After glucose loading (2 g/Kg), blood samples were taken from the cavernous sinus by capillary under anesthetized condition at 0.5 h before (0 h in the figure) and at 0.5, 1, 2 and 5 h. Blood glucose was measured using Glucord Diameter. (Arkray, Tokyo, Japan). Plasma insulin levels after glucose injection were measured using a commercial insulin ELISA kit (Morinaga, Yokohama, Japan).

Figure 7:
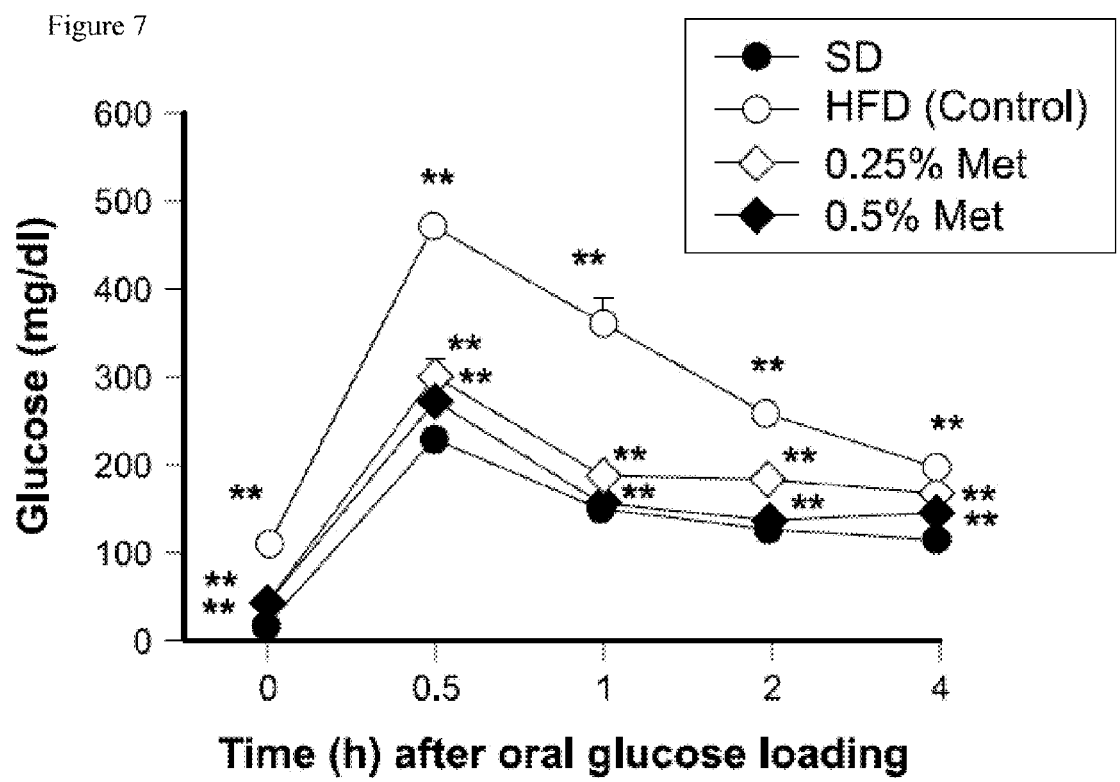
FIG. 7 shows that metformin improves glucose tolerance in C57BL/6J diet-induced obesity (DIO) mice.

Non-alcoholic staeatohepatitis (NASH) is a condition that coexists with Type II diabetes. Celecoxib, a selective Cox-2 inhibitor reverses steatohepatitis and inflammation in Wistar rat NASH model (Chen, J. et al. 2011). FIG. 7 shows the histological changes in the liver of rats on HFD (high fat diet) and Celecoxib-treated rats. Rats on normal diet were used as controls. A. Wistar rats on normal diet for 4 weeks showed normal liver histology, (B) When rats fed the HFD for 4 weeks, fat droplets and small groups of inflammatory cells (arrow) were observed. (C) After 8 weeks of HFD feeding, severity of steatohepatitis greatly increased. (D) Treatment of HFD rats with Celecoxib (20 mg/kg/day) for 4 weeks attenuated steatohepatitis. Arrows point to fat droplets and groups of inflammatory cells. Sections of liver were stained with eosin and hematoxylin.

Figure 8:
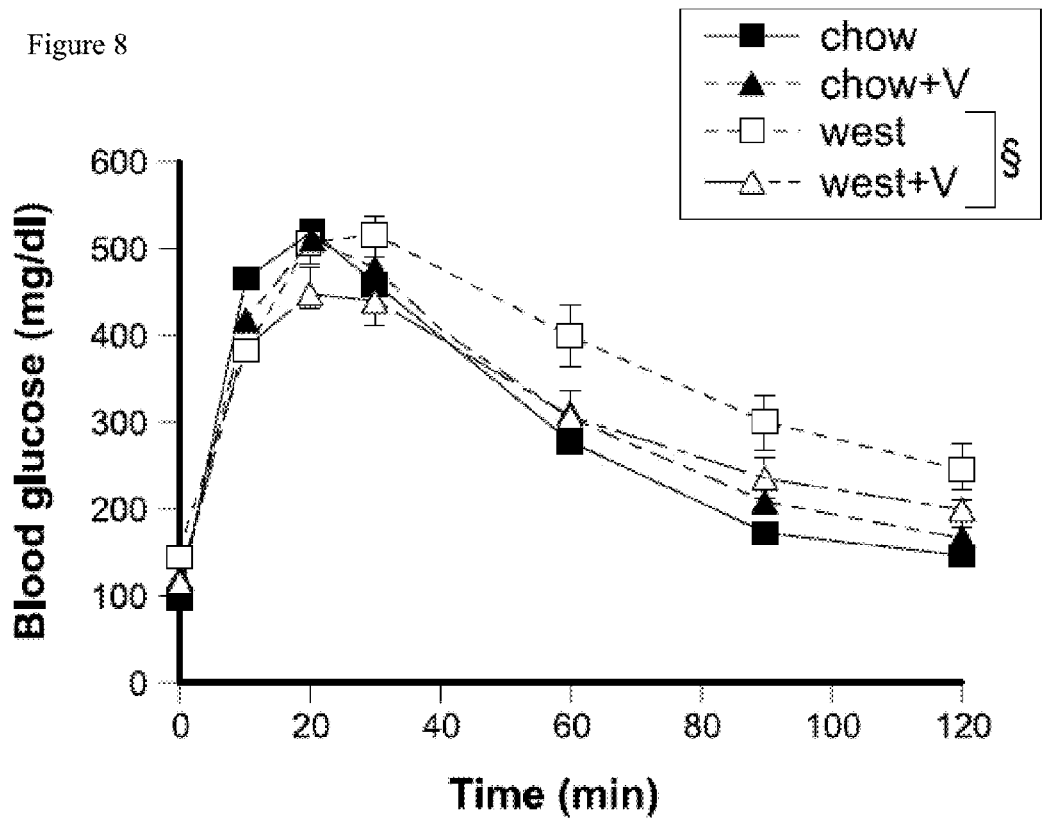
FIG. 8 shows that Valsartan improves glucose tolerance in C57BL/6J diet-induced obesity (DIO) mice.

Metformin, a biguanide is the gold standard among the currently marketed Type II diabetes drugs. As shown in FIG. 8, it improves glucose tolerance in C57BL/6J diet-induced obese (DIO) mice model in oral glucose tolerance test (OGTT) in which the mice were challenged with 2 g/Kg body weight glucose after fasting mice for 20 hours (Matsui, Y. et al. 2010). 0.25% and 0.5% Metformin are 150 mg/Kg/day and 300 mg/Kg/day respectively. Plasma glucose levels were determined by using Glucose II-Test Wako purchased from Wako Pure Chemical Industries, Ltd. (Osaka, Japan).

Valsartan (Diovan) is a selective Angiotensin receptor Type I receptor blocker (ARB). RAS play a critically important role in inflammation-induced beta islet cell dysfunction as well in the process of pancreatic decompensation. Valsartan has been shown to delay the onset of Type II diabetes in prediabetes patients as well (Andraws, R. and D. L. Brown, 2007). In a randomized controlled, double blind, two-center clinical study conducted for 26 weeks, Valsartan improved beta cells function and insulin sensitivity in subjects with impaired glucose metabolism (Van der Zijl, N. et al. 2011). As shown in FIG. 8, Valsartan improves glucose tolerance in C57BL/6J diet-induced obese (DIO) mice. For testing glucose tolerance, mice were fasted overnight and then injected intraperitoneally (IP) with 2 g/Kg glucose. Blood glucose measurements were performed with an Ultra-Touch glucometer using blood samples taken from cut tail tips at baseline, 15, 30, 45 and 60 minutes after the injection of glucose (Cole, B. K. et al. 2010).

The results described herein suggest when the leading anti-hyperglycemic drug such as Metformin becomes inefficacious due to insulin insufficiency as a result of pancreatic beta cell insufficiency, co-treatment with sub-therapeutic dose of Celecoxib and sub-systolic blood pressure dose of Valsartan restores insulin sufficiency by treating pancreatic beta cell dysfunction. The results described herein further suggest that the anti-inflammatory pancreatic beta cell-centric product combination has the potential for a future standard of care for obesity-triggered cancers such as breast cancer, non-alcoholic steatohepatitis (NASH), non-alcoholic fatty liver disease (NAFLD), obstructive sleep apnea, thrombotic diseases such as myocardial infarction (MI) and ischemic stroke, polycystic ovarian disease and diabetic neuropathy. Further, the results described herein suggest that the anti-inflammatory pancreatic beta cell-centric product combination has the potential for a future standard of care for conditions that coexist with Type II diabetes such as osteoarthritis (OA), rheumatoid arthritis (RA), non-alcoholic steatohepatitis (NASH), non-alcoholic fatty liver disease (NAFLD), and obstructive sleep apnea.

None of the drugs that are currently on the market prevent, delay or restore progressive deterioration of pancreatic beta cells. Innovative and novel anti-inflammatory beta-cell centric methods and formulations that are disclosed here are aimed at treating beta cell dysfunction, restore insulin sufficiency and maintain its inherent capacity to compensate for insulin resistance. The novel and innovative combination of Metformin, Celecoxib and Valsartan has the distinguishing property of restoring the inherent capacity of pancreatic beta cells to compensate for insulin resistance by treating beta cell dysfunction.

Methods and processes involved in the preparation of tablets, capsules and tablets inside a capsule will be improved and optimized for the FDC formulations described and disclosed in this application. Dosing of granules for the bottom layer will be placed in the rotary die from the first hopper followed by recompression of the first layer by the first roller. The first layer will be reduced to a smaller size to create space required for the second feeder. Dosing of the top layer would occur from the second hopper to the rotary die. The filled die will be transferred to the second roller for compression. Final compression of the two layers would result in two distinct layers. Multilayer tablet machines will be equipped with suction nozzles or dust extractor to remove fine powder granules to eliminate cross-contamination between the two layers.

A therapeutic dose of an anti-inflammatory drug will be combined with therapeutic doses of one or more anti-type II diabetic, anti-hypertensive, lipid lowering and anti-obesity drugs with predetermined modified release kinetics to achieve therapeutic as well as kinetic synergies.

Therapeutic doses of a combination of anti-inflammatory drugs, anti-type II diabetes drugs, lipid lowering drugs and anti-obesity drugs will be formulated in the form of fixed dose combination products (FDC) to treat Type II diabetes patients who are stratified into groups based on their cardiometabolic risk factor profiles.

Therapeutic doses of a combination of anti-inflammatory drugs, anti-type II diabetes drugs, lipid lowering drugs and anti-obesity drugs will be formulated in the form of fixed dose combination products (FDC) to treat Type II diabetes patients who are stratified into groups for lack adequate therapeutic efficacy and over all clinical benefit from the prior treatments.

Therapeutic doses of a combination of anti-inflammatory drugs, anti-type II diabetes drugs, lipid lowering drugs and anti-obesity drugs will be formulated in the form of fixed dose combination products (FDC) to prevent or delay the onset of Type II diabetes in Prediabetes patients.

FDC formulations contain the following combinations in the form of single layer monolithic tablet or multi-layered monolithic tablet or in the form of a core tablet-in-tablet or multi-layered multi-disk tablet or beads inside a capsule or tablets inside a capsule but not limited to: (a) therapeutically efficacious Fixed Dose Combinations (FDC) of IR formulations of different drugs; (b) Therapeutically efficacious FDC of IR and ER formulations of different drugs; Therapeutically efficacious FDC of IR and ER formulations of the same drug in combinations with ER formulations of one or more of different drugs; Therapeutically efficacious FDC of IR and ER formulations of the same drug in combinations with ER formulations of one or more of the same drug; and/or Therapeutically efficacious FDC of IR and ER formulations of the same drug in combinations with ER formulations of one or more of different drugs to compensate for potential adverse side effects such as hypoglycemia.

Preparation of FDC Formulations

Methods and compositions to treat metabolic and cardiovascular diseases have been described in general in several issued patents and patent applications such as U.S. Pat. Nos. 5,561,165, 8,431,522, 7,632,818, 8,586,607, 8,759,334, 8,586,529, 6,846,800, 8,507,451, 5,190,970, 8,586,069 B2, U.S. Pat. No. 8,435,550 B2, WO 2008014471 A1, U.S. Pat. No. 8,367,418 B2, WO 2004017896 A2, U.S. Pat. No. 8,008,328 B2, WO 2010088375 A2, US 20130261092 A1, US 20140037739 A1, WO 2005009412 A1, EP 2727587 A1 and WO 2011 078993.

Tablets of the invention described here can be prepared by methods well known in the art. Various methods for IR, QR, ER, SR, XR, DR layers and the vehicles therein are well known in the art. Generally recognized compendium of methods include: Remington: The Science and Practice of Pharmacy, Alfonso R. Gennaro, Editor, 20th Edition, Lippinscott Williams & Wilkins, Philadelphia, Pa.; Sheth et al. (1980) Compressed tablets, in Pharmaceutical dosage forms, Vol 1, edited by Lieberman and Lachtman, Dekker, N.Y.

Published methods (Shende, P. et al. 2012; Khan, Z. et al. 2013) will be optimized further to generate delivery systems in the form of FDC formulations.

For oral, buccal, and sublingual administration, powders, suspensions, granules, tablets, pills, capsules, gelcaps, and caplets are acceptable as solid dosage forms.

These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these pharmaceutically suitable surfactants, suspending agents, emulsifying agents, may be added for oral or parenteral administration. As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Immediate release formulations will be prepared by combining super disintegrant such as Croscarmellose sodium and different grades of microcrystalline cellulose in different ratios. To aid disintegration, sodium starch glycolate will be added. A formulation method which would result in tablet disintegration of >98% in less than a minute will be used in the final formulation.

Published methods will be used to prepare FDC of drugs either in the form of a form of beads inside a capsule. Each bead would represent different color and coating level depending on the kinetics of drug release. For example, some beads would release drugs immediately (IR). Some would beads would release for an extended period of time (ER), while some after a long while (DR).

As an example, extended release multi-layered matrix tablets will be prepared by using FDC of different drugs and hydrophilic polymer ratio with guar gum, hydroxypropyl-methyl cellulose, and xanthan gum as matrix formers. All lubricated formulations will be compressed by wet granulation method.

Multilayer tablet delivery procedure used in the GeoMatrix™ Technology will be used. It consists of a hydrophilic matrix core, containing the active ingredient, and one or two impermeable or semi-permeable polymeric coatings. This technology uses films or compressed polymeric barrier coatings on one or both sides of the core.

The presence of polymeric coatings in the GeoMatrix™ Technology, modifies the hydration/swelling rates of the core and reduces the surface area available for drug release. These partial coatings provide a modulation of the drug dissolution profile: they reduce the release rate from the device and shift the typical time-dependent release rate towards constant release. This technology enables customized levels of controlled release of specific drugs and/or simultaneous release of two different drugs at different rates can be achieved from a single tablet. The combination of layers, each with different rates of swelling, gelling and erosion, is used for the rate of drug release in the body. Exposure of the multilayer tablet as a result of partial coating may affect the release and erosion rates, therefore, transformation of multilayered tablet with exposure on all sides to the gastrointestinal fluids upon detachment of the barrier layer will be considered.

Multi-layered tablets containing combinations of immediate release and modified/extended release of two different drugs or dual release rate of the same drug in a single dosage form will be prepared by using hydrophilic and hydrophobic polymer matrices.

Dual release repeat action multi-layered tablets will be prepared with an outer compression layer with an initial dose of rapidly disintegrating matrix in the stomach and a core inner layer tablet formulated with components that are insoluble in the gastric media but release efficiently in the intestinal environment.

Cross-contamination between different layers will be prevented by using barrier layers of inert/non-functional material.

Quality control methods and best industry practices will be developed and adopted to meet international Pharmacopeial standards.

Multilayered matrix tablets of a combination of immediate and/or extended release tablets will be evaluated for a number of physico-chemical properties (Khan, Z. et al. 2013)

a) Uniformity of weight
b) Content of active ingredient/drug content
c) Friability
d) Hardness
e) Thickness
f) Weight uniformity
g) Disintegration time
h) In vitro drug release/dissolution
i) Stability Compositions containing the active agent(s) of the present invention can be formulated for administration to a subject via any conventional means including, but not limited to, oral, parenteral (e.g., intravenous, subcutaneous, or intramuscular), buccal, intranasal or transdermal administration routes.

Moreover, the pharmaceutical compositions described herein can be formulated into any suitable dosage form, including but not limited to, aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, tablets, capsules, pills, powders, delayed release formulations, immediate release formulations, modified release formulations, extended release formulations, pulsatile release formulations, multiparticulate formulations, and mixed immediate release and controlled release formulations. In some embodiments, the active agent(s) of the present invention formulations provide a therapeutically effective amount of the active agent(s) of the present invention over an interval of about 30 minutes to about 8 hours after administration, enabling, for example, once-a-day, twice-a-day (b.i.d.), or three times a day (t.i.d.) administration if desired. In one embodiment, the active agent(s) of the present invention particles are formulated into a controlled release or pulsatile solid dosage form for b.i.d. administration. In other embodiments, the active agent(s) of the present invention particles are dispersed in an aqueous dispersion for b.i.d. administration. Generally speaking, one will desire to administer an amount of the active agent(s) of the present invention that is effective to achieve a plasma level commensurate with the concentrations found to be effective in vivo for a period of time effective to elicit a desired therapeutic effect.

The various release dosage formulations discussed above can be characterized by their disintegration profile. A profile is characterized by the test conditions selected. Thus the disintegration profile can be generated at a pre-selected apparatus type, shaft speed, temperature, volume, and pH of the dispersion media. Several disintegration profiles can be obtained. For example, a first disintegration profile can be measured at a pH level approximating that of the stomach (about pH 1.2); a second disintegration profile can be measured at a pH level approximating that of one point in the intestine or several pH levels approximating multiple points in the intestine (about 6.0 to about 7.5, more specifically, about 6.5 to 7.0). Another disintegration profile can be measured using distilled water. The release of formulations may also be characterized by their pharmacokinetic parameters, for example, Cmax, Tmax, and AUC (0-τ).

In one embodiment, the dosage form is a solid oral dosage form which is an immediate release dosage form whereby >80% of the active agent(s) of the present invention particles hours after administration. In other embodiments, the invention provides an (e.g., solid oral) dosage form that is a controlled release or pulsatile release dosage form. In such instances, the release may be, e.g., 30 to 60% of the active agent(s) of the present invention particles by weight are released from the dosage form within about 2 hours after administration and about 90% by weight of the active agent(s) of the present invention released from the dosage form within about 7 hours after administration. In yet other embodiments, the dosage form includes at least one active agent in immediate release form and at least one active agent in delayed release form, or sustained release form. In yet other embodiments, the dosage form includes at least two active agents which are released at different rates as determined by in-vitro dissolution testing or via oral administration.

In some embodiments, the solid dosage forms of the present invention may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the present invention may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing the active agent(s) of the present invention particles with one or more pharmaceutical excipients to form a bulk blend composition. When referring to these bulk blend compositions as homogeneous, it is meant that the active agent(s) of the present invention particles are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluents. These the active agent(s) of the present invention formulations can be manufactured by conventional pharmaceutical techniques.

Conventional pharmaceutical techniques for preparation of solid dosage forms include, e.g., one or a combination of methods: (1) dry mixing, (2) direct compression, (3) milling, (4) dry or non-aqueous granulation, (5) wet granulation, or (6) fusion. See, e.g., Lachman et al., Theory and Practice of Industrial Pharmacy (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can comprise the active agent(s) of the present invention compositions described herein and one or more pharmaceutically acceptable additives such as a compatible carrier, binder, complexing agent, ionic dispersion modulator, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the active agent(s) of the present invention formulation. In one embodiment, some or all of the active agent(s) of the present invention particles are coated. In another embodiment, some or all of the active agent(s) of the present invention particles are microencapsulated. In yet another embodiment, some or all of the active agent(s) of the present invention is amorphous material coated and/or microencapsulated with inert excipients. In still another embodiment, the active agent(s) of the present invention particles not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calciumphosphate, calcium sulfate, microcrystalline cellulose (e.g., Avicel®, Avicel® PH101, Avicel® PH102, Avicel® PH105, etc.), cellulose powder, dextrose, dextrates, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

If needed, suitable disintegrants for use in the solid dosage forms described herein include, but are not limited to, natural starch such as corn starch or potato starch, a pregelatinized starch such as National 1551 or Amijel®, or a sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, Ac-Di-Sol, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and in tablet formulation, binders ensure that the tablet remains intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crosspovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like. In general, binder levels of 20-70% are used in powder-filled gelatin capsule formulations. Binder usage level in tablet formulations is a function of whether direct compression, wet granulation, roller compaction, or usage of other excipients such as fillers which itself can act as moderate binder are used. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Non water-soluble diluents are compounds typically used in the formulation of pharmaceuticals, such as calcium phosphate, calcium sulfate, starches, modified starches and microcrystalline cellulose, and microcellulose (e.g., having a density of about 0.45 g/cm3, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like. Wetting agents include surfactants.

Suitable surfactants for use in the solid dosage forms described herein include, for example, docusate and its pharmaceutically acceptable salts, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 18000, vinyl pyrrolidone/vinyl acetate copolymer (S630), sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), butylhydroxyanisole (BHA), sodium ascorbate, Vitamin E TPGS, ascorbic acid, sorbic acid and tocopherol.

The above-listed additives should be taken as merely exemplary, and not limiting, of the types of additives that can be included in solid dosage forms of the present invention. The amounts of such additives can be readily determined by one skilled in the art, according to the particular properties desired.

Compressed tablets are solid dosage forms prepared by compacting the bulk blend the active agent(s) of the present invention formulations described above. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the active agent(s) of the present invention formulation. In other embodiments, the film coating aids in patient compliance (e.g., Opadry® coatings or sugar coating). Film coatings comprising Opadry® typically range from about 1% to about 3% of the tablet weight. Film coatings for delayed release usually comprise 2-6% of a tablet weight or 7-15% of a spray-layered bead weight. In other embodiments, the compressed tablets comprise one or more excipients.

A capsule may be prepared, e.g., by placing the bulk blend the active agent(s) of the present invention formulation, described above, inside of a capsule. In some embodiments, the active agent(s) of the present invention formulations (non-aqueous suspensions and solutions) are placed in a soft gelatin capsule. In other embodiments, the active agent(s) of the present invention formulations are placed in standard gelatin capsules or non-gelatin capsules such as capsules comprising HPMC. In other embodiments, the active agent(s) of the present invention formulations are placed in a sprinkle capsule, wherein the capsule may be swallowed whole or the capsule may be opened and the contents sprinkled on food prior to eating. In some embodiments of the present invention, therapeutic dose is split into multiple (e.g., two, three, or four) capsules. In some embodiments, the entire dose of the active agent(s) of the present invention formulation is delivered in a capsule form. For example, the capsule may comprise between about 100 mg to about 600 mg of the active agent(s) of the present invention. In some embodiments, the capsule may comprise between about 100 to about 500 mg of the active agent(s) of the present invention. In other embodiments, capsule may comprise about 300 mg to about 400 mg of the active agent(s) of the present invention.

Another useful capsule has a shell comprising the material of the rate-limiting membrane, including any of the coating materials previously discussed, and filled with the active agent(s) of the present invention particles. A particular advantage of this configuration is that the capsule may be prepared independently of the active agent(s) of the present invention particles, thus process conditions that would adversely affect the drug can be used to prepare the capsule. A preferred embodiment is a capsule having a shell made of a porous or a pH-sensitive polymer made by a thermal forming process. An especially preferred embodiment is a capsule shell in the form of an asymmetric membrane; i.e., a membrane that has a thin skin on one surface and most of whose thickness is constituted of a highly permeable porous material. A preferred process for preparation of asymmetric membrane capsules comprises a solvent exchange phase inversion, wherein a solution of polymer, coated on a capsule-shaped mold, is induced to phase-separate by exchanging the solvent with a miscible non-solvent.

In yet another embodiment, spray layered active agent(s) of the present invention particles are filled in a capsule. An exemplary process for manufacturing the spray layered the active agent(s) of the present invention is the fluidized bed spraying process. The active agent(s) of the present invention suspensions or the active agent(s) of the present invention complex suspensions described above are sprayed onto sugar or microcrystalline cellulose (MCC) beads (20-35 mesh) with Wurster column insert at an inlet temperature of 50° C. to 60° C. and air temp of 30° C. to 50° C. A 15 to 20 wt % total solids content suspension containing 45 to 80 wt % the active agent(s) of the present invention, 10 to 25 wt % hydroxymethylpropylcellulose, 0.25 to 2 wt % of SLS, 10 to 18 wt % of sucrose, 0.01 to 0.3 wt % simethicone emulsion (30% emulsion) and 0.3 to 10% NaCl, based on the total weight of the solid content of the suspension, are sprayed (bottom spray) onto the beads through 1.2 mm nozzles at 10 mL/min and 1.5 bar of pressure until a layering of 400 to 700% wt % is achieved as compared to initial beads weight. The resulting spray layered the active agent(s) of the present invention particles or the active agent(s) of the present invention complex particles comprise about 30 to 70 wt % of the active agent(s) of the present invention based on the total weight of the particles. In one embodiment the capsule is a size 0 soft gelatin capsule In one embodiment, the capsule is a swelling plug device. In another embodiment, the swelling plug device is further coated with cellulose acetate phthalate or copolymers of methacrylic acid and methylmethacrylate.

In some embodiments the capsule includes at least 250 mg (or at least 300 mg or at least 400 mg) the active agent(s) of the present invention and has a total weight of less than 800 mg (or less than 700 mg). The capsule may contain a plurality of the active agent(s) of the present invention-containing beads, for example spray layered beads. In some embodiments the beads are 12-25% the active agent(s) of the present invention by weight. In some embodiments some or all of the active agent(s) of the present invention containing beads are coated with a coating comprising 6 to 15% (or 8 to 12%) of the total bead weight. Optimization work typically involves lower loading levels and the beads constitute 30 to 60% of the finished bead weight. The capsule may contain a granulated composition, wherein the granulated composition comprises the active agent(s) of the present invention.

The capsule may be pulsatile release the active agent(s) of the present invention oral dosage form, comprising: (a) a first dosage unit comprising a first the active agent(s) of the present invention dose that is released substantially immediately following oral administration of the dosage form to a patient; (b) a second dosage unit comprising a second the active agent(s) of the present invention dose that is released approximately 3 to 7 hours following administration of the dosage form to a patient. For pulsatile release capsules containing beads the beads can be coated with a coating comprising 6 to 15% (or 8 to 12%) of the total bead weight. In some embodiments the coating is a coating that is insoluble at pH 1 to 2 and soluble at pH greater than 5.5.

In certain embodiments, the formulation may comprise a pulsatile release capsule comprising at least two active agents. This pulsatile release capsule may contain a plurality of beads in which some beads are immediate release beads and other beads are formulated, for example with the use of a coating, for modified release, typically from about 3 to about 10 hours after administration. In other embodiments the pulsatile release capsule contains a plurality of beads formulated for modified release and the active agent(s) of the present invention powder, for example spray granulated the active agent(s) of the present invention, for immediate release.

In some embodiments, the release of the active agent(s) of the present invention particles can be modified with a modified release coating, such as an enteric coating using cellulose acetate phthalate or a sustained release coating comprising copolymers of methacrylic acid and methylmethacrylate. In one embodiment, the enteric coating may be present in an amount of about 0.5 to about 15 wt %, more specifically, about 8 to about 12 wt %, based on the weight of, e.g., the spray layered particles. In one embodiment, the spray layered particles coated with the delayed and/or sustained release coatings can be filled in a modified release capsule in which both enteric coated and immediate release the active agent(s) of the present invention beads are filled into a soft gelatin capsule. Additional suitable excipients may also be filled with the coated particles in the capsule. The uncoated particles release the active agent(s) of the present invention immediately upon administration while the coated particles do not release the active agent(s) of the present invention until these particles reach intestine. By controlling the ratios of the coated and uncoated particles, desirable pulsatile release profiles may be obtained. In some embodiments, the ratios between the uncoated and the coated particles are e.g., 20/80, or 30/70, or 40/60, or 50/50, w/w to obtain desirable release.

In some embodiments, the spray layered active agent(s) of the present invention particles can be compressed into tablets with commonly used pharmaceutical excipients. Any appropriate apparatus for forming the coating can be used to make the enteric coated tablets, e.g., fluidized bed coating using a Wurster column, powder layering in coating pans or rotary coaters; dry coating by double compression technique; tablet coating by film coating technique, and the like. See, e.g., U.S. Pat. No. 5,322,655; Remington's Pharmaceutical Sciences Handbook: Chapter 90 "Coating of Pharmaceutical Dosage Forms", 1990.

In various embodiments, the spray layered the active agent(s) of the present invention described above and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the active agent(s) of the present invention formulation into the gastrointestinal fluid.

In other embodiments, the spray layered the active agent(s) of the present invention particles or spray layered the active agent(s) of the present invention complex particles with enteric coatings described above and one or more excipients are dry blended and compressed into a mass, such as a tablet. In one embodiment, the enteric coated particles in the tablet substantially avoids release of the active agent(s) of the present invention, for example less than 15 wt %, in the stomach but releases substantially all the active agent(s) of the present invention (enterically or sustained release coated), for example, greater than 80 wt %, in the intestine.

In yet other embodiments, a pulsatile release the active agent(s) of the present invention formulation comprises a first dosage unit comprising a formulation made from the active agent(s) of the present invention containing granules made from a spray drying or spray granulated procedure or a formulation made from the active agent(s) of the present invention complex containing granules made from a spray drying or spray granulated procedure without enteric or sustained release coatings and a second dosage unit comprising spray layered the active agent(s) of the present invention particles or spray layered the active agent(s) of the present invention complex particles with enteric or sustained release coatings. In one embodiment, the first dosage unit and the second dosage unit are wet or dry blended and compressed into a mass to make a pulsatile release tablet.

In another embodiment, binding, lubricating and disintegrating agents are blended (wet or dry) to the spray layered the active agent(s) of the present invention to make a compressible blend. The first and the second dosage units are compressed separately and then compressed together to form a bilayer tablet. In yet another embodiment, the first dosage unit is in the form of an overcoat and completely covers the second dosage unit.

Roller compaction, which involves dry granulation of single powder or a blended mixture of powders by the use of pressure to form dense compacts (the compacts are subsequently milled to a desired particle size), provides another alternative. It is a simple process that is readily available for use, and does not involved the use of solvents for granulation. Thus, roller compaction eliminates the exposure of sensitive active pharmaceutical ingredients to moisture and drying. Roller compaction can also provide some enhanced stability and taste-masking characteristics to active pharmaceutical by diluting and isolating such components in a granulated matrix of compatible ingredients. Roller compaction also imparts increased density and flow to the powder.

Extrusion/spheronization is another method that involves wet massing of active pharmaceutical ingredients, followed by the extrusion of the wet mass through a perforated plate to produce short cylindrical rods. These rods are subsequently placed into a rapidly rotating spheronizer to shape the cylindrical rods into uniform spheres. The spheres are subsequently dried using a fluid bed drier and then coated with a functional coating using a fluid bed equipped with a Wurster insert and spray nozzle.

In other embodiments a powder comprising the active agent(s) of the present invention formulations described herein may be formulated to comprise one or more pharmaceutical excipients and flavors. Such a powder may be prepared, for example, by mixing the active agent(s) of the present invention formulation and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process In still other embodiments, effervescent powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include, e.g: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In certain embodiments, ingredients (including or not including the active agent(s)) of the invention are wet granulated. The individual steps in the wet granulation process of tablet preparation include milling and sieving of the ingredients, dry powder mixing, wet massing, granulation, drying and final grinding. In various embodiments, the active agent(s) of the present invention composition is added to the other excipients of the pharmaceutical formulation after they have been wet granulated.

Alternatively, the ingredients may be subjected to dry granulation, e.g., via compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps. In some embodiments, the active agent(s) of the present invention formulation is dry granulated with other excipients in the pharmaceutical formulation. In other embodiments, the active agent(s) of the present invention formulation is added to other excipients of the pharmaceutical formulation after they have been dry granulated.

In other embodiments, the formulation of the present invention formulations described herein is a solid dispersion. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl. 2004/0013734, each of which is specifically incorporated by reference. In some embodiments, the solid dispersions of the invention comprise both amorphous and non-amorphous the active agent(s) of the present invention and can have enhanced bioavailability as compared to conventional the active agent(s) of the present invention formulations. In still other embodiments, the active agent(s) of the present invention formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

The pharmaceutical solid oral dosage forms comprising the active agent(s) of the present invention described herein can be further formulated to provide a modified or controlled release of the active agent(s) of the present invention. In some embodiments, the solid dosage forms described herein can be formulated as a delay release dosage form such as and enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated. Enteric coatings may also be used to prepare other controlled release dosage forms including extended release and pulsatile release dosage forms.

In other embodiments, the active agent(s) of the formulations described herein are delivered using a pulsatile dosage form. Pulsatile dosage forms comprising the active agent(s) of the present invention formulations described herein may be administered using a variety of formulations known in the art. For example, such formulations include, but are not limited to, those described in U.S. Pat. Nos. 5,011,692, 5,017,381, 5,229,135, and 5,840,329, each of which is specifically incorporated by reference. Other dosage forms suitable for use with the active agent(s) of the present invention formulations are described in, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form comprising at least two groups of particles, each containing active agent(s) of the present invention as described herein. The first group of particles provides a substantially immediate dose of the active agent(s) of the present invention upon ingestion by a subject. The first group of particles can be either uncoated or comprise a coating and/or sealant. The second group of particles comprises coated particles, which comprise from about 2% to about 75%, preferably from about 2.5% to about 70%, and more preferably from about 40% to about 70%, by weight of the total dose of the active agent(s) of the present invention in said formulation, in admixture with one or more binders. The coating comprises a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD 100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the active agent(s) of the present invention formulation.

Many other types of controlled release systems known to those of ordinary skill in the art and are suitable for use with the active agent(s) of the present invention formulations described herein. Examples of such delivery systems include, e.g., polymer-based systems, such as polylactic and polyglycolic acid, polyanhydrides and polycaprolactone, cellulose derivatives (e.g., ethyl cellulose), porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference. In some embodiments, materials include shellac, acrylic polymers, cellulosic derivatives, polyvinyl acetate phthalate, and mixtures thereof. In other embodiments, materials include Eudragit® series E, L, RL, RS, NE, L, L300, S, 100-55, cellulose acetate phthalate, Aquateric, cellulose acetate trimellitate, ethyl cellulose, hydroxypropylmethylcellulose phthalate, hydroxypropylmethylcellulose acetate succinate, polyvinyl acetate phthalate, and Cotteric.

The controlled release systems may utilize a hydrophilic polymer, including but not limited to a water swellable polymer (e.g., a natural or synthetic gum). The hydrophilic polymer may be any pharmaceutically acceptable polymer which swells and expands in the presence of water to slowly release the active agent(s) of the present invention. These polymers include polyethylene oxide, methylcellulose, hydroxypropylcellulose, hydroxypropylmethylcellulose and the like. In a preferred embodiment, the water swellable polymer will be polyethylene oxide (obtained from Union Carbide Corporation under the trade name Polyox WSR Coagulant or Polyox WSR N 80). These materials form a viscous gel in water or other solvent system at a sufficient concentration to control the release of the active agent(s) of the present invention. This will generally require a concentration of the pharmaceutically acceptable, water swellable polymer of about 0-50% by weight of the compressed, uncoated tablet.

The performance of acrylic polymers (primarily their solubility in biological fluids) can vary based on the degree and type of substitution. Examples of suitable acrylic polymers include methacrylic acid copolymers and ammonia methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Opadry Enteric are also insoluble in stomach and dissolve in the intestine.

Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP psuedolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HP-MCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

In some embodiments, formulations are provided comprising the active agent(s) of the present invention particles described herein and at least one dispersing agent or suspending agent for oral administration to a subject. The formulation may be a powder and/or granules for suspension, and upon admixture with water, a substantially uniform suspension is obtained. As described herein, the aqueous dispersion can comprise amorphous and non-amorphous the active agent(s) of the present invention particles of consisting of multiple effective particle sizes such that the active agent(s) of the present invention particles having a smaller effective particle size are absorbed more quickly and the active agent(s) of the present invention particles having a larger effective particle size are absorbed more slowly. In certain embodiments the aqueous dispersion or suspension is an immediate release formulation. In another embodiment, an aqueous dispersion comprising amorphous the active agent(s) of the present invention particles is formulated such that a portion of the active agent(s) of the present invention particles are absorbed within, e.g., about 3 hours after administration and about 90% of the active agent(s) of the present invention particles are absorbed within, e.g., about 10 hours after administration. In other embodiments, addition of a complexing agent to the aqueous dispersion results in a larger span of the active agent(s) of the present invention containing particles to extend the drug absorption phase such that 50-80% of the particles are absorbed in the first 3 hours and about 90% are absorbed by about 10 hours. Dosage forms for oral administration can be aqueous suspensions selected from the group including, but not limited to, pharmaceutically acceptable aqueous oral dispersions, emulsions, solutions, and syrups. See, e.g., Singh et al., Encyclopedia of Pharmaceutical Technology, 2nd Ed., pp. 754-757 (2002). In addition to the active agent(s) of the present invention particles, the liquid dosage forms may comprise additives, such as: (a) disintegrating agents; (b) dispersing agents; (c) wetting agents; (d) at least one preservative, (e) viscosity enhancing agents, (f) at least one sweetening agent, and (g) at least one flavoring agent.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethylcellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben) and their salts, benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion can comprise methylparaben and propylparaben in a concentration ranging from about 0.01% to about 0.3% methylparaben by weight to the weight of the aqueous dispersion and about 0.005% to about 0.03% propylparaben by weight to the total aqueous dispersion weight. In yet another embodiment, the aqueous liquid dispersion can comprise methylparaben from about 0.05 to about 0.1 weight % and propylparaben from about 0.01 to about 0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity enhancing agent will depend upon the agent selected and the viscosity desired.

Examples of natural and artificial sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.0001% to about 10.0% the weight of the aqueous dispersion. In another embodiment, the aqueous liquid dispersion can comprise a sweetening agent or flavoring agent in a concentration ranging from about 0.0005% to about 5.0% wt % of the aqueous dispersion. In yet another embodiment, the aqueous liquid dispersion can comprise a sweetening agent or flavoring agent in a concentration ranging from about 0.0001% to 0.1 wt %, from about 0.001% to about 0.01 weight %, or from 0.0005% to 0.004% of the aqueous dispersion.

In addition to the additives listed above, the liquid the active agent(s) of the present invention formulations can also comprise inert diluents commonly used in the art, such as water or other solvents, solubilizing agents, and emulsifiers.

In some embodiments, formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art include, but are not limited to, for example, U.S. Pat. Nos. 5,858,401, 6,667,048, and 6,960,563, each of which is specifically incorporated by reference. Exemplary emulsifiers are ethyl alcohol, isopropyl alcohol, ethyl carbonate, ethyl acetate, benzyl alcohol, benzyl benzoate, propylene glycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In certain embodiments, the active agent(s) may be administered via Intranasal formulations which are known in the art and are described in, for example, U.S. Pat. Nos. 4,476,116, 5,116,817 and 6,391,452, each of which is specifically incorporated by reference. The active agent(s) of the present invention prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, complexing agents or buffering and other stabilizing and solubilizing agents may also be present. Preferably, the nasal dosage form should be isotonic with nasal secretions.

In certain embodiments, the active agent(s) may be administered via buccal formulations such as, but are not limited to, U.S. Pat. Nos. 4,229,447, 4,596,795, 4,755,386, and 5,739,136, each of which is specifically incorporated by reference. In addition, the buccal dosage forms described herein can further comprise a bioerodible (hydrolyzable) polymeric carrier that may also serves to adhere the dosage form to the buccal mucosa. The buccal dosage form is fabricated so as to erode gradually over a predetermined time period, wherein the active agent(s) of the present invention delivery is provided essentially throughout. Buccal drug delivery, as will be appreciated by those skilled in the art, avoids the disadvantages encountered with oral drug administration, e.g., slow drug absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not comprised, and the carrier is compatible with the active agent(s) of the present invention and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like.

In certain embodiments, the active agent(s) may be administered via transdermal formulations using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety. In some embodiments, the transdermal delivery device used with the active agent(s) of the present invention described herein can comprise a power source, radio frequency, or a brief electrical current to micro-electrodes in the skin creating "channels" or "pores" in the stratum corneum to facilitate the delivery of the active agent(s) of the present invention formulation, such methods are known in the art and are described in, for example U.S. Pat. Nos. 6,611,706, 6,708,060, and 6,711,435, each of which is specifically incorporated by reference in its entirety. In other embodiments, the transdermal delivery device can comprise a means for porating the stratum corneum, e.g., micro-lancing, application of sonic energy, or hydraulic puncturing, to facilitate the delivery of the active agent(s) of the present invention, such methods are known in the art and are described in, for example, U.S. Pat. Nos. 6,142,939 and 6,527,716, each of which is specifically incorporated by reference in its entirety. The pores described by the methods herein are typically about 20-50 microns in depth and to not extend into areas of innervation or vascularization.

The transdermal dosage forms described herein may incorporate certain pharmaceutically acceptable excipients which are conventional in the art. In general, the transdermal formulations described herein comprise at least three components: (1) the active agent(s) of the present invention; (2) a penetration enhancer; and (3) an aqueous adjuvant. In addition, transdermal formulations can include additional components such as, but not limited to, gelling agents, creams and ointment bases, and the like. In some embodiments, the transdermal formulation can further comprise a woven or non-woven backing material to enhance drug absorption and prevent the removal of the transdermal formulation from the skin. In other embodiments, the transdermal formulations described herein can maintain a saturated or supersaturated state to promote diffusion into the skin.

The active agent(s) of the present invention formulations suitable for intramuscular, subcutaneous, or intravenous injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethylene-glycol, glycerol, cremophor and the like), suitable mixtures thereof, vegetable oils (such as olive oil) and injectable organic esters such as ethyl oleate. Additionally, the active agent(s) of the present invention can be dissolved at concentrations of >1 mg/ml using water soluble beta cyclodextrins (e.g. beta-sulfobutyl-cyclodextrin and 2-hydroxypropylbetacyclodextrin. Proper fluidity can be maintained, for example, by the use of a coating such as lecithin, by the maintenance of the required particle size in the case of dispersions, and by the use of surfactants. The active agent(s) of the present invention formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. The active agent(s) of the present invention suspension formulations designed for extended release via subcutaneous or intramuscular injection can avoid first pass metabolism and lower dosages of the active agent(s) of the present invention will be necessary to maintain plasma levels of about 50 ng/ml. In such formulations, the particle size of the active agent(s) of the present invention particles and the range of the particle sizes of the active agent(s) of the present invention particles can be used to control the release of the drug by controlling the rate of dissolution in fat or muscle.

The particular choice of active agents used will depend upon the diagnosis of the attending physicians and their judgment of the condition of the patient and the appropriate treatment protocol. Each of the active agents may be administered concurrently (e.g., simultaneously, essentially simultaneously or within the same treatment protocol) or sequentially, depending upon the nature of the proliferative disease, the condition of the patient, and the actual choice of compounds used. The determination of the order of administration, and the number of repetitions of administration of each active agent during a treatment protocol, is well within the knowledge of the skilled physician after evaluation of the disease being treated and the condition of the patient.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

DETAILED DESCRIPTION OF THE PREFERRED EMBODIMENTS

A unique combination of entry criteria for metabolic syndrome patients based on the guidelines recommended by the American Association of Clinical Endocrinologists will be used to select patients which would include moderate risk (MR) as well as high risk (HR) which would include: A1c > or =6.5, BMI > or =27 Kg/m2 (MR), BMI >=40 Kg/m2 (HR), Fasting plasma glucose (FPG) > or =126 mg/dL, 2 hour GTT (Glucose tolerance test) > or =200 mg/dL, non-fasting laboratory glucose > or =200 mg/dL, LDL-C > or =100 mg/dL, TG > or =150 mg/dL, non HDL-C > or =130 mg/dL, HDL-C < or =40 mg/dL, TC/HDL-C > or =3.5, ApoB > or =90 mg/dL, B.P. (blood pressure) > or =130/80 mm Hg. Other symptoms such as polydipsia, polyurea and/or polyphagia will also be considered.

In addition to the entry criteria, a set of risk stratification criteria will be used which would include or exclude patients which may contain: lack of adequate therapeutic and overall clinical benefit from previously prescribed mono- and combination therapies, BMI (BMI > or =27 Kg/m2), Age (> or =45 yrs), elevated B.P. (> or =130/80 mm Hg), abdominal adiposity (prototypical and/or pear-shaped), cigarette smoking, hsCRP > or =2.0, excessive alcohol intake, family history of Type II diabetes, family history of coronary heart disease (CHD), pancreatis or hepatitis, chronic kidney disease or pre-existing renal impairment (Creatinine level > or =1.5 mg/dL in males and > or =1.4 mg/dL in females; eGFR (estimated glomerular filtration rate) < or =60 ml/min/1.73 m2), recent change in body weight (> or =5%), abnormal liver test (ALT > or =40), previous use of ACE inhibitors or ARBs etc.

All drug combinations will be titrated individually and in combinations for efficacy and safety in appropriate Type II diabetes and metabolic syndrome pre-clinical in vivo models. Final doses of drugs, FDC combinations and number of administrations daily depends on the patient's response and tolerance. The optimal dosage, FDC combination of drugs and modified release kinetics will be determined based on the overall desired clinical effect with minimal adverse side effects. Doses will be reduced or adjusted for patients' risk stratification criteria e.g. renal impairment.

The following examples illustrate various aspects of the present invention. They are not to be construed to limit the claims in any manner whatsoever.

EXAMPLE 1

Anti-inflammatory-Centric FDC Formulations
(Type II Diabetes Drugs): Two Drug Combinations
(IR & IR)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form in combination with anti-type II diabetes drugs such as Sulfonyl ureas such as 125 mg to 500 mg Chloropropamide or 125 mg to 500 mg Tolbutamide or 50 to 250 mg Tolazamide or 1.25 mg to 0.5 mg to 15 mg Glipizide or 0.5 mg to 20 mg Glyburide or 0.5 mg to 8 mg Glimepiride; or Biguanides such as 250 mg to 2000 mg Metformin; or Thiozolidinediones (TZDs) such as 7.5 mg to 30 mg Pioglitazone or 2 mg to 8 mg Rosiglitazone; or alpha glucosidase inhibitors such as 25 mg to 100 mg Acarbose or 12.5 mg 100 mg Miglitol; or DPPIV inhibitors such as 12.5 mg to 100 mg Sitagliptin, 3 mg to 25 mg Alogliptin or 2.5 mg Linagliptin; or SGLT-2 (Sodium Glucose co-transporters) inhibitors such as 2.5 mg to 10 mg Dapagliflozin or 50 to 300 mg Canagliflozin formulated in an IR form.

EXAMPLE 2

Anti-inflammatory-Centric FDC Formulations
(Type II Diabetes Drugs): Two Drug Combinations
(IR & ER)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form in combination with anti-type II diabetes drugs such as Sulfonyl ureas such as 500 mg Chloropropamide or 500 mg Tolbutamide or 100 mg Tolazamide or 20 mg Glipizide or 10 mg Glyburide or 8 mg Glimepiride; or Biguanides such as 500 mg Metformin; or Thiozolidinediones (TZDs) such as 30 mg Pioglitazone or 8 mg Rosiglitazone; or alpha glucosidase inhibitors such as 100 mg Acarbose or 100 mg Miglitol; or DPP-IV inhibitors such as 250 mg Sitagliptin, 25 mg Alogliptin or 10 mg Linagliptin; or SGLT-2 (Sodium Glucose co-transporters) inhibitors such as 25 mg Dapagliflozin or 300 mg Canagliflozin in an ER form.

EXAMPLE 2

Anti-inflammatory-Centric FDC Formulations
(Type II Diabetes Drugs): Two Drug Combinations
(IR & DR)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form in combination with anti-type II diabetes drugs such as Sulfonyl ureas such as 125 mg to 500 mg Chloropropamide or 125 mg to 500 mg Tolbutamide or 50 to 250 mg Tolazamide or 1.25 mg to 0.5 mg to 15 mg Glipizide or 0.5 mg to 20 mg Glyburide or 0.5 mg to 8 mg Glimepiride; or Biguanides such as 250 mg to 2000 mg Metformin; or Thiozolidinediones (TZDs) such as 7.5 mg to 30 mg Pioglitazone or 2 mg to 8 mg Rosiglitazone; or alpha glucosidase inhibitors such as 25 mg to 100 mg Acarbose or 12.5 mg 100 mg Miglitol; or DPPIV inhibitors such as 12.5 mg to 100 mg Sitagliptin, 3 mg to 25 mg Alogliptin or 2.5 mg Linagliptin; or SGLT-2 (Sodium Glucose co-transporters) inhibitors such as 2.5 mg to 10 mg Dapagliflozin or 50 to 300 mg Canagliflozin formulated in an IR form.

EXAMPLE 3

Three Drug Combinations (IR/IR/ER):
Anti-inflammatory/Sulfonyl Urea/Biguanides 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form in combination with anti-type II diabetes drugs such as Sulfonyl ureas such as 125 mg to 500 mg Chloropropamide or 125 mg to 500 mg Tolbutamide or 50 to 250 mg Tolazamide or 1.25 mg to 0.5 mg to 15 mg Glipizide or 0.5 mg to 20 mg Glyburide or 0.5 mg to 8 mg Glimepiride in an IR form and Biguanides such as 250 mg to 2000 mg Metformin in an ER form.

EXAMPLE 4

Celecoxib/Metformin (IR/IR)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an IR form.

EXAMPLE 5

Celecoxib/Metformin (IR/ER)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an ER form.

EXAMPLE 6

Celecoxib/Metformin (IR/ER)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an IR as well as an ER form.

EXAMPLE 7

Celecoxib/Metformin (IR/IR/DR)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an IR as well as DR form.

EXAMPLE 8

Celecoxib/Metformin (IR/ER/DR)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an ER as well as DR form.

EXAMPLE 9

Celecoxib/Valsartan (IR/DR)

50 mg to 400 mg of Celecoxib (an anti-inflammatory drug) formulated in an IR form in combination with 40 mg to 320 mg Valsartan (an ARB) in a DR form.

EXAMPLE 10

Celecoxib/Valsartan (IR/ER)

50 mg to 400 mg of Celecoxib (an anti-inflammatory drug) formulated in an IR form in combination with 40 mg to 320 mg Valsartan (an ARB) in an ER form.

EXAMPLE 11

Three Drug Combinations (IR/IR/ER):
Anti-inflammatory/DPP-IV Inhibitors/Biguanides 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form in combination with anti-type II diabetes drugs such as 500 mg Metformin in an IR form with DPP-IV inhibitors such as 12.5 mg to 100 mg Sitagliptin, 3 mg to 25 mg Alogliptin or 2.5 mg Linagliptin in an IR form along with Biguanides such as 250 mg to 2000 mg Metformin in an ER form.

EXAMPLE 12

Three Drug Combinations (IR/IR/ER):
Anti-inflammatory/SGLT-2 Inhibitors/Biguanides 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form in combination with anti-type II diabetes drugs such as SGLT-2 (Sodium Glucose co-transporters) inhibitors such as 2.5 mg to 10 mg Dapagliflozin or 50 to 300 mg Canagliflozin formulated in an IR form along with Biguanides such as 500 mg Metformin in an ER form.

EXAMPLE 13

Three Drug Combinations (IR/IR/DR):
Anti-inflammatory/DPP-IV Inhibitors/SGLT-2 Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form in combination with anti-type II diabetes drugs such as 500 mg Metformin in an IR form with DPPIV inhibitors such as 12.5 mg to 100 mg Sitagliptin, 3 mg to 25 mg Alogliptin or 2.5 mg Linagliptin in an IR form along with SGLT-2 (Sodium Glucose co-transporters) inhibitors like 5 mg Dapagliflozin or 100 mg Canagliflozin in a DR form administered once or twice a day (b.i.d).

EXAMPLE 14

Celecoxib/Metformin/Valsartan (IR/IR/DR)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an IR form and 40 mg to 320 mg Valsartan (an ARB) in a DR form.

EXAMPLE 15

Celecoxib/Metformin/Valsartan (IR/ER/DR)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an ER form and 40 mg to 320 mg Valsartan (an ARB) in a DR form.

EXAMPLE 16

Celecoxib/Metformin/Valsartan (IR/ER & DR/DR)

50 mg to 400 mg of Celecoxib (an anti-inflammatory drug) formulated in an IR form in combination with 250 mg to 2000 mg of Metformin, a biguanide (anti-Type II diabetes or anti-hyperglycemic drug) in an ER as well as a DR form and 40 mg to 320 mg Valsartan (an ARB) in a DR form.

EXAMPLE 17

Biguanide/Valsartan/Celecoxib (IR/IR/DR)

250 mg to 2000 mg of Metformin, a biguanide (anti-Type II diabetes or anti-hyperglycemic drug) in an IR form and 40 mg to 320 mg Valsartan (an ARB) in an IR form and 50 mg to 400 mg of Celecoxib (an anti-inflammatory drug) in a DR form.

EXAMPLE 18

Metformin/Valsartan/Celecoxib (ER/IR/DR)

250 mg to 2000 mg of Metformin, a biguanide (anti-Type II diabetes or anti-hyperglycemic drug) in an ER form and 40 mg to 320 mg Valsartan (an ARB) in an IR form and 50 mg to 400 mg of Celecoxib (an anti-inflammatory drug) in a DR form.

EXAMPLE 19

Celecoxib/Metformin/Valsartan (IR & ER/ER/DR)

50 mg to 400 mg of Celecoxib (an anti-inflammatory drug) formulated in an IR as well as in an ER form in combination with 250 mg to 2000 mg of Metformin, a biguanide (anti-Type II diabetes or anti-hyperglycemic drug) in an ER as well as a DR form and 40 mg to 320 mg Valsartan (an ARB) in a DR form.

EXAMPLE 20

Four Drug Combinations (IR/IR/ER/DR):
Anti-inflammatory/DPP-IV Inhibitors/Biguanides/SGLT-2 Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with anti-type II diabetes drugs such as DPP-IV inhibitors such as 12.5 mg to 100 mg Sitagliptin, 3 mg to 25 mg Alogliptin or 2.5 mg Linagliptin in an IR form in combination with Biguanides such as 500 mg Metformin in an ER form along with SGLT-2 (Sodium Glucose co-transporters) inhibitors like 5 mg Dapagliflozin or 100 mg Canagliflozin in a DR form administered once or twice a day (b.i.d).

EXAMPLE 21

Combination of 2-4 Drug Combinations with Incretin Mimetics

Two to four drug combinations described above can be combined with sub-cutaneous administration (S.C.) Incretin mimetics such as 5 ug Exenatide or 0.65 mg-1.8 mg Liraglutide (Victoza).

EXAMPLE 22

Combination of 2-4 Drug Combinations with TZDs (Glitazones)

Two drug combinations (IR/DR): Anti-inflammatory/glitazones; 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in an IR form in combination with anti-Type II diabetes drugs such as 30 mg Pioglitazone or 8 mg Rosiglitazone in a DR form.

Three drug combinations (IR/IR/DR): Anti-inflammatory/Biguanides/TZDs (Thiozolidinediones) or glitazones; 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in an IR form in combination with anti-Type II diabetes drugs such as 500 mg to 1000 mg Metformin in an IR form with TZDs such as 30 mg Pioglitazone or 8 mg Rosiglitazone in a DR form.

Three drug combinations (IR/IR/DR): Anti-inflammatory/SGLT-2 inhibitors/glitazones; 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in an IR form in combination with anti-Type II diabetes drugs such as 25 mg Dapagliflozin or 300 mg Canagliflozin in an IR form with TZDs such as 30 mg Pioglitazone or 8 mg Rosiglitazone in a DR form.

Three drug combinations (IR/IR/DR): Anti-inflammatory/DPP-IV inhibitors/glitazones; 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in an IR form in combination with anti-Type II diabetes drugs such as 250 mg Sitagliptin or 25 mg Alogliptin or 10 mg Linagliptin in an IR form with TZDs such as 30 mg Pioglitazone or 8 mg Rosiglitazone in a DR form.

Four drug combinations (IR/IR/ER/DR): Anti-inflammatory/SGLT-2 inhibitors/Biguanides/Glitazones; 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in an IR form in combination with anti-Type II diabetes drugs such as 25 mg Dapagliflozin or 300 mg Canagliflozin in an IR form with 500 mg to 1000 mg Metformin in an ER form TZDs such as 30 mg Pioglitazone or 8 Rosiglitazone in a DR form.

Four drug combinations (IR/IR/ER/DR): Anti-inflammatory/DPP-IV inhibitors/Biguanides/Glitazones; 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in an IR form in combination with anti-Type II diabetes drugs such as 250 mg Sitagliptin or 25 mg Alogliptin or 10 mg Linagliptin in an IR form with 500 mg to 1000 mg Metformin in an ER form TZDs such as 30 mg Pioglitazone or 8 mg Rosiglitazone in a DR form.

EXAMPLE 23

Lipid Lowering Drugs: Two Drug Combinations (IR/IR)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Statins such as 5 mg-80 mg Atorvastatin or 10 mg to 80 mg Fluvastatin or 5 mg to 80 mg Lovastatin or 20 mg to 80 mg Provastatin or 2.5 mg to 40 mg Rosuvastatin or 2.5 mg to 40 mg Simvastatin; or Nicotinic acids (Niacin) such as 250 mg to 500 mg Nicolar or 250 mg to 500 mg Niaspan; or Fibrates such as 24 to 145 mg Tricor or 500 mg to 1200 mg Lopid or 2.5 mg to 10 mg Ezetimide and administered once or twice daily depending on patients response and tolerance.

EXAMPLE 24

Lipid Lowering Drugs: Two Drug Combinations (IR/ER)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Statins such as 80 mg Atorvastatin or 80 mg Provastatin or 40 mg Rosuvastatin or 40 mg Simvastatin; or Niacins such as 500 mg to 2000 mg Nicolar or 500 mg to 2000 mg Niaspan; Fibrates such as 145 mg Tricor or 600 mg to 1200 mg Lopid formulated in the ER form.

EXAMPLE 25

Lipid Lowering Drugs: Three Drug Combinations (IR/IR/ER): Anti-inflammatory/Statins/Niacin 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Statins such as 5 mg-80 mg Atorvastatin or 10 mg to 80 mg Fluvastatin or 5 mg to 80 mg Lovastatin or 20 mg to 80 mg Provastatin or 2.5 mg to 40 mg Rosuvastatin or 2.5 mg to 40 mg Simvastatin formulated in the IR form will be combined with Nicotinic acids such as 500 mg to 2000 mg Nicolar or 500 mg to 2000 mg Niaspan formulated in the ER form.

EXAMPLE 26

Lipid Lowering Drugs: Three Drug Combinations
(IR/IR/ER): Anti-inflammatory/Statins/Fibrates 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Statins such as 5 mg-80 mg Atorvastatin or 10 mg to 80 mg Fluvastatin or 5 mg to 80 mg Lovastatin or 20 mg to 80 mg Provastatin or 2.5 mg to 40 mg Rosuvastatin or 2.5 mg to 40 mg Simvastatin formulated in the IR form will be combined with Fibrates such as 145 mg Tricor or 600 mg to 1200 mg Lopid formulated in the ER form.

EXAMPLE 27

Lipid Lowering Drugs: Three Drug Combinations
(IR/IR/ER): Anti-inflammatory/Niacins/Statins 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Niacins such as 500 mg to 2000 mg Nicolar or 500 mg to 2000 mg Niaspan formulated in the IR form will be combined with Statins such as 80 mg Atorvastatin or 80 mg Provastatin or 40 mg Rosuvastatin or 40 mg Simvastatin formulated in the ER form.

EXAMPLE 28

Lipid Lowering Drugs: Three Drug Combinations
(IR/IR/DR): Anti-inflammatory/Fibrates/Statins 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Fibrates such as 24 to 145 mg Tricor or 500 mg to 1200 mg Lopid or 2.5 mg to 10 mg Ezetimide formulated in the IR form will be combined with Statins such as 80 mg Atorvastatin or 80 mg Provastatin or 40 mg Rosuvastatin or 40 mg Simvastatin formulated in the ER form.

EXAMPLE 29

Lipid Lowering Drugs: Four Drug Combinations
(IR/IR/ER/DR):
Anti-inflammatory/Statins/Niacins/Fibrates 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Statins such as 5 mg-80 mg Atorvastatin or 10 mg to 80 mg Fluvastatin or 5 mg to 80 mg Lovastatin or 20 mg to 80 mg Provastatin or 2.5 mg to 40 mg Rosuvastatin or 2.5 mg to 40 mg Simvastatin formulated in the IR form with Niacins such as 500 mg to 2000 mg Nicolar or 500 mg to 2000 mg Niaspan formulated in the ER form will be combined with Fibrates such as 24 to 145 mg Tricor or 500 mg to 1200 mg Lopid or 2.5 mg to 10 mg Ezetimide formulated in the DR form.

EXAMPLE 17

Anti-inflammatory/Anti-Hypertensive Drugs: Two
Drug Combinations (IR/IR)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone; or Beta blockers such as 0.5 mg to 60 mg Timolol or 1.25 mg to 10 mg Cartelol Hydrochloride or 1.5 mg to 50 mg Corredilol or 20 mg to 640 mg Propranodol or 2.5 mg to 40 mg Betaxolol or 10 mg to 80 mg Penbutolol Sulfate or 50 mg to 450 mg Metoprolol or 100 mg to 1200 mg Acebutolol or 25 mg to 200 mg Atenolol or 2.5 mg to 20 mg Pindolol or 50 mg to 2400 mg Labetolol; Alpha blockers such as 0.5 mg to 16 mg Doxazocin or 0.5 mg to 20 mg Terazocin or 0.5 mg to 20 mg Prazocin; Angiotensin-converting enzyme (ACE) inhibitors such as 0.5 mg to 80 mg Quinapril or 1.25 mg to 20 mg Ramipril or 12.5 mg to 450 mg Captopril or 0.5 mg to 8 mg Trandolapril or 5 mg to 40 mg Benazepril or 5 mg to 80 mg Fosinopril or 0.5 mg to 80 mg Lisinopril or 5 mg to 60 mg Moexipril or 1.25 mg to 40 mg Enalapril; or Angiotensin II Receptor Blockers (ARBs) such as 2 mg to 32 mg Candesartan or 75 mg to 300 mg Irbesartan or 10 mg to 40 mg Olmesartan or 12.5 mg to Losartan or 40 mg to 320 mg Valsartan or 10 mg to 80 mg Telmisartan or 200 mg to 800 mg Eprosartan; or Calcium Channel Blockers (CCBs) such as 15 mg to 60 mg Nifedipine or 15 mg to 60 mg Diltiazem or 1.25 mg to 10 mg Amlodipine or 1.25 mg to 60 mg of other CCBs (e.g. Verampil, Nicardipine, Isradipine, Felodipine or Nisoldipine); Central Agonists such as 125 mg to 2000 mg Methyldopa or 0.05 mg to 2.4 mg Clonidine or 0.5 mg to 3 mg Guanfacine or 2 mg to 32 mg Guanbenz; or Peripheral-acting Adrenergic blockers such as 5 mg to 75 mg Guanadrel or 5 mg to 50 mg Guanethidine or 0.05 mg to 1 mg Reserpine; or Direct Vasodilators such as 5 mg to 300 mg Hydralazine or 2.5 mg to 100 mg Minoxidil; or Direct Renin Inhibitors such as 75 mg to 300 mg Tekturana formulated in the IR form.

EXAMPLE 30

Anti-inflammatory/Anti-Hypertensive Drugs: Two
Drug Combinations (IR/ER)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Diuretics such as 200 mg to 400 mg Spiranolactone or 50 mg to 100 mg Triampterene or 50 mg to 100 mg Hydrochlorothiazide (HCTZ) or 50 mg to 100 mg Chlorthalidone or 100 mg to 600 mg Furosemide or 2.5 mg to 5 mg Amiloride Hydrochloride or 1 mg to 2.5 mg Metolazone; or Beta blockers such as 10 mg to 60 mg Timolol or 2.5 mg to 10 mg Cartelol Hydrochloride or 5 mg to 50 mg Corredilol or 100 mg to 640 mg Propranolol or 10 mg to 40 mg Betaxolol or 50 mg to 80 mg Penbutolol Sulfate or 250 mg to 450 mg Metoprolol or 250 mg to 1200 mg Acebutolol or 100 mg to 200 mg Atenolol or 10 mg to 20 mg Pindolol or 250 mg to 2400 mg Labetolol; Alpha blockers such as 2.5 mg to 16 mg Doxazocin or 2.5 mg to 20 mg Terazocin or 2.5 mg to 20 mg Prazocin; Angiotensin-converting enzyme (ACE) inhibitors such as 5 mg to 80 mg Quinapril or 2.5 mg to 20 mg Ramipril or 50 mg to 450 mg Captopril or 2.5 mg to 8 mg Trandolapril or 15 mg to 40 mg Benazepril or 25 mg to 80 mg Fosinopril or 5 mg to 80 mg Lisinopril or 15 mg to 60 mg Moexipril or 5 mg to 40 mg Enalapril; or Angiotensin II Receptor Blockers (ARBs) such as 10 mg to 32 mg Candesartan or 150 mg to 300 mg Irbesartan or 25 mg to 40 mg Olmesartan or 25 mg to Losartan or 100 mg to 320 mg Valsartan or 25 mg to 80 mg Telmisartan or 250 mg to 800 mg Eprosartan; or Calcium Channel Blockers (CCBs) such as 25 mg to 60 mg Nifedipine or 25 mg to 60 mg Diltiazem or 5.0 mg to 10 mg Amlodipine or 5 mg to 60 mg of other CCBs (e.g. Verampil, Nicardipine, Isradipine, Felodipine or Nisoldipine); Central Agonists such as 250 mg to 2000 mg Methyldopa or 0.1 mg to 2.4 mg Clonidine or 1.0 mg to 3 mg Guanfacine or 5 mg to 32 mg Guanabenz; or Peripheral-acting Adrenergic blockers such as 10 mg to 75 mg Guanadrel or 10 mg to 50 mg Guanethidine or 0.05 mg to 1 mg Reserpine; or Direct Vasodilators such as 25 mg to 300 mg Hydralazine or 5 mg to 100 mg Minoxidil; or Direct Renin Inhibitors such as 100 mg to 300 mg Tekturana formulated in the ER form.

EXAMPLE 31

Three Drug Combinations (IR/IR/ER):
Anti-inflammatory/Diuretics/Beta Blockers 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form combined with Beta blockers such as 10 mg to 60 mg Timolol or 2.5 mg to 10 mg Cartelol Hydrochloride or 5 mg to 50 mg Corredilol or 100 mg to 640 mg Propranolol or 10 mg to 40 mg Betaxolol or 50 mg to 80 mg Penbutolol Sulfate or 250 mg to 450 mg Metoprolol or 250 mg to 1200 mg Acebutolol or 100 mg to 200 mg Atenolol or 10 mg to 20 mg Pindolol or 250 mg to 2400 mg Labetolol formulated in ER form.

EXAMPLE 32

Three Drug Combinations (IR/IR/ER):
Anti-inflammatory/Beta Blockers/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Beta blockers such as 0.5 mg to 60 mg Timolol or 1.25 mg to 10 mg Cartelol Hydrochloride or 1.5 mg to 50 mg Corredilol or 20 mg to 640 mg Propranolol or 2.5 mg to 40 mg Betaxolol or 10 mg to 80 mg Penbutolol Sulfate or 50 mg to 450 mg Metoprolol or 100 mg to 1200 mg Acebutolol or 25 mg to 200 mg Atenolol or 2.5 mg to 20 mg Pindolol or 50 mg to 2400 mg Labetolol formulated in the IR form and combined with Diuretics such as 200 mg to 400 mg Spiranolactone or 50 mg to 100 mg Triampterene or 50 mg to 100 mg Hydrochlorothiazide (HCTZ) or 50 mg to 100 mg Chlorthalidone or 100 mg to 600 mg Furosemide or 2.5 mg to 5 mg Amiloride Hydrochloride or 1 mg to 2.5 mg Metolazone formulated in the ER form.

EXAMPLE 33

Three Drug Combinations (IR/IR/ER):
Anti-inflammatory/Diuretics/ACE Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form will be combined with ACE inhibitors such as 5 mg to 80 mg Quinapril or 2.5 mg to 20 mg Ramipril or 50 mg to 450 mg Captopril or 2.5 mg to 8 mg Trandolapril or 15 mg to 40 mg Benazepril or 25 mg to 80 mg Fosinopril or 5 mg to 80 mg Lisinopril or 15 mg to 60 mg Moexipril or 5 mg to 40 mg Enalapril formulated in the form of ER.

EXAMPLE 34

Three Drug Combinations (IR/IR/ER):
Anti-inflammatory/ACE Inhibitors/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in IR form with ACE inhibitors such as 0.5 mg to 80 mg Quinapril or 1.25 mg to 20 mg Ramipril or 12.5 mg to 450 mg Captopril or 0.5 mg to 8 mg Trandolapril or 5 mg to 40 mg Benazepril or 5 mg to 80 mg Fosinopril or 0.5 mg to 80 mg Lisinopril or 5 mg to 60 mg Moexipril or 1.25 mg to 40 mg Enalapril formulated in the IR form will be combined with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in the form of ER.

EXAMPLE 35

Three Drug Combinations (IR/IR/ER):
Anti-inflammatory/Diuretics/ARBs 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form will be combined with ARBs such as 2 mg to 32 mg Candesartan or 75 mg to 300 mg Irbesartan or 10 mg to 40 mg Olmesartan or 12.5 mg to Losartan or 40 mg to 320 mg Valsartan or 10 mg to 80 mg Telmisartan or 200 mg to 800 mg Eprosartan formulated in the ER form.

EXAMPLE 36

Three Drug Combinations (IR/IR/ER):
Anti-inflammatory/ARBs/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with (ARBs) such as 2 mg to 32 mg Candesartan or 75 mg to 300 mg Irbesartan or 10 mg to 40 mg Olmesartan or 12.5 mg to Losartan or 40 mg to 320 mg Valsartan or 10 mg to 80 mg Telmisartan or 200 mg to 800 mg Eprosartan formulated in the IR form will be combined with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in the form of ER.

EXAMPLE 37

Three Drug Combinations (IR/IR/ER):
Anti-inflammatory/Diuretics/CCBs 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form will be combined with (CCBs) such as 25 mg to 60 mg Nifedipine or 25 mg to 60 mg Diltiazem or 5.0 mg to 10 mg Amlodipine or 5 mg to 60 mg of other CCBs (e.g. Verampil, Nicardipine, Isradipine, Felodipine or Nisoldipine) formulated in the ER form.

EXAMPLE 38

Three Drug Combinations (IR/IR/ER):
Anti-inflammatory/CCBs/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with CCBs such as 15 mg to 60 mg Nifedipine or 15 mg to 60 mg Diltiazem or 1.25 mg to 10 mg Amlodipine or 1.25 mg to 60 mg of other CCBs (e.g. Verampil, Nicardipine, Isradipine, Felodipine or Nisoldipine) will be combined with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in the form of ER.

EXAMPLE 39

Three Drug Combinations (IR/IR/ER):
Anti-inflammatory/Diuretics/Central Agonists 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form will be combined with Central Agonists such as 250 mg to 2000 mg Methyldopa or 0.1 mg to 2.4 mg Clonidine or 1.0 mg to 3 mg Guanfacine or 5 mg to 32 mg Guanabenz formulated in the ER form.

EXAMPLE 40

Three Drug Combinations (IR/IR/ER):
Anti-inflammatory/Central Agonists/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Central Agonists such as 125 mg to 2000 mg Methyldopa or 0.05 mg to 2.4 mg Clonidine or 0.5 mg to 3 mg Guanfacine or 2 mg to 32 mg Guanabenz formulated in the IR form will be combined with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in the form of ER.

EXAMPLE 41

Three Drug Combinations (IR/IR/ER):
Anti-inflammatory/Peripheral-Acting Adrenergic Blockers/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Peripheral-acting Adrenergic blockers such as 10 mg to 75 mg Guanadrel or 10 mg to 50 mg Guanethidine or 0.05 mg to 1 mg Reserpine formulated in the IR form will be combined with Diuretics such as 200 mg to 400 mg Spiranolactone or 50 mg to 100 mg Triampterene or 50 mg to 100 mg Hydrochlorothiazide (HCTZ) or 50 mg to 100 mg Chlorthalidone or 100 mg to 600 mg Furosemide or 2.5 mg to 5 mg Amiloride Hydrochloride or 1 mg to 2.5 mg Metolazone formulated in the form of ER.

EXAMPLE 42

Three Drug Combinations (IR/IR/ER):
Anti-inflammatory/Diuretics/Peripheral-Acting Adrenergic Blockers 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form will be combined with Peripheral-acting Adrenergic blockers such as 10 mg to 75 mg Guanadrel or 10 mg to 50 mg Guanethidine or 0.05 mg to 1 mg Reserpine formulated in the ER form.

EXAMPLE 43

Three Drug Combinations (IR/IR/ER):
Anti-inflammatory/Diuretics/Direct Vasodilators 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form will be combined with Direct Vasodilators such as 25 mg to 300 mg Hydralazine or 5 mg to 100 mg Minoxidil formulated in the ER form or direct vasodilators such as 25 mg to 300 mg Hydralazine or 5 mg to 100 mg Minoxidil formulated in the ER form.

EXAMPLE 32

Three Drug Combinations (IR/IR/ER):
Anti-inflammatory/Direct Vasodilators/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Direct Vasodilators such as 5 mg to 300 mg Hydralazine or 2.5 mg to 100 mg Minoxidil formulated in the IR form will be combined with Diuretics such as 200 mg to 400 mg Spiranolactone or 50 mg to 100 mg Triampterene or 50 mg to 100 mg Hydrochlorothiazide (HCTZ) or 50 mg to 100 mg Chlorthalidone or 100 mg to 600 mg Furosemide or 2.5 mg to 5 mg Amiloride Hydrochloride or 1 mg to 2.5 mg Metolazone formulated in the form of ER.

EXAMPLE 44

Three Drug Combinations (IR/IR/ER):
Anti-inflammatory/Diuretics/Direct Renin Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in IR form will be combined with Direct Renin Inhibitors such as 100 mg to 300 mg Tekturana formulated in the ER form.

EXAMPLE 45

Three Drug Combinations (IR/IR/ER):
Anti-inflammatory/Direct Renin Inhibitors/Diuretics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Direct Renin Inhibitors such as 75 mg to 300 mg Tekturana formulated in the IR form will be combined with Diuretics such as 200 mg to 400 mg Spiranolactone or 50 mg to 100 mg Triampterene or 50 mg to 100 mg Hydrochlorothiazide (HCTZ) or 50 mg to 100 mg Chlorthalidone or 100 mg to 600 mg Furosemide or 2.5 mg to 5 mg Amiloride Hydrochloride or 1 mg to 2.5 mg Metolazone formulated in the form of ER.

EXAMPLE 46

Four Drug Combinations (IR/IR/ER/DR):
Anti-inflammatory/Diuretic/CCB/ACE Inhibitor 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with Diuretics such as 12.5 mg to 400 mg Spiranolactone or 25 mg to 100 mg Triampterene or 12.5 mg to 100 mg Hydrochlorothiazide (HCTZ) or 7.5 mg to 100 mg Chlorthalidone or 10 mg to 600 mg Furosemide or 0.5 mg to 5 mg Amiloride Hydrochloride or 0.25 mg to 2.5 mg Metolazone formulated in the IR form with Calcium Channel Blockers (CCBs) such as 25 mg to 60 mg Nifedipine or 25 mg to 60 mg Diltiazem or 5.0 mg to 10 mg Amlodipine or 5 mg to 60 mg of other CCBs (e.g. Verampil, Nicardipine, Isradipine, Felodipine or Nisoldipine) formulated in the ER form will be combined with ACE inhibitors such as 0.5 mg to 80 mg Quinapril or 1.25 mg to 20 mg Ramipril or 12.5 mg to 450 mg Captopril or 0.5 mg to 8 mg Trandolapril or 5 mg to 40 mg Benazepril or 5 mg to 80 mg Fosinopril or 0.5 mg to 80 mg Lisinopril or 5 mg to 60 mg Moexipril or 1.25 mg to 40 mg Enalapril formulated in the DR form.

EXAMPLE 47

Anti-Obesity: Two Drug Combinations (IR/IR)

200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 50 mg to 120 mg Xenical or 10 mg to 37.5 mg Phentermine or 5 mg to 10 mg Lorcaserin or 10 mg to 37.5 mg Phentermine formulated in the form of IR.

EXAMPLE 48

Two Drug Combinations (IR/ER):
Anti-Obesity/Anti-inflammatory 50 mg to 120 mg Xenical or 10 mg to 37.5 mg Phentermine or 5 mg to 10 mg Lorcaserin or 10 mg to 37.5 mg Phentermine formulated in the form of IR will be combined with 250 mg 500 mg Ibuprofen or 300 mg to 500 mg Aspirin-like drugs or 200 mg to 400 mg Celecoxib or 200 mg to 500 mg of Sulindac or other known anti-inflammatory drugs will be formulated in the form of ER.

EXAMPLE 49

Three Drug Combinations (IR/IR/ER):
Anti-inflammatory/Anti-Obesity/DPPIV Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 50 mg to 120 mg Xenical or 10 mg to 37.5 mg Phentermine or 5 mg to 10 mg Lorcaserin or 10 mg to 37.5 mg Phentermine formulated in the form of IR will be combined with DPP-IV inhibitors such as 250 mg Sitagliptin, 25 mg Alogliptin or 10 mg Linagliptin formulated in the ER form.

EXAMPLE 50

Three Drug Combinations (IR/IR/S.C. Injection):
Anti-inflammatory/Anti-obesity/Incretin Mimetics 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 50 mg to 120 mg Xenical or 10 mg to 37.5 mg Phentermine or 5 mg to 10 mg Lorcaserin or 10 mg to 37.5 mg Phentermine formulated in the form of IR will be combined with Subcutaneous (S.C.) injections of Incretin mimetics such as 5 ug Exenatide or 0.65 mg to 1.8 mg Liraglutide or 0.6 mg to 1.8 mg Victoza.

EXAMPLE 51

Prediabetes or Prevention of on-set of Type II
Diabetes Drugs: Two Drug Combinations (IR/IR):
Anti-inflammatory/ARBs or ACE Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with (ACE) inhibitors such as 0.5 mg to 80 mg Quinapril or 1.25 mg to 20 mg Ramipril or 12.5 mg to 450 mg Captopril or 0.5 mg to 8 mg Trandolapril or 5 mg to 40 mg Benazepril or 5 mg to 80 mg Fosinopril or 0.5 mg to 80 mg Lisinopril or 5 mg to 60 mg Moexipril or 1.25 mg to 40 mg Enalapril; or Angiotensin II Receptor Blockers (ARBs) such as 2 mg to 32 mg Candesartan or 75 mg to 300 mg Irbesartan or 10 mg to 40 mg Olmesartan or 12.5 mg to Losartan or 40 mg to 320 mg Valsartan or 10 mg to 80 mg Telmisartan or 200 mg to 800 mg Eprosartan formulated in the IR form.

EXAMPLE 52

Prediabetes or Prevention of on-set of Type II
Diabetes Drugs: Three Drug Combinations
(IR/IR/ER): Anti-inflammatory/ARBs/Metformin 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with (ARBs) such as 2 mg to 32 mg Candesartan or 75 mg to 300 mg Irbesartan or 10 mg to 40 mg Olmesartan or 12.5 mg to Losartan or 40 mg to 320 mg Valsartan or 10 mg to 80 mg Telmisartan or 200 mg to 800 mg Eprosartan formulated in the IR form will be combined with 500 mg to 2000 mg Metformin formulated in the ER form.

EXAMPLE 53

Prediabetes or Prevent or Delay the on-set of Type
II Diabetes Drugs: Three Drug Combinations
(IR/IR/ER): Anti-inflammatory/ACE
Inhibitors/Metformin 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with ACE inhibitors such as 0.5 mg to 80 mg Quinapril or 1.25 mg to 20 mg Ramipril or 12.5 mg to 450 mg Captopril or 0.5 mg to 8 mg Trandolapril or 5 mg to 40 mg Benazepril or 5 mg to 80 mg Fosinopril or 0.5 mg to 80 mg Lisinopril or 5 mg to 60 mg Moexipril or 1.25 mg to 40 mg Enalapril formulated in the IR form will be combined with 500 mg to 2000 mg Metformin formulated in the ER form.

EXAMPLE 54

Prediabetes or Prevention of on-set of Type II
Diabetes Drugs: Four Drug Combinations
(IR/IR/ER/DR):
Anti-inflammatory/ARBs/Metformin/ACE Inhibitor 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with (ARBs) such as 2 mg to 32 mg Candesartan or 75 mg to 300 mg Irbesartan or 10 mg to 40 mg Olmesartan or 12.5 mg to Losartan or 40 mg to 320 mg Valsartan or 10 mg to 80 mg Telmisartan or 200 mg to 800 mg Eprosartan formulated in the IR form with 500 mg to 2000 mg Metformin formulated in the ER form will be combined with ACE inhibitors such as 0.5 mg to 80 mg Quinapril or 1.25 mg to 20 mg Ramipril or 12.5 mg to 450 mg Captopril or 0.5 mg to 8 mg Trandolapril or 5 mg to 40 mg Benazepril or 5 mg to 80 mg Fosinopril or 0.5 mg to 80 mg Lisinopril or 5 mg to 60 mg Moexipril or 1.25 mg to 40 mg Enalapril formulated in the DR form.

EXAMPLE 55

FDC Formulations for Clinically Managing Insulin Resistance Syndrome or Metabolic Syndrome: Two Drug Combinations (IR/IR/ER): Anti-inflammatory/Metformin/Metformin 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 250 mg to 500 mg Metformin formulated in the IR form will be combined with 250 mg to 2000 mg Metformin formulated in the ER form.

EXAMPLE 56

FDC Formulations for Clinically Managing Insulin Resistance Syndrome or Metabolic Syndrome: Two Drug Combinations (IR/IR/DR): Anti-inflammatory/Metformin/Metformin 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 250 mg to 500 mg Metformin formulated in the IR form will be combined with 250 mg to 2000 mg Metformin formulated in the DR form.

EXAMPLE 57

FDC Formulations for Clinically Managing Insulin Resistance Syndrome or Metabolic Syndrome: Three Drug Combinations (IR/IR/ER): Anti-inflammatory/Metformin/Atorvastatin 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 250 mg to 500 mg Metformin formulated in the IR form will be combined with Statins such as 80 mg Atorvastatin or 80 mg Provastatin or 40 mg Rosuvastatin or 40 mg Simvastatin formulated in the ER form.

EXAMPLE 58

FDC Formulations for Clinically Managing Insulin Resistance Syndrome or Metabolic Syndrome: Three Drug Combinations (IR/IR/ER): Anti-inflammatory/Metformin/ACE Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 250 mg to 500 mg Metformin formulated in the IR form will be combined with ACE inhibitors such as 5 mg to 80 mg Quinapril or 2.5 mg to 20 mg Ramipril or 50 mg to 450 mg Captopril or 2.5 mg to 8 mg Trandolapril or 15 mg to 40 mg Benazepril or 25 mg to 80 mg Fosinopril or 5 mg to 80 mg Lisinopril or 15 mg to 60 mg Moexipril or 5 mg to 40 mg Enalapril formulated in the form of ER.

EXAMPLE 59

FDC Formulations for Clinically Managing Insulin Resistance Syndrome or Metabolic Syndrome: Three Drug Combinations (IR/IR/ER): Anti-inflammatory/Metformin/ARBs 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with 250 mg to 500 mg Metformin formulated in the IR form will be combined with (ARBs) such as 10 mg to 32 mg Candesartan or 150 mg to 300 mg Irbesartan or 25 mg to 40 mg Olmesartan or 25 mg to Losartan or 100 mg to 320 mg Valsartan or 25 mg to 80 mg Telmisartan or 250 mg to 800 mg Eprosartan formulated in the form of ER.

EXAMPLE 60

FDC Formulations for Clinically Managing Insulin Resistance Syndrome or Metabolic Syndrome: Four Drug Combinations (IR/IR/ER/DR): Anti-inflammatory/DPP-IV Inhibitors/ARBs/ACE Inhibitors 200 mg Ibuprofen or 250 mg Naproxen-Sodium or 325 mg of Aspirin or Aspirin-like drugs (e.g. Ascriptin, Ecotrin) or 50 mg to 400 mg Celecoxib or 200 mg Sulindac or an appropriate dose of other known anti-inflammatory drugs will be formulated in the IR form with anti-type II diabetic DPP-IV inhibitors such as 12.5 mg to 100 mg Sitagliptin, 3 mg to 25 mg Alogliptin or 2.5 mg Linagliptin in an IR form with anti-hypertensive ARBs such as 2 mg to 32 mg Candesartan or 75 mg to 300 mg Irbesartan or 10 mg to 40 mg Olmesartan or 12.5 mg to Losartan or 40 mg to 320 mg Valsartan or 10 mg to 80 mg Telmisartan or 200 mg to 800 mg Eprosartan formulated in the ER form will be combined with lipid lowering Statins such as 80 mg Atorvastatin or 80 mg Provastatin or 40 mg Rosuvastatin or 40 mg Simvastatin formulated in the form of DR.

EXAMPLEs 61-65

Additional FDC Formulations for Clinically Managing Type II Diabetes and Prediabetes

EXAMPLE 61

In Example 61, 50 mg to 400 mg Celecoxib in an IR form will be combined with 500 mg to 1000 mg Metformin in an IR or ER or DR form administered once or twice daily.

EXAMPLE 62

In Example 62, 50 mg to 400 mg Celecoxib in an IR form will be combined with 500 mg to 1000 mg Metformin in an IR or ER or DR form and 80 mg to 160 mg Valsartan in a DR form administered once or twice daily.

EXAMPLE 63

In Example 63, 50 mg to 400 mg Celecoxib in an IR form will be combined with 500 mg to 1000 mg Metformin in an IR or ER or DR form, 80 mg to 160 mg Valsartan in a DR form and 80 mg of Atorvastatin in an ER form administered once or twice daily.

EXAMPLE 64

In Example 64, 50 mg to 400 mg Celecoxib in an IR form will be combined with 5 mg Linagliptin in IR form, 80 to 160 mg Valsartan in a DR form and 80 mg Atorvastatin in an ER form administered once or twice daily.

EXAMPLE 65

Preparation of FDC Formulation of IR (Celecoxib) and ER (Metformin)

Example 65 is directed to the preparation of multilayer tablets of 50 mg to 400 mg Celecoxib in an IR form and 250 mg to 2000 mg of Metformin HCl in an ER form. The IR drug containing layer will contain, e.g., Celecoxib (50 mg to 400 mg), microcrystalline cellulose (50.0 mg), lactose monohydrate (78.0 mg), hydroxyl propyl cellulose (30.0 mg), Croscarmellose sodium (10.0 mg) and magnesium stearate (2.0 mg). The ER drug containing layer will contain Metformin HCl (250 mg to 2000 mg), carnuba wax (290.0 mg), stearic acid (190.0 mg), silicon dioxide (10.0 mg), and magnesium stearate (2.0 mg). The inert layer will contain carnauba wax (100.0 mg), dibasic calcium phosphate (58.0 mg), stearic acid (40 mg), and magnesium stearate (2.0 mg). The subcoating will contain hydroxypropyl methyl cellulose (45.0 mg/tablet), polyethyl glycol 400 (12.0 mg/tablet) and purified water which will be removed during processing. The ER coating will contain Surelease (98.0 mg/tablet), hydroxyl methyl cellulose (98.0 mg/tablet) and purified water which will be removed during processing.

The IR drug containing the layer of the core tablet will be prepared as follows: Celecoxib will be blended with all the ingredients except Croscarmellose sodium and magnesium stearate and granulated with purified with water. The granulate will be dried and milled through a suitable screen. Croscarmellose sodium AND magnesium stearate will be added to the milled granules. The mixture will then be blended for 2 minutes.

The ER drug containing layer of the tablet will be prepared as follows: Metformin HCl and Carnauba wax will be mixed and granulated with a solution of stearic acid in ethyl alcohol.

The granulate will then be dried, milled through a suitable screen. Silicon dioxide and magnesium stearate will be screened and then added to the milled granules. The mixture will then be blended for another 2 minutes.

The inert layer will be prepared as follows: Carnauba wax and dicalcium phosphate will be mixed and granulated with a solution of stearic acid in ethyl alcohol. The granulate will then be dried, milled through a suitable screen. Magnesium stearate will be screened and then added to the milled granules. The mixture will then be blended for another 2 minutes.

The mixture will then be compressed into a multi-layer core tablet in the following sequence: ER containing layer, inert layer and IR drug containing layer using a multi-layer tablet press. Core tablets will then be subcoated.

The subcoating will be prepared by dissolving hydroxypropyl methyl cellulose and polyethylene glycol 400 in purified water and sprayed as a coating solution onto the multi-layer core tablet in a coating pan.

The ER coating will be prepared as follows: In a container purified water will be mixed with hydroxyl propyl methyl cellulose using a mixer until hydroxyl methyl cellulose was completely dissolved. The hydroxymethyl cellulose solution was then added to the surelease dispersion and mixed for 15 minutes. The resulting dispersion will be mixed during the entire coating process. Using the coating pan, the surelease/hydroxypropyl methyl cellulose dispersion will be sprayed onto the subcoated tablets until the required weight gain was achieved.

EXAMPLE 66

Animal Studies

In Example 66, animal studies were conducted based on the methods and FDC formulations described herein. The studies were conducted using good scientific practices following the applicable SOPs of the Testing Facility. Age and weight-matched C57BL/6J lean and DIO male mice were obtained from Jackson Labs (Bar Harbor, Me.). C57BL/6J DIO mice were fed high-fat diet (HFD) for 16 weeks to induce hepatic insulin resistance and pancreatic beta cell dysfunction. USP grade APIs suitable for the finished products were obtained from LGM Pharma (Nashville, Tenn.). Lean control mice were maintained on D12450B (10% Kcal fat) Chow diet and DIO animals were maintained D12492 (60% KCal fat) research diets. Tap water was available ad libitum during the study. Animals were acclimated for a week. Animals were observed by lab technicians during the study and clinical examinations were performed by the veterinarians. Study director and the sponsor were notified in the event of abnormal behavior or observations. Test articles or the drugs were reconstituted in DMSO and 0.5% Methyl cellulose was used as the vehicle.

In a 5-day pilot study, Metformin (300 mg/Kg/day) and sub-maximal dose of Celecoxib (20 mg/Kg/day) were administered together or the vehicle was administered as an oral gavage in the morning. Sub-hypertensive dose of Valsartan (2 mg/Kg/day) or the vehicle was administered 6 hours later. Non-fasting blood glucose levels were determined prior to the drug administration and then every hour for 8 hours using a handheld OneTouch, Ultra Blood Glucose Monitoring System (Johnson & Johnson). In the 5-day study, blood glucose (BG) levels were determined once in the morning prior to the drug administration and again in the afternoon.

Figure 9:
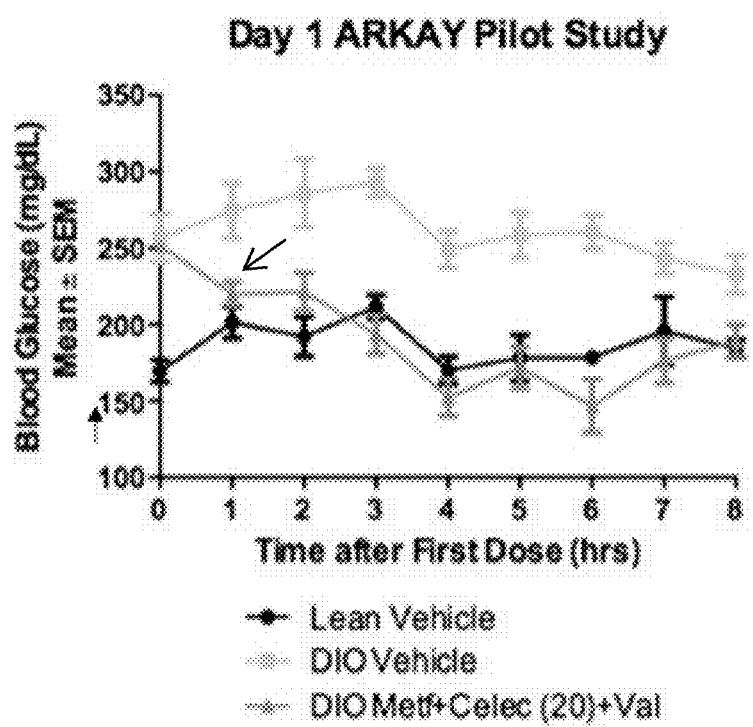
FIG. 9 is a graph plotting mean blood glucose (mg/dl) levels versus time after first dose (hrs) showing that co-administration of Metformin (300 mg/Kg), Celecoxib (20 mg/Kg) and Valsartan (2 mg/Kg) administration improves non-fasting blood glucose levels on day 1 of the administration, wherein the arrow indicates lowering of blood glucose as a result of an increase in first phase of insulin secretion which is a hallmark of improvement in pancreatic beta cell function.

Co-administration of Metformin (Metf), Celecoxib (Celec) and Valsartan (Val) improved non-fasting BG levels in C57BL/6J DIO mice within one hour post administration and the reduced level was maintained for at least 8 hours on the first day of the treatment (N=6) (FIG. 9). Improvement in non-fasting or fed blood glucose levels within one hour post administration is indicative of improvement in pancreatic beta cell dysfunction. Two-way ANOVA, DIO vehicle vs. DIO Metf+Celc+Val, $p<0.0001$ (****) significant.

Figure 10:
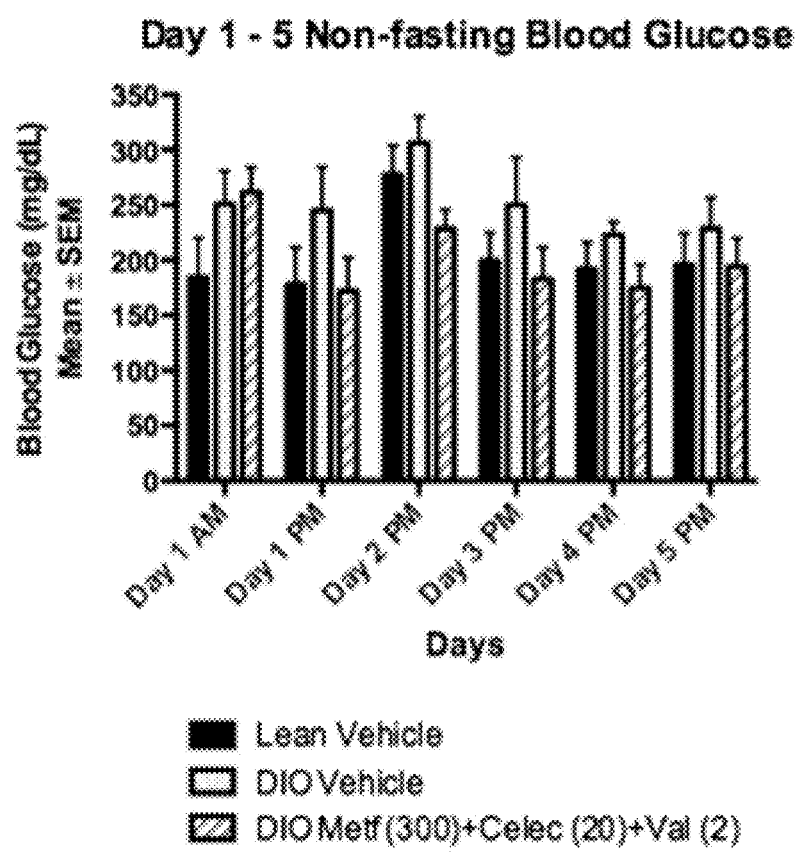
FIG. 10 is a graph plotting mean blood glucose (mg/dl) levels versus time after first dose (days) showing that shows co-administration of Metformin (300 mg/Kg), Celecoxib (20 mg/Kg) and Valsartan (2 mg/Kg) administration improves non-fasting blood glucose levels days 1 through 5.

Co-administration of Metformin, Celecoxib and Valsartan improved non-fasting BG levels in C57BL/6J DIO mice for at least five days with once-a-day oral administration (N=6) (FIG. 10). Two-way ANOVA, DIO vehicle vs. DIO Metf+Celc+Val, $p<0.001$ (***) significant.

In a 29-day study, sub-maximal dose of Metformin (150 mg/Kg/day) and sub-maximal doses of Celecoxib (10 mg/Kg/day or 20 mg/Kg/day) were administered together or the vehicle was administered as an oral gavage in the morning and a sub-hypertensive dose of Valsartan (2 mg/Kg/day) or the vehicle was administered 6 hours later. Non-fasting BG measurements will be taken on Days 1, 15, 22, and 29. Animals were transferred to clean cages, food and water were uninterrupted. A blood sample was collected via tail nick and blood glucose was assessed using a hand-held Glucometer. Body weights were determined twice weekly for the duration of the study period. Animals were observed by lab technicians during the study and clinical examinations were performed by the veterinarians. Body weights did not change significantly with different treatments during the course of the 29-day study.

Figure 11:
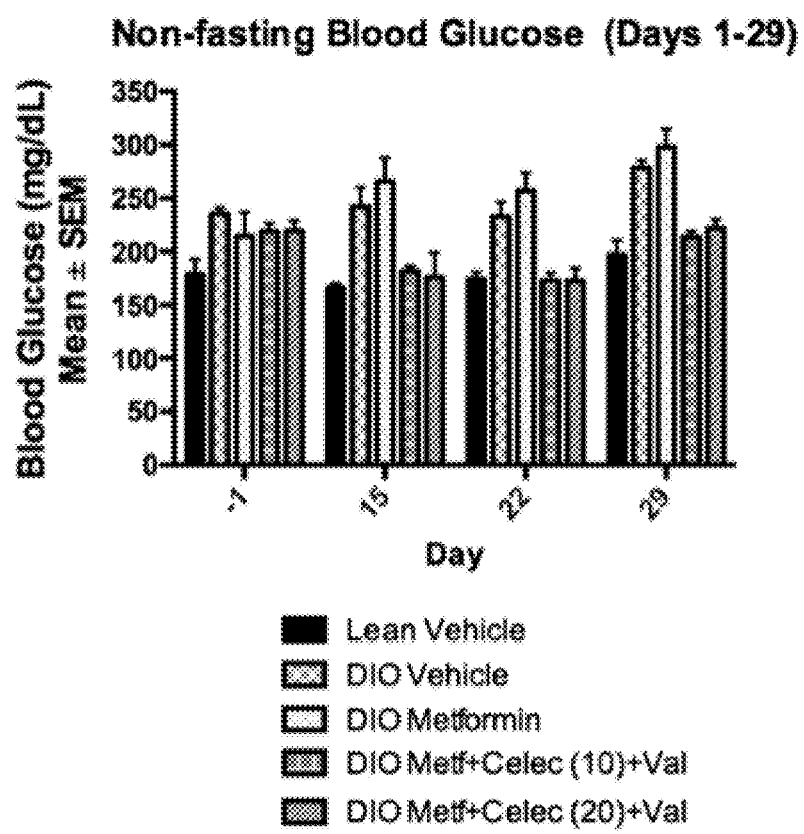
FIG. 11 is a graph plotting mean blood glucose (mg/dl) levels versus time after first dose (hrs) showing that co-administration of Metformin (150 mg/Kg), Celecoxib (10 or 20 mg/Kg) and Valsartan (2 mg/Kg) administration improves non-fasting blood glucose levels on days 1 through 29.

Co-administration of Metformin, Celecoxib and Valsartan counteracted the elevation of non-fasting BG in DIO animals treated with vehicle and DIO animals treated with Metformin (N=6) during the 29-day study (FIG. 11). Co-administration of Metformin, Celecoxib and Valsartan was determined safe during the 29-day study by using body weight as a measure and from observations and clinical examinations by veterinarians.

Oral Glucose Tolerance Test (OGTT) was performed on all the animals on Day 29. Animals were fasted for 5 hours. All animals were kept in clean cages without access to food for 5 hours after BG reading and prior to OGTT. Water was available throughout the course of the OGTT assessment. Test articles were administered by oral gavage 30 minutes prior to the glucose challenge. Each animal was challenged with a glucose load of 2 g/Kg body weight in water. Blood glucose from a tail nick was assessed using a handheld glucometer at 0, 15, 30, 60, 90 and 120 minute time points.

Figure 12:
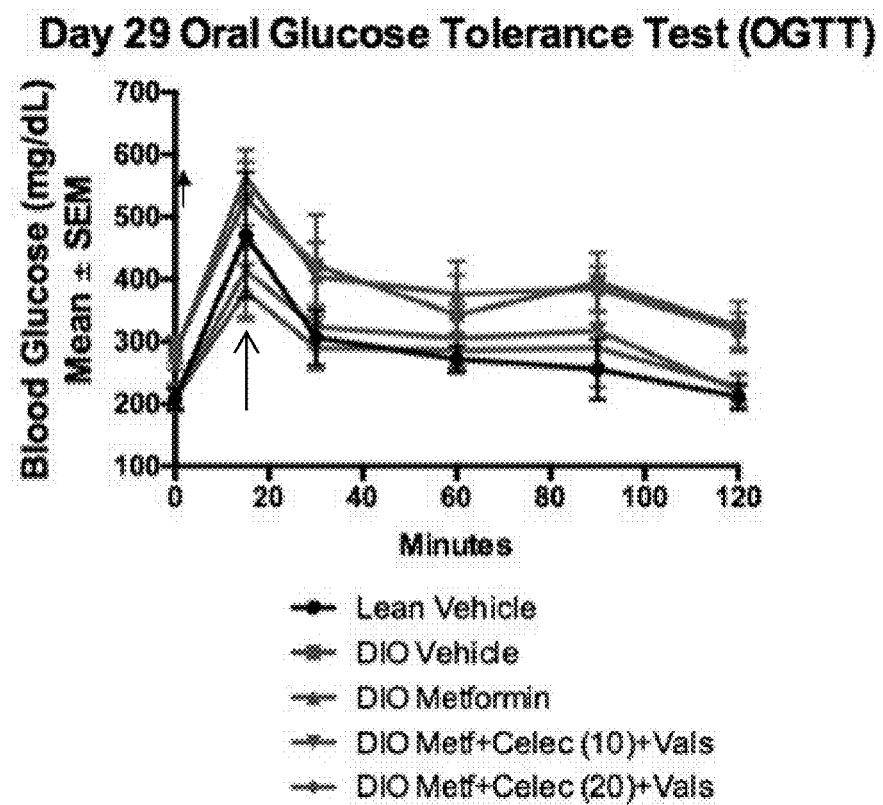
FIG. 12 is a graph plotting mean blood glucose (mg/dl) levels versus time after first dose (hrs) showing that co-administration of Metformin (150 mg/Kg), Celecoxib (10 or 20 mg/Kg) and Valsartan (2 mg/Kg) improves oral glucose tolerance in the oral glucose tolerance test (OGTT), wherein the arrow indicates lowering of blood glucose as a result of an increase in first phase of insulin secretion which is a hallmark of improvement in pancreatic beta cell function.
Figure 13:
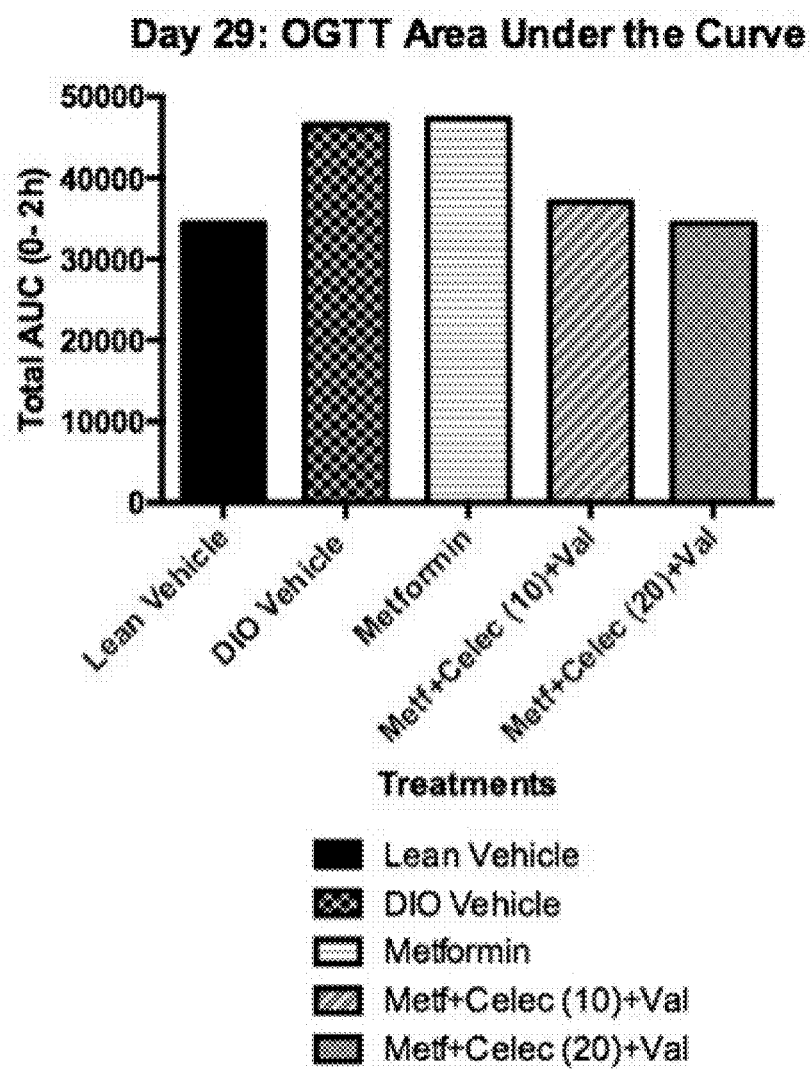
FIG. 13 is a graph plotting OGTT area under the curve (total AUC (0-2 h) showing that co-administration of Metformin (150 mg/Kg), Celecoxib (10 or 20 mg/Kg) and Valsartan (2 mg/Kg) administration improves oral glucose tolerance in the OGTT shown as total area under the curve during the 2-hour study.

Co-administration of Metformin, Celecoxib and Valsartan improved glucose tolerance in the oral glucose tolerance test (OGTT) (FIG. 12). Changes in blood glucose levels after glucose loading are shown. * p<0.0001 vs. DIO vehicle and DIO Metformin. Changes in the total area under the curve (AUC 0-2 h) is shown in FIG. 13. * p<0.0001 vs. DIO vehicle and DIO Metformin.

Blood glucose levels were assessed after 5-hour fast prior to the glucose challenge during the OGTT performed on the 29th day of the study, and demonstrated that co-administration of Metformin (150 mg/Kg), Celecoxib (10 or 20 mg/Kg) and Valsartan (2 mg/Kg) administration improved fasting blood glucose levels. (FIG. 14).

As shown in FIGS. 9 and 12, oral administration of a combination of Metformin, Celecoxib (a selective Cox-2 inhibitor) and Valsartan (an ARB) improves non-fasting blood glucose levels in less than 1 hour post-administration and fasting blood glucose levels in less than 15 minutes in the OGTT by improving the first phase insulin secretion (shown with arrows). Impairment of first phase of insulin secretion is diagnostic of prediabetes as well as overt Type II diabetes.

Figure 15:
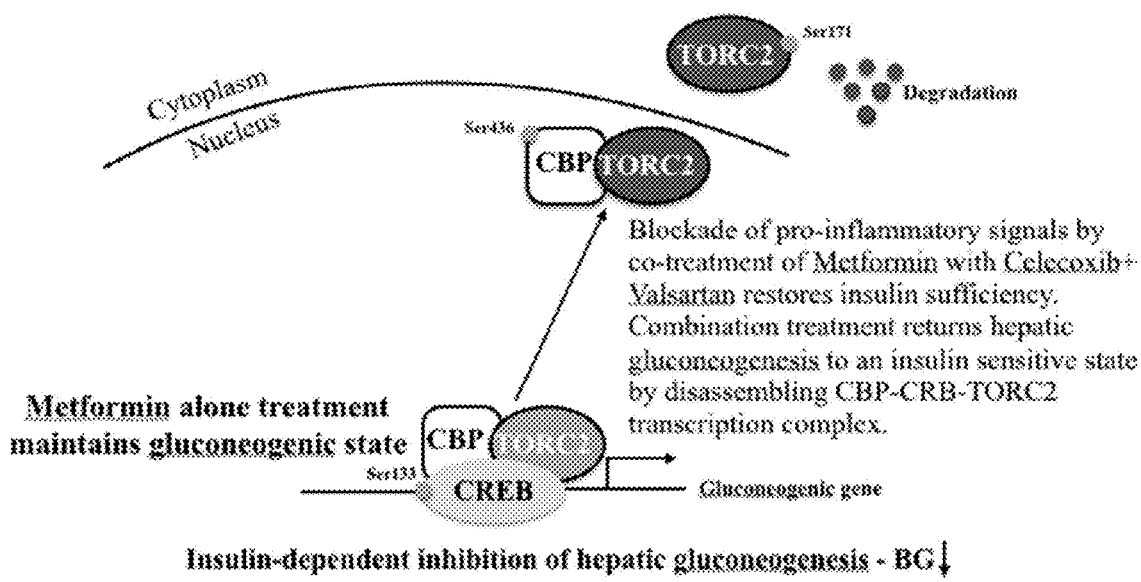
FIG. 15 is a schematic illustration of insulin-dependent blockade of hepatic gluconeogenesis. Co-treatment with Celecoxib and Valsartan restores efficacy of Metformin in C57BL/6J DIO mice with hepatic insulin resistance and pancreatic beta cell dysfunction presumably by disassembling of glucagon-permis sive CBP-CREB-TORC2 transcription complex and by restoring optimal insulin-glucagon molar ratio.

The results of the animal studies disclosed herein demonstrate that pro-inflammatory signals in general and Cox-2-mediated pancreatic cell dysfunction in particular play a critically important role in the development of insulin resistance as well as loss of insulin-sensitive regulation of hepatic gluconeogenesis. Maintenance of normal glucose levels and hepatic gluconeogenesis are tightly controlled by opposing actions of insulin and glucagon. As shown in FIG. 15, treatment with Metformin alone did not suppress elevated non-fasting BG levels but it actually enhanced the BG levels due to lack of insulin-sensitive feed-back regulation of glucagon-mediated hepatic gluconeogenesis. It is hypothesized that in the absence of post-prandial elevation of sufficient insulin due to beta cell dysfunction, Metformin stabilized glucagon-permissive CREB-CBP-TORC2 transcription complex to activate hepatic gluconeogenesis resulting in elevated BG levels. Co-treatment with Celecoxib, a selective Cox-2 inhibitor and a sub-hypertensive yet anti-inflammatory dose of Valsartan counteracted Metformin-mediated elevation in non-fasting BG levels by correcting beta cell dysfunction as well as by restoring insulin sufficiency and insulin sensitivity for regulation of hepatic gluconeogenesis. As illustrated schematically, it is hypothesized that this occurs by insulin-mediated triggering of disassembly of the glucagon-permissive CREB-CBP-TORC2 transcription complex by phosphorylation of co-activator CBP at Ser246, and nuclear exclusion and degradation of co-activator TORC2 by phosphorylation at Ser171 (FIG. 15).

Figure 14:
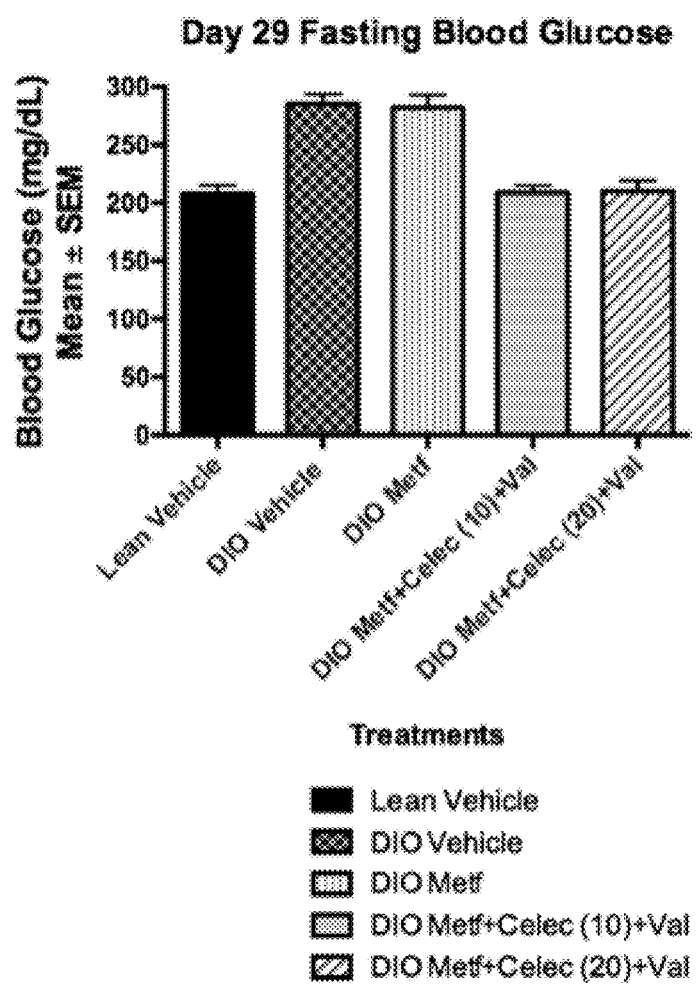
FIG. 14 is a graph plotting mean blood glucose (mg/dl) versus treatments showing that co-administration of Metformin (150 mg/Kg), Celecoxib (10 or 20 mg/Kg) and Valsartan (2 mg/Kg) administration improves fasting blood glucose levels. Blood glucose levels were assessed after 5-hour fast prior to the glucose challenge during the OGTT performed on the 29th day of the study.

As shown in FIGS. 11, 12 and 14, treatment with Metformin alone did not suppress elevated non-fasting BG levels in C57BL/6J DIO (diet-induced obesity) mice but it slightly enhanced the BG levels due to lack of insulin-sensitive feed-back regulation of glucagon-mediated hepatic gluconeogenesis. It is hypothesized that in the absence of post-prandial elevation of sufficient insulin due to beta cell dysfunction, Metformin stabilized glucagon-permissive CREB-CBP-TORC2 transcription complex to activate hepatic gluconeogenesis resulting in elevated BG levels. Co-treatment with sub-optimal dose Celecoxib (10 mg/Kg and 20 mg/Kg), a selective Cox-2 inhibitor and a sub-hypertensive yet anti-inflammatory dose of Valsartan (2 mg/Kg) counteracted Metformin-mediated elevation of non-fasting as well as fasting BG levels by correcting beta cell dysfunction as well as by restoring insulin sufficiency and insulin sensitivity for regulation of hepatic gluconeogenesis. As illustrated schematically, it is hypothesized that this occurs by insulin-mediated triggering of disassembly of the glucagon-permissive CREB-CBP-TORC2 transcription complex by phosphorylation of co-activator CBP at Ser246, and nuclear exclusion and degradation of co-activator TORC2 by phosphorylation at Ser171 (FIG. 15).

CONCLUSION

The above-described results provide proof-of-concept of the anti-inflammatory pancreatic beta cell-centric approach for managing non-fasting (fed) blood glucose levels by oral administration of sub-therapeutic dose of Celecoxib (a selective Cox-2 inhibitor) in combination with therapeutic dose of anti-hyperglycemic drug, Metformin and sub-systolic blood pressure dose of an ARB, Valsartan reduces Blood glucose levels more efficiently in C57BL/6J (B6) DIO (Diet-induced Obesity) mice.

The above-described results provide proof-of-concept that the anti-inflammatory pancreatic beta cell-centric approach for managing non-fasting (fed) Blood glucose levels by oral administration of sub-therapeutic dose of Celecoxib (a selective Cox-2 inhibitor) in combination with therapeutic dose of Metformin and sub-hypertensive dose of Valsartan reduces non-fasting blood glucose levels within one hour post administration on day 1 to near or slightly below the C57BL/6J DIO mice treated with the vehicle. Rapid lowering of non-fasting or fed blood glucose levels is indicative of improvement in pancreatic beta cell dysfunction.

The above-described results provide proof-of-concept of the anti-inflammatory pancreatic beta cell-centric approach for managing non-fasting (fed) blood glucose levels by oral administration of sub-therapeutic dose of Celecoxib (a selective Cox-2 inhibitor) in combination with therapeutic dose of Metformin and sub-systolic blood pressure dose of Valsartan reduces non-fasting blood glucose levels within one hour post administration to near or slightly below the C57BL/6J DIO mice treated with the vehicle and is sustained for at least 8 hours on day 1 of administration.

The above-described results further provide proof-of-concept of the anti-inflammatory pancreatic beta cell-centric approach for managing non-fasting (fed) blood glucose levels by daily (once-a-day) oral administration of sub-therapeutic dose of Celecoxib (a selective Cox-2 inhibitor) in combination with therapeutic dose of Metformin and sub-systolic blood pressure dose of Valsartan reduces non-fasting Blood glucose levels to near or slightly below the C57BL/6J DIO mice treated with the vehicle for at least 5 days.

The above-described results further provide proof-of-concept of the anti-inflammatory pancreatic beta cell-centric approach for managing non-fasting (fed) blood glucose levels by daily (once-a-day) oral administration of sub-therapeutic dose of Celecoxib (a selective Cox-2 inhibitor) in combination with therapeutic dose of Metformin combined as single dose simulating to an Immediate Release (IR) or Quick Release (QR) and administration of sub-systolic blood pressure dose of Valsartan 6 hours later simulating Delayed Release (DR) reduces non-fasting blood glucose levels to near or slightly below the C57BL/6J DIO mice treated with the vehicle for at least 5 days.

The above-described results provide proof-of-concept of the anti-inflammatory pancreatic beta cell-centric approach for managing non-fasting (fed) blood glucose levels by daily (once-a-day) oral administration of sub-therapeutic dose of Celecoxib (a selective Cox-2 inhibitor) in combination with sub-maximal/therapeutic dose of Metformin and sub-systolic blood pressure dose of Valsartan is safe as determined by using body weight (BW) as a measure as well as examination by veterinarians in C57BL/6JJ DIO mice for a long term use of at least 29 days.

Finally, the above-described results suggest that the POC data disclosed here suggest that the anti-inflammatory pancreatic beta cell-centric product combination has the potential for long term sustainable glycemic control by maintaining optimal glucagon-insulin molar ratio by correcting pancreatic beta cell dysfunction and by restoring hepatic insulin sensitivity. For efficient management of insulin resistance, chronic hyperglycemia due to systemic glucose intolerance should not be treated in isolation without treating the causative low-grade inflammation. Progressive deterioration of metabolic control of glucose homeostasis in spite of intense treatments with anti-hyperglycemic drugs is indicative of progressive deterioration of pancreatic islet cell dysfunction resulting in insulin insufficiency. Blood glucose levels and hepatic gluconeogenesis are tightly regulated by opposing actions of insulin and glucagon. Anti-Inflammatory beta-cell centric methods and formulations disclosed are designed to treat pancreatic beta cell dysfunction in combination with insulin resistance by restoring insulin sufficiency as well as restoring insulin sensitivity for hepatic gluconeogenesis as a result of optimal insulin-glucagon molar ratio.

The POC data disclosed here suggest that the anti-inflammatory pancreatic beta cell-centric product combination has the potential to treat impaired post-prandial as well as fasting blood glucose levels. The POC data disclosed here suggest that the anti-inflammatory pancreatic beta cell-centric product combination has the potential to delay, prevent or reduce the severity of obesity-triggered insulin resistance and hyperglycemia in prediabetes, phase I and phase II type 2 diabetes patients. The POC data disclosed here suggest that the anti-inflammatory pancreatic beta cell-centric product combination has the potential for long term sustainable glycemic control would result in better patient CV (cardiovascular) outcomes in long-term clinical studies.

Based on the preclinical data reported herein and information provided herein, for efficient management of insulin resistance, chronic hyperglycemia due to systemic glucose intolerance should not be treated in isolation without treating the causative low-grade inflammation.

Data disclosed herein suggest that treatment with a combination of an anti-hyperglycemic drug such as Metformin, a selective Cox-2 inhibitor such as Celecoxib and anti-hypertensive drug such as Valsartan with their inherent anti-inflammatory capacity has the potential for sustainable glycemic control by correcting pancreatic beta cell dysfunction and by restoring hepatic insulin sensitivity in type 2 diabetes patients with obesity-triggered insulin resistance. As illustrated schematically in FIG. 15, it is hypothesized that sustainable glycemic control is achieved by restoring insulin sensitivity for inhibition of hepatic gluconeogenesis by means of insulin-dependent disruption of glucagon-permissive transcription complex resulting in inhibition of gluconeogenic genes such as PEPCK and PGC-1 alpha.

Pertaining to this disclosure, anti-inflammatory pancreatic beta cell-centric platform combines drugs at the appropriate doses of an anti-inflammatory drug (e.g. a selective Cox-2 inhibitor) with metabolic and cardiovascular disease drugs along with predetermined release kinetics to achieve optimal therapeutic as well as kinetic synergies. In certain preferred embodiments, the anti-inflammatory pancreatic beta cell-centric drug formulations of the invention will be custom-formulated to treat patient-specific comorbidities and more importantly, achieve long term sustainable glycemic control by correcting pancreatic islet dysfunction. The methods and formulations described herein may represent a new first line of therapy and a new standard of care for treating Prediabetes, Phase I and Phase II diabetes patients. It is believed that lowering inflammatory parameters in combination with managing hypertension and lowering lipid profiles would result in more rapid improvement in outcomes with optimal glycemic control. An innovative pharmaceutical formulations and methods platform called "ParamAushadam™" (means Perfect Medicine in Sanskrit, pending, Serial Number: 86/86456) Description: A pharmaceutical finished product methods and formulations technology that combines therapeutically efficacious adverse side effect and DDI-sparing doses of drugs with predetermined modified drug release kinetics to achieve optimal therapeutic as well as kinetic synergies.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, pharmaceutics or related fields are intended to be within the scope of the invention as defined by the following claims.

BIBLIOGRAPHY

1. Garber, A. J. et al. (2013) American association of clinical endocrinologists' comprehensive diabetes management algorithm 2013 consensus statement. Endocrine Practice 10 (Suppl.) 19:1-48.

2. Sullivan, P. W. et al. (2007) The medical cost of cardiometabolic risk factors in the united states. Obesity 15 (12): 3150-3158.
3. Statistics about diabetes (2014) Data from the National Diabetes Statistics Report (released Jun. 10, 2014), American Diabetes Association.
4. www.cdc.gov Mortality data 2010.
5. www.drugstorenews.com Sep. 24, 2013. From GBI Research, Global Business Intelligence
6. www.biovision.com
7. Erik, P. et al (2009) Pathogenesis and Pathophysiology of cardiometabolic syndrome. J. Clin. Hypertension 11 (12): 761-765.
8. Leung, P. S. (2007) Mechanisms of protective effects induced by blockade of the renin-angiotensin system: novel role of the pancreatic islet Angiotensin-generating system in type 2 diabetes. Diabet. Med. 24 (2): 110-116.
9. Aguilar, D. and Solomon, S D (2006) ACE inhibitors and Angiotensin receptor antagonists and the incidence of new-onset diabetes mellitus: an emerging theme. Drugs 66 (9):1169-1177.
10. Choosing a Type 2 diabetes drug (2012) Annals of Internal Medicine, American College of Physicians.
11. Shende, P. et al. (2012) Multi-layered Tablet: Current Scenarios and recent advances. Intl. J. Drug Del. 4: 418-426.
12. Khan, Z. et al. (2013) A novel multi-layered multidisc oral tablet for chronotherapeutic drug delivery. Biomed. Res. Intl. Article ID: 569470, 16 pages.
13. www.webmd.com
14. www.drugs.com
15. Standards of medical care in diabetes—2015 (2015) Diabetes Care 38 (Suppl. 1): S1-S94.
16. Poitou, V. and R. P. Robertson (2009) Glucolipotoxicity: Fuel excess and beta cell dysfunction. Endocrine Reviews 29(3): 351-366.
17. Robertson, R. P. (1998) Dominance of Cyclooxygenase-2 in the regulation of pancreatic islet prostaglandin synthesis. Diabetes 47: 1379-1383.
18. Saltiel, A. (2000) The molecular and physiological basis of insulin resistance: implications for metabolic and cardiovascular diseases. J. Clin. Invest. 100 (2): 163-164.
19. Sauter, N., C. Thienel, Y. Plutino, K. Kampe, E. Dror, S. Traub, K. Tamper, B. Edat, F. Attou, J. Kerr-Conte, A. W. Jehle, M. Boni-Schnitzler and M. Donath (2015) Angiotensin II induces interleukin-1beta-mediated islet inflammation and beta cell dysfunction independently of vasoconstrictive effects. Diabetes 64: 1273-1283.
20. Shu, C. J., C. Benoist and D. Mathis (2012) The immune systems's involvement in obesity-driven type 2 diabetes. Semi. Immunol. 24(6): 436-442.
21. Tateya, S., F. Kim, and Y. Tamori (2013) Recent advances in obesity-induced inflammation and insulin resistance. Frontiers in Endocrine. 4: 1-14.
22. Weir, G. C. and S. Bonner-Weir (2004) Five stages of evolving beta cel dysfunction during progression to diabetes. Diabetes 53 (Suppl. 3): S16-S21.
23. Weir, G. C., G. L King, A. M. Jacobson, A. C. Moses and C. R. Kahn (2005) C. Ronald Kahn—Joslin's Diabetes Mellitus: 14th (fourth) Edition Hardcover—Dec. 6, 2005

What is claimed is:

1. A method of treating Type II diabetes or a pre-diabetic condition in a mammal, comprising orally administering to a patient in need thereof a fixed dose combination comprising a biguanide, a non-steroidal anti-inflammatory, and an Angiotensin II Type 1 receptor blocker on a chronic basis, wherein the biguanide is metformin, the non-steroidal anti-inflammatory drug is celecoxib, and the Angiotensin II Type 1 receptor blocker is valsartan.

2. The method of claim 1, wherein the dose of the non-steroidal anti-inflammatory drug and/or the dose of the Angiotensin II Type 1 receptor blocker is sub-therapeutic.

3. The method of claim 1, wherein the mammal is human and the administration of the fixed dose combination improves non-fasting blood glucose levels in less than one hour post-administration and fasting blood glucose levels in less than 15 minutes after the oral glucose load in an Oral glucose Tolerance Test (OGTT).

4. The method of claim 1 wherein the dose of metformin is from about 250 mg to about 2000 mg, the dose of celecoxib is from about 50 mg to about 400 mg and the dose of valsartan is from about 40 mg to about 320 mg.

5. The method of claim 1, further comprising providing sub-maximal amounts of metformin, celecoxib and valsartan.

6. The method of claim 1, wherein the human is suffering from pre-diabetes.

7. The method of claim 1, wherein the patient is a human is suffering from inadequate glycemic control and was previously treated with an anti-hyperglycemic drug(s).

8. The method of claim 1, further comprising providing the valsartan in delayed release form.

9. The method of claim 1, wherein the dose of valsartan is released 6 hours after the dose of metformin.

10. The method of claim 1, further comprising providing one or more of metformin, celecoxib and valsartan in modified release form.

11. The method of claim 1, further comprising providing one or more of metformin, celecoxib and valsartan in controlled or delayed release form.

12. The method of claim 1, further comprising providing the metformin, celecoxib and valsartan in therapeutically effective amounts.

13. The method of claim 1, further comprising providing the metformin in immediate or extended release form, the celecoxib in immediate release form, and the valsartan in delayed release form.

14. The method of claim 1, wherein the combination of Metformin, Valsartan and Celecoxib improves glycemic parameters such as: (i) lower Hemoglobin A1c (HbA1c) levels, (ii) improve oral glucose tolerance in oral glucose tolerance test (OGTT), (iii) improve beta-cell function, (iv) lower fasting and non-fasting (post-prandial) glucose levels, (v) improve acute insulin response to glucose (AIRg) and first phase of insulin secretion, (vi) improve post-prandial or non-fasting glucose excursion and/or (vii) improve NAS (NAFLD [Non-alcoholic fatty liver disease] Activity scores) in NASH (Non-alcoholic steatohepatitis) patients.

15. The method of claim 1, further comprising providing a sub-therapeutic dose of celecoxib, providing a sub-maximal or therapeutic dose of metformin, and providing a sub-systolic blood pressure dose of valsartan.

16. The method of claim 1, further comprising providing a sub-hypertensive dose or sub-systolic blood pressure dose of valsartan.

17. The method of claim 1, further comprising providing a sub-therapeutic dose of celecoxib, providing a sub-maximal or therapeutic dose of metformin.

18. The method of claim 1, further comprising providing a sub-therapeutic dose of celecoxib.

19. The method of claim 15, wherein the sub-maximal and sub-therapeutic dose of celecoxib and the sub-systolic blood pressure dose of valsartan restore the efficacy of metformin.

20. The method of claim 15, wherein the sub-maximal and sub-therapeutic dose of celecoxib and the sub-systolic blood pressure dose of valsartan and sub-maximal dose of metformin delays insulin dependency or initiation of insulin therapy by maintaining insulin sufficiency.

21. A method for managing non-fasting (fed) blood glucose levels in a human patient suffering from Type II diabetes or prediabetes by daily (once-a-day) oral administration of sub-therapeutic dose of celecoxib in combination with therapeutic dose of metformin combined as single dose in immediate release (IR) or quick release (QR) form and administration of sub-systolic blood pressure dose of Valsartan 6 hours later in delayed release (DR) form.

* * * * *